US011873518B2

United States Patent
Romney et al.

(10) Patent No.: US 11,873,518 B2
(45) Date of Patent: Jan. 16, 2024

(54) ENGINEERED SYNTHASE FOR PRODUCTION OF TRYPTOPHAN DERIVATIVES AND INTRANSIGENT SUBSTRATES

(71) Applicant: California Institute of Technology, Pasadena, CA (US)

(72) Inventors: David K. Romney, Pasadena, CA (US); Javier Murciano Calles, Ubeda Jaen (ES); Jori E. Wehrmuller, Hohenrain (CH)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 17/724,390

(22) Filed: Apr. 19, 2022

(65) Prior Publication Data

US 2022/0259581 A1    Aug. 18, 2022

Related U.S. Application Data

(62) Division of application No. 15/685,839, filed on Aug. 24, 2017, now Pat. No. 11,332,729.

(60) Provisional application No. 62/507,383, filed on May 17, 2017, provisional application No. 62/462,193, filed on Feb. 22, 2017, provisional application No. 62/379,039, filed on Aug. 24, 2016.

(51) Int. Cl.
| | |
|---|---|
| *C12N 15/66* | (2006.01) |
| *C12N 9/88* | (2006.01) |
| *C12P 13/22* | (2006.01) |
| *C07D 209/20* | (2006.01) |

(52) U.S. Cl.
CPC ............. *C12N 9/88* (2013.01); *C07D 209/20* (2013.01); *C12P 13/227* (2013.01); *C12Y 402/0102* (2013.01)

(58) Field of Classification Search
CPC ........ C12N 9/88; C12N 15/66; C07D 209/20; C12P 13/22; C12Y 402/0102
See application file for complete search history.

(56) References Cited

U.S. PATENT DOCUMENTS

| | | | |
|---|---|---|---|
| 5,374,543 A | 12/1994 | Murdock | |
| 6,441,274 B1 | 8/2002 | Cahoon et al. | |
| 6,605,709 B1 | 8/2003 | Breton | |
| 10,513,719 B2 | 12/2019 | Buller et al. | |
| 2004/0029129 A1 | 2/2004 | Wang et al. | |
| 2016/0298152 A1 | 10/2016 | Buller et al. | |

FOREIGN PATENT DOCUMENTS

| | | |
|---|---|---|
| JP | 2008237075 A | 10/2008 |
| WO | 9534657 A2 | 12/1995 |

OTHER PUBLICATIONS

"RecName: Full=Tryptophan Synthase Beta Chain 1", GeneSeq Database, Accession No. Q9V1G8, 2001, 2 pages.
Buller et al., "Directed Evolution of the Tryptophan Synthase β-Subunit for Stand-Alone Function Recapitulates Allosteric Activation", Proceedings of the National Academy of Sciences, vol. 112, No. 47, Nov. 24, 2015, pp. 14599-14604.
Deckert et al., Uniprot Database, Accession No. O66923, May 2005, 3 pages.
EP17844448.5, "Extended European Search Report", dated Jun. 26, 2020, 13 pages.
EP17844448.5, "Partial Supplementary European Search Report", dated Jan. 30, 2020, 15 pages.
Herger et al., "Synthesis of B-Branched Tryptophan Analogs Using an Engineered Subunit of Tryptophan Synthase", Journal of the American Chemical Society, vol. 138, No. 27, Jul. 13, 2016, pp. 8388-8391.
Murciano-Calles et al., "A Panel of TrpB Biocatalysts Derived from Tryptophan Synthase through the Transfer of Mutations that Mimic Allosteric Activation", Angewandte Chemie International Edition in English, vol. 55, No. 38, Sep. 12, 2016, pp. 11577-11581.
PCT/US2017/048494, "International Search Report and Written Opinion", dated Dec. 27, 2017, 7 pages.
Romney et al., "Unlocking Reactivity of TrpB: A General Biocatalytic Platform for Synthesis of Tryptophan Analogues", Journal of the American Chemical Society, vol. 139, No. 31, Aug. 9, 2017, pp. 10769-10776.
"Tryptophan Synthase Beta Chain from *Pyrococcus* Sp. (Strain NA2); EC=4.2.1.20", Database UniProt, EBI Accession No. UNIPROT:F4HJI6 Database Accession No. F4HJI6, Jun. 28, 2011, 1 page.
EP17844448.5, "Office Action", dated Sep. 7, 2023, 6 pages.

*Primary Examiner* — Maryam Monshipouri
(74) *Attorney, Agent, or Firm* — Kilpatrick Townsend & Stockton LLP

(57) ABSTRACT

This disclosure relates to modified tryptophan synthase and more particularly to modified beta-subunits of tryptophan synthase. The disclosure further relates to cells expressing such modified subunits and methods of producing non-canonical amino acids.

18 Claims, 11 Drawing Sheets
Specification includes a Sequence Listing.

```
MUTATIONS                                                                         VG
Pyrococcus furiosus     ------------------MWFGEFGGQYVPETLIEPLKELELEKAYKRFKDDEEFNRQLNYYLKTWA   47
Archaeoglobus fulgidus  MRCWLENLSGGRKMKFGEFGGRFVPEVLIPPLEELEKAYDRFKDDEEFKARLEYYLKSYA           60
Thermotoga maritima     -------------------MKGYFGPYGGQYVPEILMPALEELEAAYEEIMKDESFWKEFNDLLRDYA   49
Escherichia coli        -----------------MTTLLNPYFGEFGGMYVPQILMPALRQLEEAFVSAQKDPEFQAQFNDLLKNYA 53
                                            **  :: *** :**   *:  ::*    .  :   . :*

MUTATIONS                                   V                              L                    G
Pyrococcus furiosus     GRPTPLYYAKRLTEKIGGAKIYLKREDLVHGGAHKTNNAIGQALLAKFMGKTRLIAETGA          107
Archaeoglobus fulgidus  GRPTPLYFAENLSREL-GVKIYLKREDLLHGGAHKINNTIGQALLAKFMGKKRVIAETGA          119
Thermotoga maritima     GRPTPLYFARRLSEKY-GARIYLKREDLLHTGAHKINNAIGQVLLAKKMGKTRIIAETGA          108
Escherichia coli        GRPTALTKCQNITAGT-NTTLYLKREDLLHGGAHKTNQVLGQALLAKRMGKTEIIAETGA          112
                        ****  .        .  :********:*.****.*:::**:***: ***.*:*****

MUTATIONS                                                                   L                D
Pyrococcus furiosus     GQHGVATAMAGALLGMKVDIYMGAEDVERQKMNVFRMKLLGANVIPVNSGSRTLKDAINE          167
Archaeoglobus fulgidus  GQHGVATAMAAALLGLEAEIYMGAEDYERQKMNVFRMELLGAKVTAVESGSRTLKDAINE          179
Thermotoga maritima     GQHGVATATAAALFGMECVIYMGEEDTIRQKPNVERMKLLGAKVVPVKSGSRTLKDAINE          168
Escherichia coli        GQHGVASALASALLGLKCRIYMGAKDVERQSPNVFRMRLMGAEVIPVHSGSATLKDACNE          172
                        ******: :*.**:*:: :****: * :**  **.**:*:.*: : ** :***** **

MUTATIONS                    F   A                                          P
Pyrococcus furiosus     ALRDWVATFEYTHYLIGSVVGPHPYPTIVRDFQSVIGREAKAQILEAEGQLPDVIVACVG          227
Archaeoglobus fulgidus  ALRDWVESFEHTHYLIGSVVGPHPHFPTIVRDFQAVIGKEARRQIIEAEGGMPDAIIACVG          239
Thermotoga maritima     ALRDWITNLQTTYYVIGSVVGPHPYPIIVRNFQKVIGEETKKQILEKEGRLPDYIVACVG          228
Escherichia coli        ALRDWSGSYETAHYMLGTAAGPHPYPTIVREFQRMIGEETKAQILEREGRLPDAVIACVG          232
                        *****      :  *::*:.*****.* ***.** :** :  ** *.:*  ** *:****

MUTATIONS                                                           S
Pyrococcus furiosus     GGSNAMGIFYPFVNDKKVKLVGVEAGGKGLESGKHSASLNAGQVGVFHGMLSYFLQDEEG          287
Archaeoglobus fulgidus  GGSNAMGIFHPFLND-DVRLIGVEAGGEGIESGRHSASLTAGSKGVLHGMLSYFLQDEEG          298
Thermotoga maritima     GGSNAAGIFYPFIDS-GVKLIGVEAGGEGLETGKHAASLLKGKIGYLHGSKTFVLQDDWG          287
Escherichia coli        GGSNAIGMFADFINETNVGLIGVEPGGHGIETGEHGAPLKHGRVGIYFGMKAPMMQTEDG          292
                        ***** *:* *:       .* ***.** *:.*:*.* *  *  * :.    . *: *
```

FIG. 2

```
                         MUTATIONS                                    S                                    A
Pyrococcus furiosus      QIKPTHSIAPGLDYPGVGPEHAYLKKIQRAEYVTVTDEEALKAFHELSRTEGIIPALESA  347
Archaeoglobus fulgidus   MMLDTHSVSAGLDYPGVGPEHAYLKETGRCEYVTVNDEEALRAFKTLSKLEGIIPALESA  358
Thermotoga maritima      QVQVTHSVSAGLDYSGVGPEHAYWRETGKVLYDAVTDEEALDAFIELSRLEGIIPALESS  347
Escherichia coli         QIEESYSISAGLDFPSVGPQHAYLNSTGRADYVSITDDEALEAFKTLCLHEGIIPALESS  352
                           ::*:  ****: .******   .     *  ::.**** **  ***********:

MUTATIONS                                                    A
Pyrococcus furiosus      HAVAYAMKLAKE-MSRDEIIVNLSGRGDKDLDIVLKVSGNV-----  388
Archaeoglobus fulgidus   HAIAYAMKMAEE-MQRDDVLVVNLSGRGDKDKDMDIVRRLA-----  397
Thermotoga maritima      HALAYLKKIN----IKGKVVVVNLSGRGDKDLESVLNHPYVRERIR  389
Escherichia coli         HALAHALKMMRENPDKEQLIVVNLSGRGDKDIFTVHDILKARGEI-  397
                          *:     :  :  :::*************:    *
```

FIG. 2 (continued)

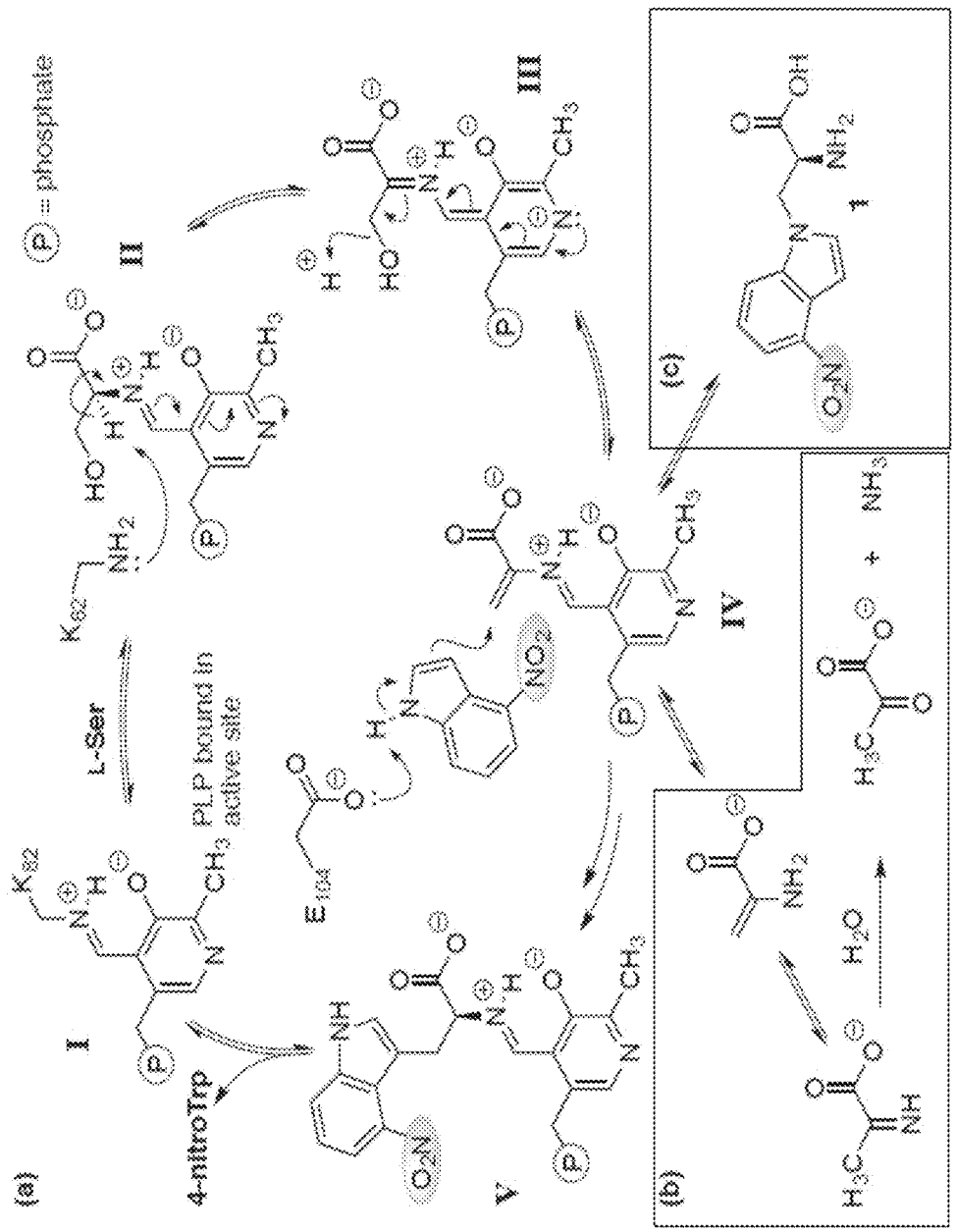
FIG. 4A-C

ENGINEERED SYNTHASE FOR PRODUCTION OF TRYPTOPHAN DERIVATIVES AND INTRANSIGENT SUBSTRATES

CROSS REFERENCE TO RELATED APPLICATIONS

This application is a division of U.S. Non-Provisional application Ser. No. 15/685,839, filed Aug. 24, 2017, which claims priority under 35 U.S.C. 119 to U.S. Provisional Application Ser. No. 62/379,039, filed Aug. 24, 2016, U.S. Provisional Application Ser. No. 62/462,193, filed Feb. 22, 2017 and U.S. Provisional Application No. 62/507,383, filed May 17, 2017, the disclosures of which are incorporated herein by reference.

STATEMENT REGARDING FEDERALLY SPONSORED RESEARCH

This invention was made with government support under Grant No. GM117635 awarded by the National Institutes of Health. The government has certain rights in the invention.

INCORPORATION BY REFERENCE OF SEQUENCE LISTING

Accompanying this filing is a Sequence Listing entitled "sequence_ST25.txt", created on Aug. 24, 2017 and having 122 kB of data, machine formatted on IBM-PC, MS-Windows operating system. The sequence listing is hereby incorporated by reference in its entirety for all purposes.

TECHNICAL FIELD

This invention relates to modified tryptophan synthase and more particularly to modified beta-subunits of tryptophan synthase. The invention further relates to cells expressing such modified subunits and methods of using such modified subunits for the production of tryptophan derivatives and other chemical entities that are challenging to synthesize.

BACKGROUND

Heteromeric enzyme complexes catalyzing a rich array of useful reactions are often allosterically regulated by their protein partners, such that the catalytic subunits are much less active when isolated. Utilizing isolated enzyme subunits, however, is desirable for biosynthetic applications, wherein expressing large complexes increases the metabolic load on the host cell and complicates efforts to engineer activity, substrate specificity, stability, and other properties.

Tryptophan synthase (TrpS; EC 4.2.1.20) is a heterodimeric complex that catalyzes the formation of L-tryptophan (Trp) from L-serine (Ser) and indole glycerol phosphate (IGP) (see, FIG. 1A). The mechanism of this transformation has been extensively studied for TrpS from *Escherichia coli* and *Salmonella typhimurium*, where it has been shown that the enzyme consists of two subunits, TrpA (α-subunit) and TrpB (β-subunit), both of which have low catalytic efficiencies in isolation. The activities of both subunits increase upon complex formation and are further regulated by an intricate and well-studied allosteric mechanism. IGP binding to the α-subunit stimulates pyridoxal phosphate (PLP)-dependent aminoacrylate formation in the β-subunit [E(A-A); FIG. 1B], which in turn promotes retro-aldol cleavage of IGP in the α-subunit, releasing indole. This tightly choreographed mechanism serves to prevent the free diffusion of indole, which is only released from the α-subunit when the complex is in a closed conformation that forms a 25-Å tunnel through which indole diffuses into the β-subunit. Here, indole reacts with E(A-A) in a C—C bond-forming reaction, yielding L-tryptophan as product (FIG. 1B). These allosteric effects are mediated through the rigid-body motion of the communication (COMM) domain and a monovalent cation (MVC) binding site within the β-subunit (FIG. 1A), which undergo complex conformational transitions associated with open, partially closed, and fully closed states during the catalytic cycle.

SUMMARY

The disclosure provides TrpB-derived biocatalysts that exhibit activity with mono- and disubstituted indoles. The substrate scope includes indoles bearing electron-withdrawing groups, such as nitro and cyano, which are fundamentally deactivating in this reaction manifold. The disclosure showcases the potency of the amino-acrylate as an electrophile, as well as the ability of the active site to protect the amino-acrylate from degradation, while promoting reactions with even the most stubborn nucleophiles. These qualities make mutant-TrpB catalysis a versatile and easy-to-use platform for the production of valuable synthetic building blocks.

The disclosure provides a recombinant polypeptide comprising an isolate β-subunit of tryptophan synthase (EC 4.2.1.20), wherein the isolate β-subunit comprises at least one mutation that stabilizes the closed state of the isolate β-subunit wherein the recombinant polypeptide catalyzes the production of tryptophan analogs substituted at the 4-, 5-, 6- and/or 7-position using serine and an indole analog as a substrate. In one embodiment, the isolate β-subunit has a sequence that is at least 57% to 99% identical to SEQ ID NO:2. In another embodiment, the indole analog comprises a structure as set forth in Formula I:

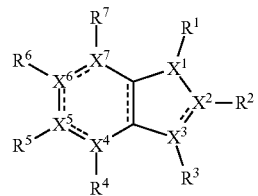

wherein $X_1$-$X_7$ are independently either a carbon, nitrogen, oxygen, or sulfur; $R_1$-$R_3$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen and $R_4$-$R_7$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen, wherein at least one of $R_4$-$R_7$ is an electron withdrawing group. In another embodiment, the indole analog has a structure of Formula II:

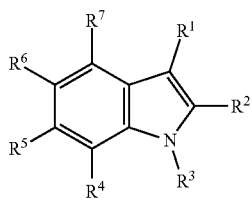

wherein, $R_1$-$R_3$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen and $R_4$-$R_7$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen, wherein at least one of $R_4$-$R_7$ is an electron withdrawing group. In yet another embodiment, the indole analog is selected from the group consisting of:

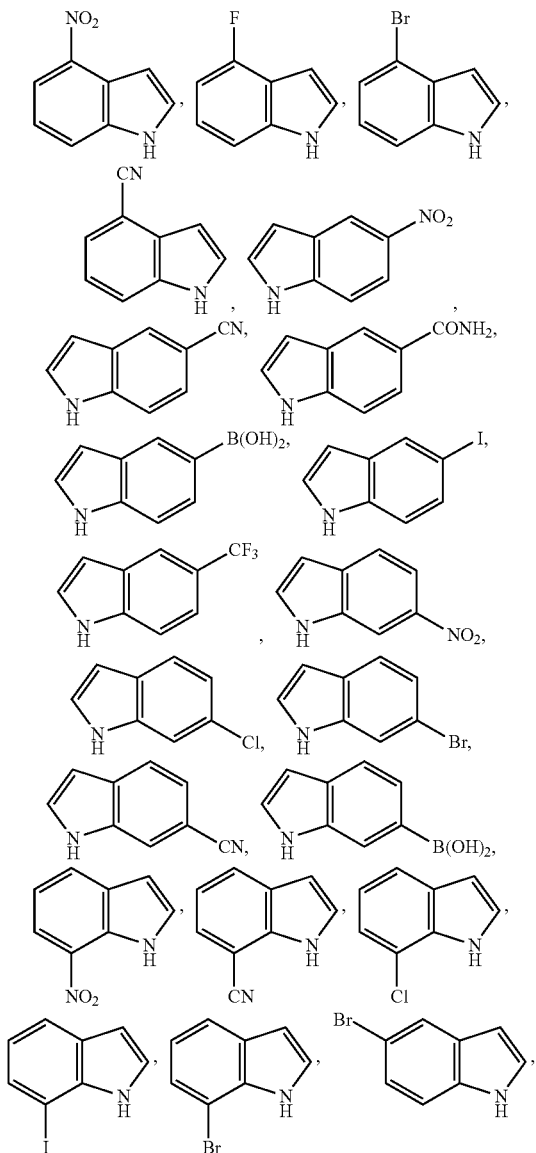

-continued

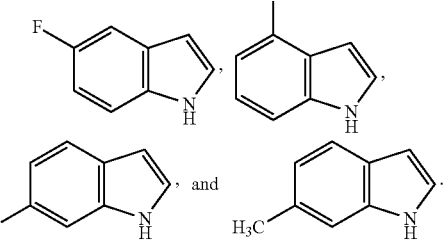

In yet another embodiment, the recombinant polypeptide comprises a sequence selected from the group consisting of: (a) about 57% or more identity to SEQ ID NO:2 and has activating mutations at positions 16, 17, 68, 95, 104, 139, 166, 183, 186, 212, 274, 292, 321 and 384; (b) about 57% or more identity to SEQ ID NO:4 and has activating mutations at positions 29, 30, 80, 107, 116, 151, 178, 195, 198, 224, 285, 303, 332, and 395; (c) about 57% or more identity to SEQ ID NO:6 and has activating mutations at positions 18, 19, 69, 96, 105, 140, 167, 184, 187, 213, 274, 292, and 381; and (d) about 57% or more identity to SEQ ID NO:8 and has activating mutations at positions 22, 23, 73, 100, 109, 144, 171, 188, 217, 279, 326, and 390. In a further embodiment, the activating mutations of (a) are selected from the group consisting of I16V, E17G, I68V, F95L, E104G or E104A, M139L, N166D, I183F, V186A, L212P, F274S, T292S, T321A, V384A and any combination thereof relative to SEQ ID NO:2. In another embodiment, the activating mutation of (b) are selected from the group consisting of I29V, P30V, I80V, F107L, E116G or E116A, M151L, N178D, I195F, V198A, I224P, L285S, T303S, T332A, R395A and any combination thereof relative to SEQ ID NO:4. In still another embodiment, the activating mutation of (c) are selected from the group consisting of M18V, P19G, I69V, K96L, E105G (or E105A), P140L, N167D, I184F, V187A, L213P, L274S, T292S, H381A and any combination thereof relative to SEQ ID NO:6. In another embodiment, the activating mutation of (d) are selected from the group consisting of M22V, P23G, L73V, R100L, E109G or E109A, P144L, N171D, L188F, L217P, Y279S, S326A, I390A and any combination thereof relative to SEQ ID NO:8. In another embodiment, the polypeptide is at least 80% identical to SEQ ID NO:14, 16, 18, 20, 22, 24 or 26 and wherein the polypeptide catalyzes the production of tryptophan analogs substituted at the 4-, 5-, 6- and/or 7-position using serine and an indole analog as a substrate.

The disclosure also provides an isolated nucleic acid encoding any of the polypeptide embodiments set forth herein.

The disclosure also provides a vector containing a polynucleotide of the disclosure. In one embodiment, the vector is an expression vector.

The disclosure also provides recombinant host cells that have been transformed or transfected with a nucleic acid or vector of the disclosure.

The disclosure also provides a method for producing tryptophan analog, a non-canonical amino acid and/or an unnatural amino acid comprising contacting an indole analog and L-serine with a polypeptide of the disclosure.

The disclosure provides a method for producing a tryptophan analog substituted at the 4-, 5-, 6- and/or 7-position, the method comprising (a) providing L-serine, an indole analog substituted at the 4-, 5-, 6- and or 7-position and an isolated β-subunit of tryptophan synthase (EC 4.2.1.20)

having at least a mutation corresponding to E104 of SEQ ID NO:10; and (b) admixing the components of (a) in a reaction for a time and under conditions to produce the tryptophan analog. In one embodiment, the indole analog comprises a structure as set forth in Formula I:

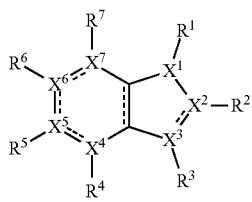

wherein $X_1$-$X_7$ are independently either a carbon, nitrogen, oxygen, or sulfur; $R_1$-$R_3$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen and $R_4$-$R_7$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen, wherein at least one of $R_4$-$R_7$ is an electron withdrawing group. In another embodiment, the indole analog has a structure of Formula II:

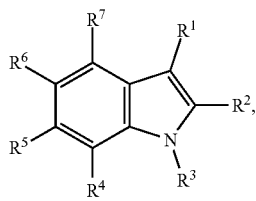

wherein $R_1$-$R_3$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen and $R_4$-$R_7$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen, wherein at least one of $R_4$-$R_7$ is an electron withdrawing group. In yet another embodiment, the indole analog is selected from the group consisting of:

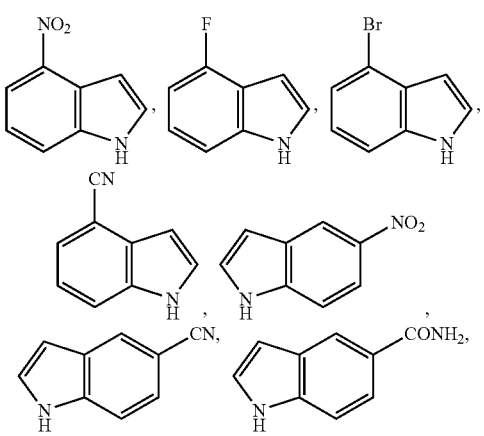

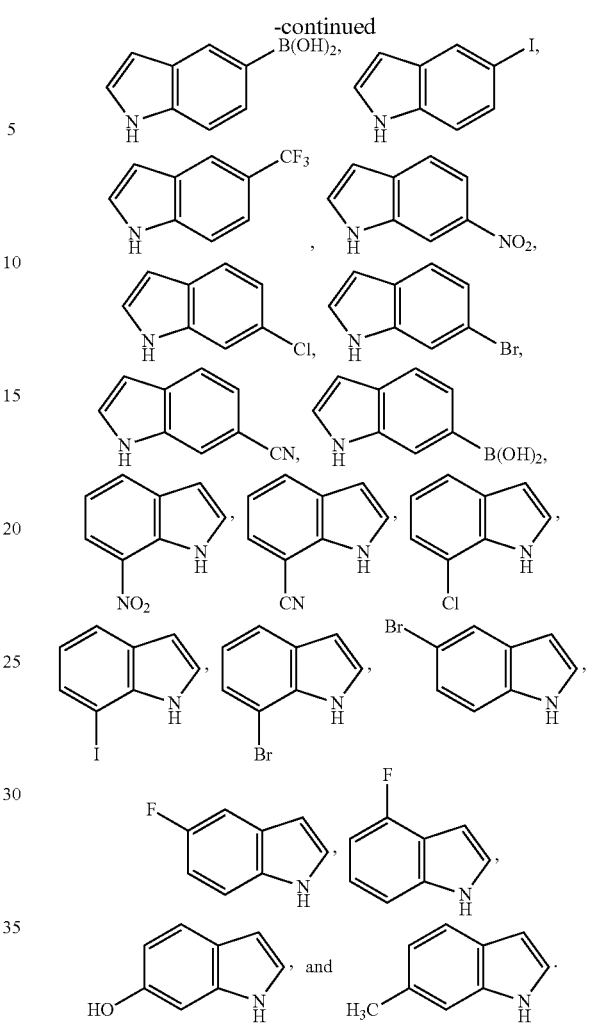

In another embodiment, the β-subunit of tryptophan synthase is from *E. coli, S. typhimurium, P. furiosus, A. fulgidus* or *T. maritima*. In another embodiment, the recombinant polypeptide comprises a sequence selected from the group consisting of (a) about 57% or more identity to SEQ ID NO:2 and has activating mutations at positions 16, 17, 68, 95, 104, 139, 166, 183, 186, 212, 274, 292, 321 and 384; (b) about 57% or more identity to SEQ ID NO:4 and has activating mutations at positions 29, 30, 80, 107, 116, 151, 178, 195, 198, 224, 285, 303, 332, and 395; (c) about 57% or more identity to SEQ ID NO:6 and has activating mutations at positions 18, 19, 69, 96, 105, 140, 167, 184, 187, 213, 274, 292, and 381; and (d) about 57% or more identity to SEQ ID NO:8 and has activating mutations at positions 22, 23, 73, 100, 109, 144, 171, 188, 217, 279, 326, and 390. In a further embodiment, the activating mutations of (a) are selected from the group consisting of I16V, E17G, I68V, F95L, E104G or E104A, M139L, N166D, I183F, V186A, L212P, F274S, T292S, T321A, V384A and any combination thereof relative to SEQ ID NO:2. In another embodiment, the activating mutation of (b) are selected from the group consisting of I29V, P30V, I80V, F107L, E116G or E116A, M151L, N178D, I195F, V198A, I224P, L285S, T303S, T332A, R395A and any combination thereof relative to SEQ ID NO:4. In yet another embodiment, the activating mutation of (c) are selected from the group consisting of M18V, P19G, I69V, K96L, E105G or E105A, P140L, N167D, I184F, V187A, L213P, L274S, T292S, H381A and any combination thereof relative to SEQ ID NO:6. In still another embodiment, the activating mutation of (d) are selected from the group consisting of M22V, P23G, L73V, R100L, E109G or E109A, P144L, N171D, L188F, L217P, Y279S, S326A, I390A and any combination thereof relative to SEQ ID NO:8. In yet another embodiment, the polypeptide is at least 80% identical to SEQ ID NO:14, 16, 18, 20, 22, 24 or 26 and wherein the polypeptide catalyzes the production of tryptophan analogs substituted at the 4-, 5-, 6- and/or 7-position using serine and an indole analog as a substrate. In still another embodiment, the method is carried out in a cell free system.

The disclosure also provides a reaction mixture for carrying out the method of the disclosure, wherein the reaction mixtures comprises a buffer, pyridoxal phosphate, an indole analog, L-serine and an isolated β-subunit of tryptophan synthase having at least 80% identity to SEQ ID NO:10 and having an mutation at E104.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

FIG. 2 shows a multiple sequence alignment of Pf (SEQ ID NO:2), Af (SEQ ID NO:4), Tm (SEQ ID NO:6) and Ec (SEQ ID NO:8) TrpB homologs. The mutated residues identified in the present disclosure are shown above the first line. Symbols under sequences: (*) identify identical residues, (:) report for residues of equal nature, and (.) recognize roughly similar residues.

FIG. 4A-C shows Putative reaction pathways for reaction with 4-nitroindole. (A) Catalytic cycle for formation of 4-nitroTrp. (B) Enzymatic decomposition of Ser. (C) Competitive formation of isotryptophan 1.

Like reference symbols in the various drawings indicate like elements.

DETAILED DESCRIPTION

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used in this specification and the appended claims, the singular forms "a," "an," and "the" include plural referents unless the content clearly dictates otherwise.

Unless defined otherwise, all technical and scientific terms used herein have the same meaning as commonly understood by one of ordinary skill in the art to which the invention pertains. Although any methods and materials similar or equivalent to those described herein can be used in the practice for testing of the invention(s), specific examples of appropriate materials and methods are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Where a range is recited, the disclosure contemplates any value between the range and includes sub-ranges within the range. Moreover, a percentage of "at least X %" includes X % up to any including 100% unless clearly indicated otherwise, and includes any percentage value therebetween.

Any publications discussed above and throughout the text are provided solely for their disclosure prior to the filing date of the present application. Nothing herein is to be construed as an admission that the inventors are not entitled to antedate such disclosure by virtue of prior disclosure.

Figure 1A:
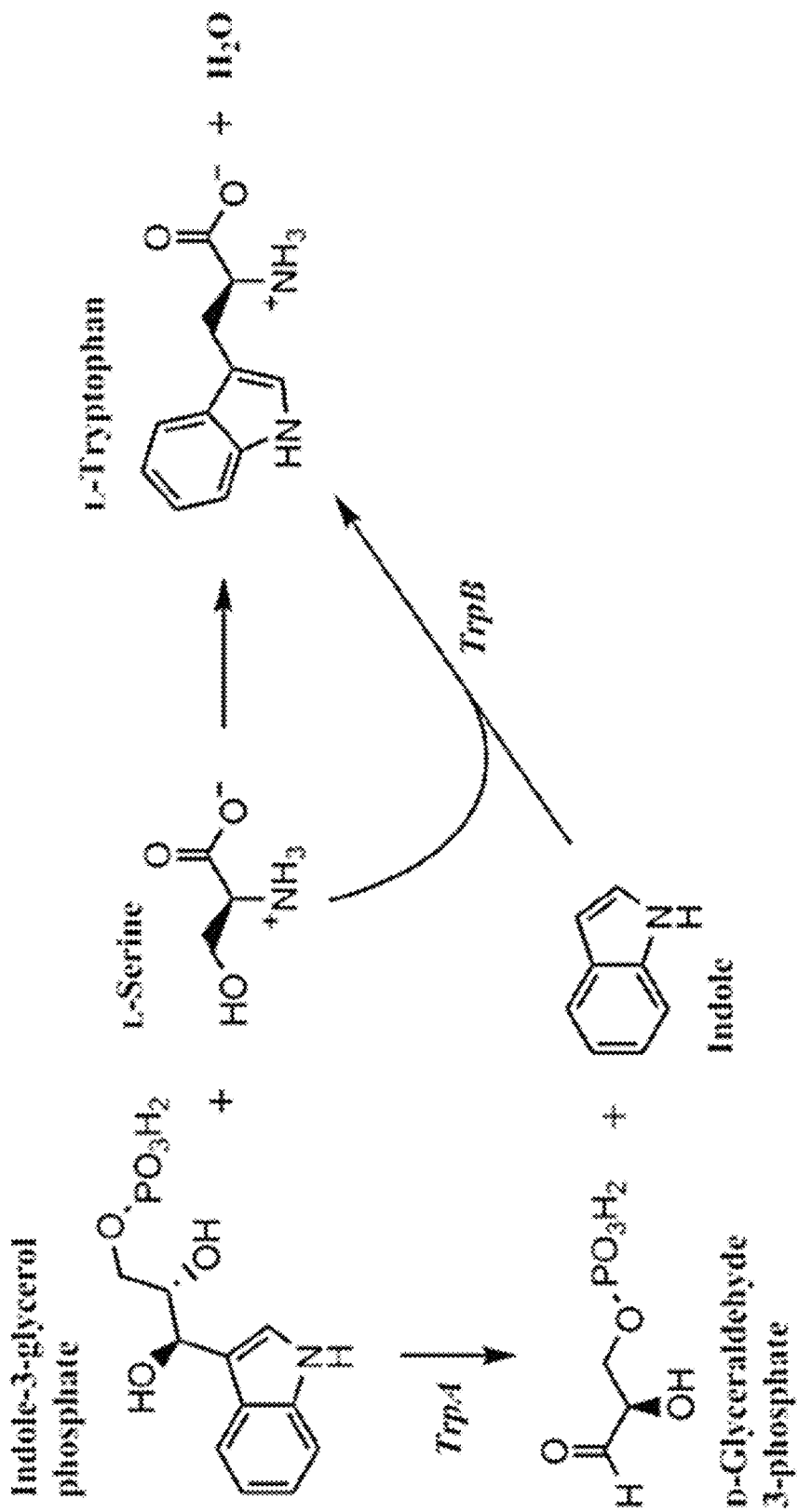
FIG. 1A shows the last two steps in the biosynthesis of L-Trp catalyzed by the multi-enzyme complex tryptophan synthase. IGP is cleaved into G3P and indole by TrpA. The latter serves as nucleophile in the TrpB-catalyzed replacement reaction of the L-Ser hydroxyl to give L-Trp. G3P and water are released as side products of the overall reaction.
Figure 1B:
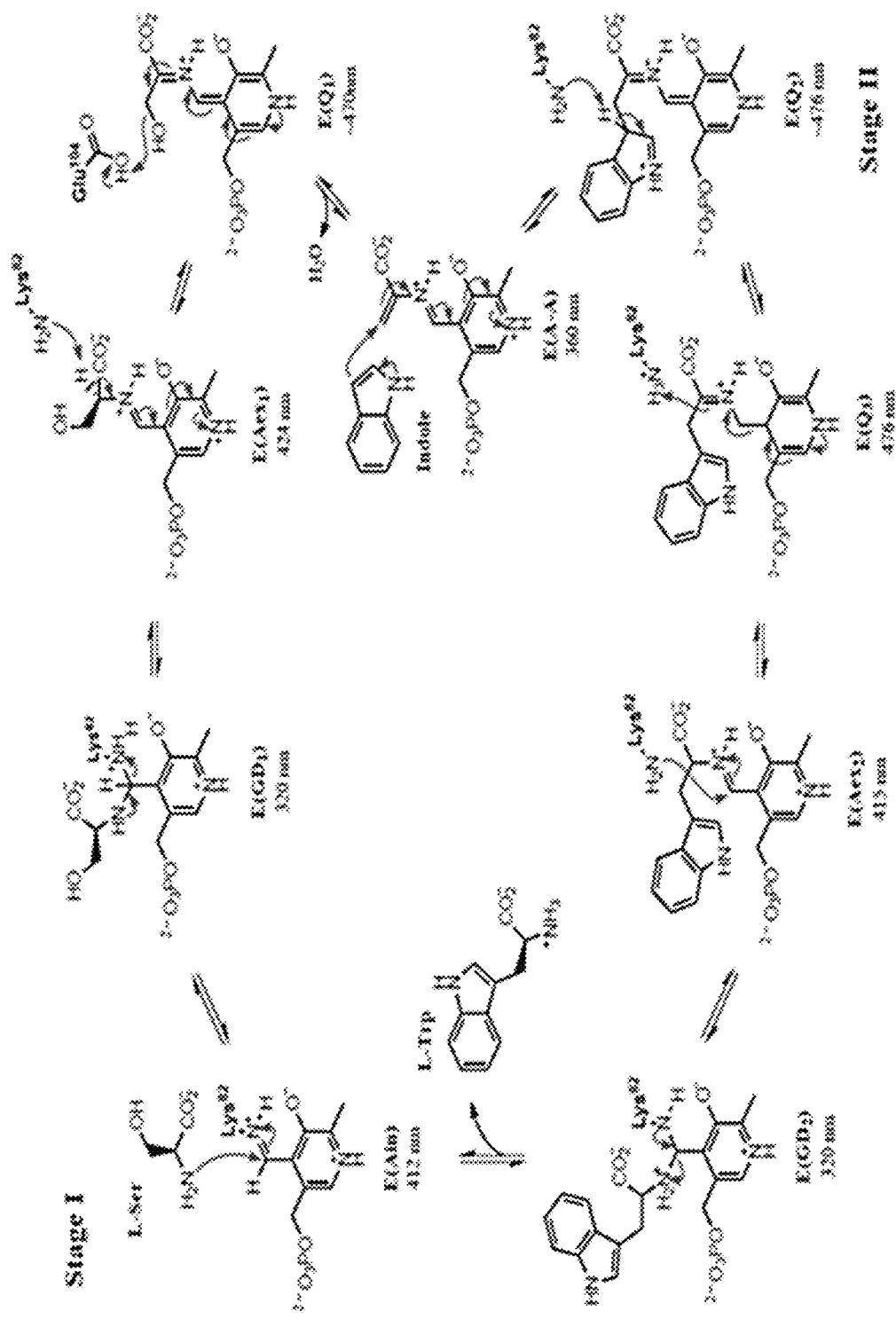
FIG. 1B shows a depiction of the mechanism of the β-replacement reaction in tryptophan synthase divided into α, β-elimination of L-Ser (stage I) and nucleophilic addition of indole (stage II). The wavelengths beneath each intermediate belong to maximum absorbances observed in TrpB from *E. coli* and *S. typhimurium*.
Figure 3A:
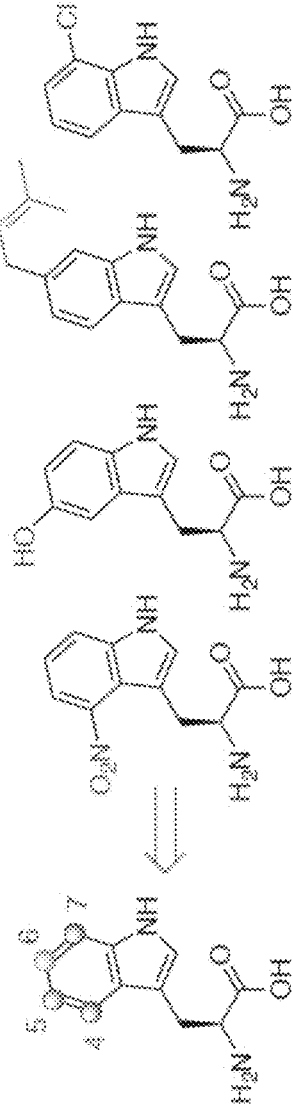
FIG. 3A-C shows the synthesis of Trp analogs. (A) Shows examples of biosynthetic intermediates derived from Trp. (B) Shows previous synthetic methods using enzymes. (C) Shows an alternative biocatalytic route based on TrpB. Ac=acetyl.
Figure 3B:
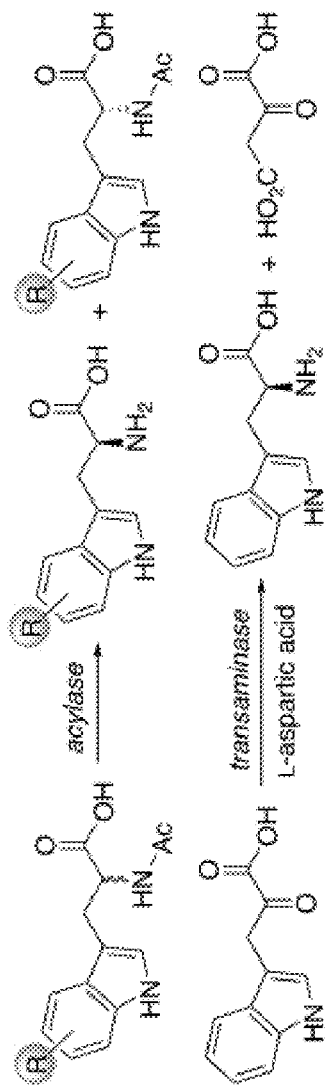
Figure 3C:
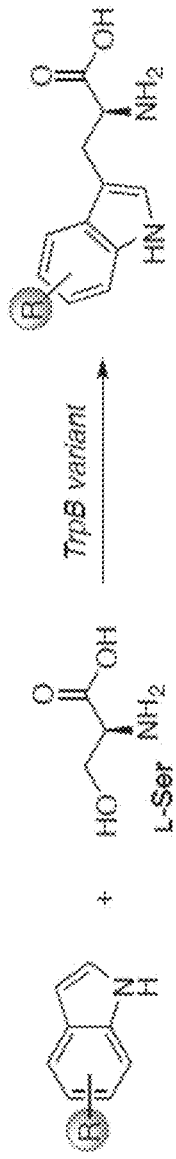

Enzymes such as acylases and transaminases (FIG. 3B) have been applied to synthesis of tryptophan analogs, but in these approaches, the majority of the product must be assembled in advance, with the enzymes mostly serving to set the stereochemistry at the end. Many methods, such as those that use esterases, rely on kinetic resolution, which limits the maximum theoretical yield of product to 50%. A notable exception is the use of tryptophan synthase (TrpS), which can assemble Trp analogs from L-serine (Ser) and the corresponding indole analog with retention of enantiopurity (FIG. 3c).

TrpS is a naturally promiscuous enzyme complex catalyzing β-substitution reaction with most haloindoles, methylindoles, and aminoindoles, along with an assortment of nonindole nucleophiles for C—S and C—N bond formation. Such noncanonical amino acids (NCAAs) have diverse applications in chemical biology, serve as intermediates in the synthesis of natural products, and are privileged scaffolds for the development of pharmaceuticals. Despite its natural ability to produce these desirable compounds, TrpS has enjoyed only limited application. Optimized methods are restricted by low substrate concentrations and yields typically below 50%. To produce NCAAs, researchers have used the *S. typhimurium* TrpS complex (StTrpS), which suffers from poor thermostability and low tolerance to organic solvents.

Tryptophan synthase is typically found as a bi-enzyme complex linearly arranged. In *S. typhimurium*, the smaller α-subunit (27 kDa) adopts a TIM β/α barrel. The PLP-dependent β-subunit (43 kDa) is of a fold type II conformation and features a monovalent cation-binding site adjacent to its catalytic center. The active sites of the subunits are interconnected by a substrate tunnel for efficient channeling of the common metabolite, indole. A great degree of allosteric regulation by an intricate network of interactions is necessary to synchronize the catalytic activities in the spatially separated active sites of the tryptophan synthase complex. A variety of analytical tools have been sought out to gain a more detailed mechanical and chemical understanding of the allosteric regulation mechanisms involved in catalysis, including biochemical solution experiments, mutational studies, and X-ray crystallography. The most essential feature allowing for the high enzymatic efficiency of tryptophan synthase is the direct channeling of the common intermediate, indole, through the hydrophobic 25-Å long substrate tunnel interconnecting the active sites of the subunits. As mentioned tryptophan synthase comprises a polymeric polypeptide of two alpha and two beta subunits referred to as TrpA (tryptophan-α) and TrpB (tryptophan-β) that form an α-ββ-α complex. The α and β subunits have molecular masses of 27 and 43 kDa, respectively. The a subunit has a TIM barrel conformation. The β subunit has a fold type II conformation and a binding site adjacent to the active site for monovalent cations. Their assembly into a complex leads to structural changes in both subunits resulting in reciprocal activation. There are two main mechanisms for intersubunit communication. First, the COMM domain of the β-subunit and the α-loop2 of the α-subunit interact. Additionally, there are interactions between the αGly181 and βSer178 residues. The active sites are regulated allosterically and undergo transitions between open, inactive, and closed, active, states.

Amino acids are organic compounds that form the basis for almost all functional molecules in biological systems. Twenty-one amino acids, which span a wide range of chemical and physical properties, form the basis for the proteins found in all living things. However, nature's repertoire of amino acids extends beyond this set of twenty-one to include the so called non-canonical amino acids (ncAAs), which are not found in proteins, but nonetheless act as signaling molecules and serve as starting materials in both biosynthesis and chemical synthesis.

The interest in non-canonical amino acids (NCAA) has been exponentially growing ever since the possibility of their site-specific introduction into enzymes both in vivo and in vitro through nonsense codon suppression. A large and diverse library of unnatural amino acids (UAAs) has been established to address unresolved questions in protein structure and function with unreached precision. The applications are numerous, including incorporation of biophysical probes, such as fluorescent tags and spin labels, production of "caged" proteins with photoreactive side chains, assessing protein stability, and improving natural enzyme activity.

Furthermore, compounds of peptidic structure are often found in nature and employed in drugs by the pharmaceutical industry. However, chemical synthesis of these substances can be challenging. As part of the green-chemistry movement the enzymatic synthesis of non-canonical peptidic compounds has gained in importance. In addition to the mild conditions and nontoxic reagents, enzymatic reactions often occur with high enantiomeric purity and remarkable rate acceleration.

Tryptophan synthase has also been extensively employed for the enzymatic synthesis of a variety of tryptophan analogues, including methylated, halogenated, and aminated L-tryptophans, dihydroisotryptophan, and selenatryptophan. The common basic approach of the aforementioned cases consists of creating batch reactions of indole analogues and L-Ser catalyzed by native tryptophan synthases.

As used herein an "indole analog" refers to any number of known derivatives of indole as set forth in Formula I:

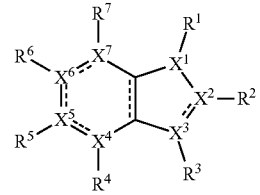

wherein $X_1$-$X_7$ are independently either a carbon, nitrogen, oxygen, or sulfur; $R_1$-$R_7$ are each independently selected from the group consisting of H, —OH, alkyl, aryl, alkoxy, alkenes, alkynes, and substitutions of the foregoing, sulfur-containing group (e.g., thioalkoxy), nitrogen-containing groups (e.g., amide, amino, nitro, azide, and cyano), oxygen-containing group (e.g., ketone, aldehyde, ester, ether, carboxylic acid, and acyl halide), or halogen (e.g., Br, F, iodine). In one embodiment, the indole analog has a structure of Formula II:

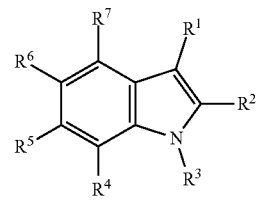

wherein $R_1$-$R_7$ are each independently selected from the group consisting of H, —OH, alkyl, aryl, alkoxy, alkenes, alkynes, and substitutions of the foregoing, sulfur-containing group (e.g., thioalkoxy), nitrogen-containing groups (e.g., amide, amino, nitro, azide, and cyano), oxygen-containing group (e.g., ketone, aldehyde, ester, ether, carboxylic acid, and acyl halide), or halogen (e.g., Br, F, iodine). In one embodiment, the indole analog is selected from the group consisting of:

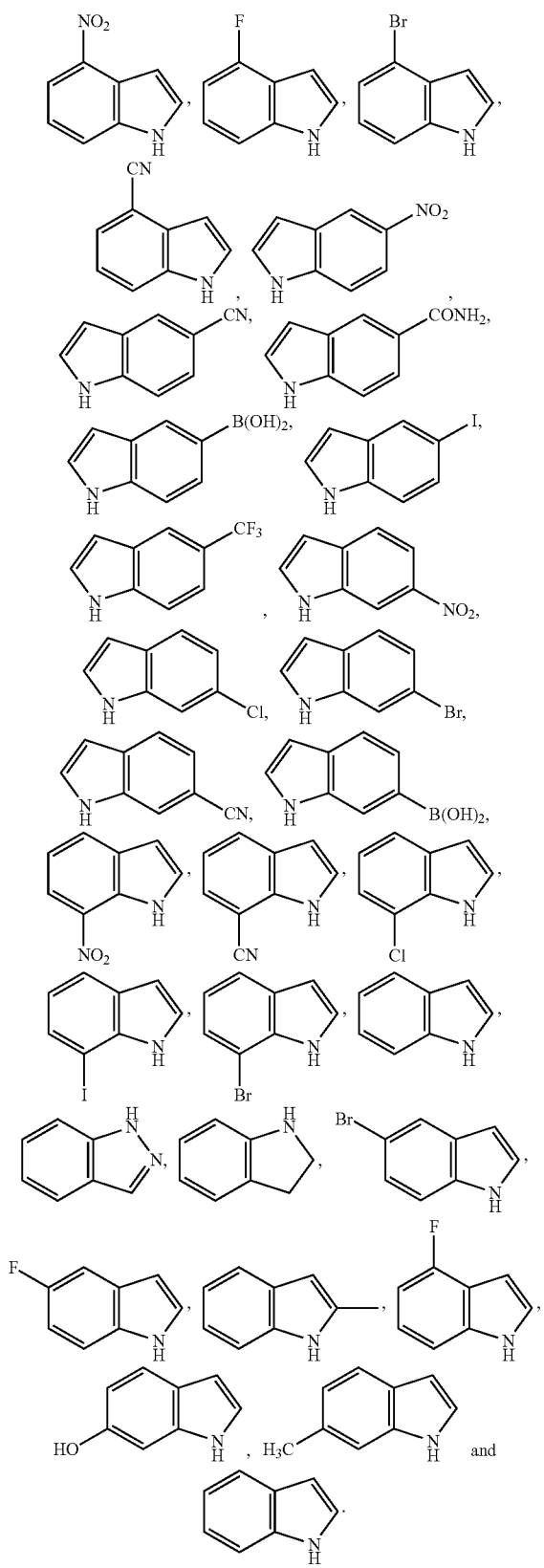

As used herein a "mutant TrpB", "TrpB mutant", "mTrpB" or "engineered TrpB" refers to the β-subunit of tryptophan synthase (TrpS) that has been recombinantly modified to differ from the wild-type sequence. A mutant TrpB typically has a desired substrates specificity, turnover number, product production, stability, etc. that differ from a wild-type enzyme or subunit. A mutant TrpB can be derived from a number of homologs of diverse origin, wherein the mutant TrpB differs from a wild-type of parental polypeptide by one or more (e.g., 2, 3, 4, 5, 6, 7, 8, 9, 10, 15, 20, 25, 30 or more, up to about 50) mutations and wherein the mutant TrpB can generate NCAA. UAA amino acids or other desired chemical entities from an indole analog and a serine or threonine substrate or analog and/or wherein the mutant TrpB functions independent of the TrpA subunit.

A "mutant", "variant" or "modified" protein, enzyme, polynucleotide, gene, or cell, means a protein, enzyme, polynucleotide, gene, or cell, that has been altered or derived, or is in some way different or changed, from a parent protein, enzyme, polynucleotide, gene, or cell. A mutant or modified protein or enzyme is usually, although not necessarily, expressed from a mutant polynucleotide or gene.

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon.

Modified amino acids are amino acids that are chemically modified. Non-limiting examples of a modified amino acid include a glycosylated amino acid, a sulfated amino acid, a prenylated (e.g., farnesylated, geranylgeranylated) amino acid, an acetylated amino acid, an acylated amino acid, a pegylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols on CD-ROM (Humana Press, Towata, N.J.).

A "parent" protein, enzyme, polynucleotide, gene, or cell, is any protein, enzyme, polynucleotide, gene, or cell, from which any other protein, enzyme, polynucleotide, gene, or cell, is derived or made, using any methods, tools or techniques, and whether or not the parent is itself native or mutant. A parent polynucleotide or gene encodes for a parent protein or enzyme.

A "parental polypeptide" refers to a polypeptide used to generate a recombinant or mutant polypeptide. The term "parental polypeptide" describes a polypeptide that occurs in nature, i.e. a "wild-type" cell that has not been genetically modified. The term "parental polypeptide" also describes a polypeptide that serves as the "parent" for further engineering. For example, a wild-type polypeptide can be mutated to have a first mutation or set of mutations that can provide a desired biological activity or be "silent mutations". For example, the wild-type TrpB from *P. furiosus* (SEQ ID NO:2), *A. fulgidus* (SEQ ID NO:4), *T. maritima* (SEQ ID NO:6) or *E. coli* (SEQ ID NO:8) can serve as a parent wild-type polypeptide for mutagenesis. The polypeptide can be mutated to include a first set of mutations (e.g., mutations at 116, E17, 168, F95, F274, T292, T321 and V384) to give rise to mutant PfTrpB2B9 (SEQ ID NO:10). This first mutant polypeptide (e.g., PfTrpB2B9) can then act as a parental polypeptide in the generation of second mutation or set of mutations that can provide a desired biological activity or be silent mutations.

The term "polynucleotide," "nucleic acid" or "recombinant nucleic acid" refers to polynucleotides such as deoxyribonucleic acid (DNA), and, where appropriate, ribonucleic acid (RNA).

A "protein" or "polypeptide", which terms are used interchangeably herein, comprises one or more chains of chemical building blocks called amino acids that are linked together by chemical bonds called peptide bonds. A protein or polypeptide can function as an enzyme. An "enzyme" means any substance, composed wholly or largely of protein, that catalyzes or promotes, more or less specifically, one or more chemical or biochemical reactions.

As used herein "TrpB" refers to a diverse set of homologs of the β-subunit of tryptophan synthase. A wild-type TrpB can be used as a parental polypeptide for mutation. For example, the TrpB from *Pyroccous furiosus* (PfTrpB) is used as a reference sequence in the disclosure and comprises or consists of the sequence as set forth in SEQ ID NO:2. Homologs of PfTrpB are known and include, for example, TrpB from *Archaeoglobus fulgidus* (Af), which has 72% sequence identity to PfTrpB, and TrpB from *Escherichia coli* (Ec), which has 57% sequence identity to PfTrpB. Accordingly, wild-type TrpB sequences having at least 57% sequence identity to SEQ ID NO:2 can be used as a parental polypeptide for mutations to form mutant TrpB. The disclosure demonstrates that a diverse set of TrpB homologs based on a phylogenetic analysis of TrpB, including *Archaeoglobus fulgidus* (AfTrpB, 72% sequence identity), *Thermotoga maritima* (TmTrpB, 64%), and *Escherichia coli* (EcTrpB, 57%) are useful in obtaining desirable mutant TrpBs. A multiple-sequence alignment with PfTrpB is shown in FIG. 2.

The engineered/mutant tryptophan beta-subunits (TrpBs) described throughout the disclosure were acquired by accumulating point mutations in directed evolution experiments from a parental polypeptide. An alternative method for making libraries for directed evolution to obtain modified TrpBs with new or altered properties is recombination, or chimeragenesis, in which portions of homologous TrpBs are swapped to form functional chimeras. Therefore, the amino acid mutations made in this way are less disruptive, on average, than random mutations. A structure-based algorithm, such as SCHEMA, identifies fragments of proteins that can be recombined to minimize disruptive interactions that would prevent the protein from folding into its active form.

Provided herein are variants of TrpB that catalyze the synthesis of NCAAs and UAAs. The reaction uses indole analogs and L-serine or L-threonine or analogs thereof.

The term "total turnover number" (TTN) is the total number of substrate molecules converted to product (or turned over) by an enzyme over its lifetime or during a specified time period. TTN is an important figure of merit for a catalyst because it allows for the calculation of the total amount of product that can be made from a given quantity of catalyst.

The modified TrpB subunits used as catalyst can, in some instances, function at ambient temperature or higher (e.g., from 20° C. to 95° C., typically about 75° C.) and ambient pressure.

The mutant TrpBs of the disclosure have enormous potential for applications in drug discovery, chemical synthesis, pharmaceutical preparations, and biotechnology. However, tailoring TrpBs to accept nonnatural substrates, as required by many applications, is difficult in this catalytic system, which involves multiple subunits having allosteric interactions. Compared to their natural counterparts, engineered/mutant TrpBs of the disclosure have improved catalytic and coupling efficiencies.

The phrase "TrpB activity" refers to the biological activity of TrpB or mutants thereof. For example, TrpB activity includes the ability of the TrpB polypeptide to produce NCAAs or UAAs from an indole or derivative thereof and L-serine or L-threonine. A mTrpB activity includes the ability to produce, in one embodiment, a 4-, 5-, 6- and/or 7-position substituted tryptophan analog from a 4-, 5-, 6- and/or 7-position substituted indole analog and L-serine (Ser).

The term "substrate" or "suitable substrate" means any substance or compound that is converted or meant to be converted into another compound by the action of an enzyme catalyst. The term includes indole and indole derivatives as well as serine or threonine and derivatives thereof.

As will be described in more detail below, the disclosure is based, at least in part, on the generation and expression of novel enzymes that catalyze the conversion of indole or indole derivatives and serine or threonine to NCAAs, UAAs and other chemical entities. In one embodiment, polypeptides have been engineered to convert an indole and serine or threonine to an NCAA, UAA or other chemical. For example, 4-nitroindole can be used in the production of chemical entities when reacted with a TrpB variant of the disclosure (see, e.g., scheme 1). Because the nitro substituent on the 4-nitroindole creates a steric impediment to substrate binding, and also withdraws electron density from the indole moiety, the reaction provides for the production of 4-nitrotryptophan. Since the indole is a nucleophile in this reaction manifold, electron withdrawing substituents are intrinsically deactivating. The compound 4-nitroTrp is a biosynthetic and chemical precursor to thaxtomin A, a potentially useful agrochemical. Additionally, 4-nitroTrp is a chemical precursor to the tumor-promoter indolactam V (see, Table A).

Scheme 1:

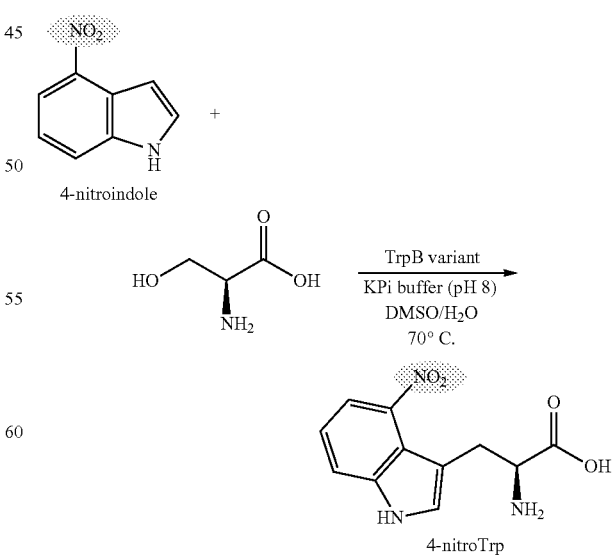

KPi = potassium phosphate

TABLE A

Products synthesized from 4-nitroTrp

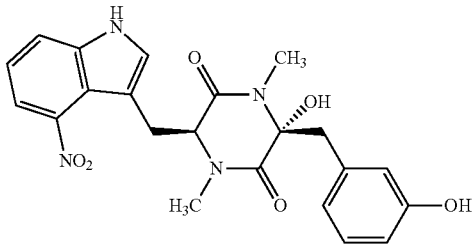

thaxtomin A

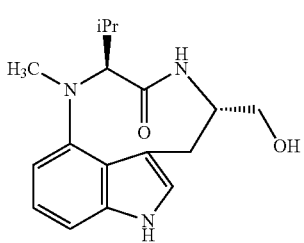

Indolactam V

While the TrpB mutants will be described in more detail below, it is understood that polypeptides of the disclosure may contain one or more modified amino acids. Amino acid(s) are modified, for example, co-translationally or post-translationally during recombinant production (e.g., N-linked glycosylation at N—X—S/T motifs during expression in mammalian cells) or modified by synthetic means.

The disclosure demonstrates the engineering of TrpB through directed evolution to provide a β-subunit that has biological activity independent of TrpA and which can produce tryptophan and/or NCAAs, UAAs or other chemical entities from suitable substrates. For example, the evolution of TrpB into TrpB-mutants shows that members of the TrpB family can be evolved by point mutations and screening for function on various substrates and various products production.

Referring to the sequence comparison of various TrpB subunits in FIG. 2, SEQ ID NO:2 includes the amino acid sequence of TrpB isolated from *Pyroccocus furiosus* designated PfTrpB. SEQ ID NO:4 provides the amino acid sequence of wild-type TrpB from *Archaeoglobus fulgidus*. This wild-type TrpB designated AfTrpB shares 72% amino acid sequence identity to PfTrpB (SEQ ID NO:2). SEQ ID NO:6 includes the amino acid sequence of wild-type TrpB from *Thermotoga maritima*. This wild-type TrpB is designated TmTrpB and shares 64% amino acid sequence identity to PfTrpB (SEQ ID NO:2). SEQ ID NO:8 includes the amino acid sequence of wild-type TrpB from *Escherichia coli*. This wild-type TrpB is designated EcTrpB and shares 57% amino acid sequence identity to PfTrpB (SEQ ID NO:2).

The TrpBs set forth in SEQ ID NOs:2, 4, 6, and 8 are closely related to one another and show a high degree of sequence identity and activity. The sequences can be aligned and conserved amino acids identified based upon the alignment. The alignment provided in FIG. 2 identifies "equivalent positions" in the sequences. An equivalent position denotes a position which, on the basis of the alignment of the sequence of the parent TrpB in question with the "reference" TrpB amino acid sequence in question (e.g. SEQ ID NO: 2) so as to achieve juxtapositioning of amino acid residues which are common to both, corresponds most closely to a particular position in the reference sequence in question. This process can cause gaps or insertions to appear in the sequences. In the alignment of FIG. 2, equivalent positions are shown lined up vertically with one another. For example, position 47 in SEQ ID NO: 2 is equivalent or corresponds to position 60 in SEQ ID NO: 4 and position 49 in SEQ ID NO: 6 and position 53 in SEQ ID NO:8.

Provided herein are engineered mutant TrpB polypeptides capable of producing NCAAs, UAAs and chemical entities. Protein engineering of TrpBs from other sources can be expected to lead to a similar result using the basic alignment and mutation tools described herein. It is well known in the art that amino acid substitutions having a particular effect (e.g. that confer activity toward a new substrate) can have the same effect in closely related proteins. For example, the alignment of the four homologs illustrates the high degree of sequence similarity among the four TrpBs (see, FIG. 2). Moreover, it will be readily apparent based upon the "mutation" row, which exemplary mutations can be and have been made. It has been shown on multiple occasions that amino acid substitutions at equivalent positions in these enzymes have equivalent effects on function. For example, the substitution of M144T and N166D in PfTrpB increases the $k_{cat}$ by at least 2-fold. The same substitution of the equivalent position in AfTrpB, TmTrpB, and EcTrpB, which is M156T/N178D, M145T/N167D, and M149T/N171D (respectively), has the same effect. Additionally, these TrpB polypeptides can be subjected to rounds of directed evolution using the techniques and screens described herein to obtain and/or increase substrate specificity and product generation.

Accordingly, in one embodiment, a mutant TrpB polypeptide is provided that comprises at least 57% identity to SEQ ID NO:2 and comprises activating mutations at positions 16, 17, 68, 95, 139, 212, 274, 292, 321 and 384 of SEQ ID NO:2 or positions in SEQ ID NO:4 (positions 29, 30, 80, 107, 151, 224, 285, 303, 332, and 395), 6 (positions 18, 19, 69, 96, 140, 213, 274, 292, and 381) or 8 (positions 22, 23, 73, 100, 144, 217, 279, 326, and 390), which correspond to the positions in SEQ ID NO:2. In one embodiment, the activating mutations are an I16V, E17G, I68V, F95L, M139L, L212P, F274S, T292S, T321A, V384A mutations with respect to SEQ ID NO:2 (I29V, P30V, I80V, F107L, M151L, I224P, L285S, T303S, T332A, and R395A for SEQ ID NO:4; M18V, P19G, I69V, K96L, P140L, L213P, L274S, T292S, and H381A for SEQ ID NO:6; and M22V, P23G, L73V, R100L, P144L, L217P, Y279S, S326A, and I390A for SEQ ID NO:8). In another embodiment, the mutant TrpB can include 50, 25, 10, 5 or fewer conservative substitutions in addition to the specific mutations above.

In another embodiment, the mutant TrpB can comprise one or more additional mutations that improve activity. These mutations are selected from the group consisting of mutations at residues 104, 165, 166, 183, 186, 301 and any combination thereof of SEQ ID NO:2; residues 116, 177, 178, 195, 198, 312 and any combination there of SEQ ID NO:4; residues 105, 166, 167, 184, 187, 301 and any combination thereof of SEQ ID NO:6; and residues 109, 170, 171, 188, 306 and any combination thereof of SEQ ID NO:8. In another embodiment, the mutant TrpB can comprise one or more additional mutations selected from the group consisting of E104G or E104A, Y165F, N166D, I183F, V186A, Y301H and any combination thereof of SEQ ID NO:2; residues E116G or E116A, Y177F, N178D, I195F, V198A, Y312H and any combination there of SEQ ID NO:4; residues E105G or E105A, Y166F, N167D, I184F, V187A, Y301H and any combination thereof of SEQ ID NO:6; and residues E109G or E109A, C165F, N171D, L188F, F306H and any combination thereof of SEQ ID NO:8.

In yet another embodiment, a mutant TrpB polypeptide is provided that comprises SEQ ID NO:2 and has at least 50, 25, 10, 5 or fewer conservative substitutions or has about 57% or more identity to SEQ ID NO:2 and has activating mutations at positions 16, 17, 68, 95, 139, 212, 274, 292, 321 and 384. In one embodiment, the activating mutations are an I16V, E17G, I68V, F95L, M139L, L212P, F274S, T292S, T321A, V384A. In a further embodiment, the mutant TrpB polypeptide comprises one or more additional mutations that improve activity. These mutations are selected from the group consisting of mutations at residues 104, 166, 183, 186 and any combination thereof of SEQ ID NO:2. In a further embodiment, the mutant TrpB can comprise one or more additional mutations selected from the group consisting of E104G or E014A, N166D, I183F, V186A and any combination thereof of SEQ ID NO:2.

In yet another embodiment, a mutant TrpB polypeptide is provided that comprises SEQ ID NO:4 and has at least 50, 25, 10, 5 or fewer conservative substitutions or has about 57% or more identity to SEQ ID NO:4 and has activating mutations at positions 29, 30, 80, 107, 151, 224, 285, 303, 332, and 395. In one embodiment, the activating mutations are an I29V, P30V, I80V, F107L, M151L, I224P, L285S, T303S, T332A, and R395A. In a further embodiment, the mutant TrpB polypeptide comprises one or more additional mutations that improve activity. These mutations are selected from the group consisting of mutations at residues 116, 178, 195, 198 and any combination thereof of SEQ ID NO:4. In a further embodiment, the mutant TrpB can comprise one or more addition mutations selected from the group consisting of E116G, N178D, I195F, V198A and any combination thereof of SEQ ID NO:4.

In yet another embodiment, a mutant TrpB polypeptide is provided that comprises SEQ ID NO:6 and has at least 50, 25, 10, 5 or fewer conservative substitutions or has about 57% or more identity to SEQ ID NO:6 and has activating mutations at positions 18, 19, 69, 96, 140, 213, 274, 292, and 381. In one embodiment, the activating mutations are an M18V, P19G, I69V, K96L, P140L, L213P, L274S, T292S, and H381A. In a further embodiment, the mutant TrpB polypeptide comprises one or more additional mutations that improve activity. These mutations are selected from the group consisting of mutations at residues 105, 167, 184, 187 and any combination thereof of SEQ ID NO:6. In a further embodiment, the mutant TrpB can comprise one or more addition mutations selected from the group consisting of E105G, N167D, I184F, V187A and any combination thereof of SEQ ID NO:6.

In yet another embodiment, a mutant TrpB polypeptide is provided that comprises SEQ ID NO:8 and has at least 50, 25, 10, 5 or fewer conservative substitutions or has about 57% or more identity to SEQ ID NO:8 and has activating mutations at positions 22, 23, 73, 100, 144, 217, 279, 326, and 390. In one embodiment, the activating mutations are an M22V, P23G, L73V, R100L, P144L, L217P, Y279S, S326A, and I390A. In a further embodiment, the mutant TrpB polypeptide comprises one or more additional mutations that improve activity. These mutations are selected from the group consisting of mutations at residues 109, 171, 188 and any combination thereof of SEQ ID NO:8. In a further embodiment, the mutant TrpB can comprise one or more addition mutations selected from the group consisting of E109G, N171D, L188F and any combination thereof of SEQ ID NO:8.

In yet another embodiment, a mutant TrpB polypeptide is provided that comprises SEQ ID NO:2 and has at least 50, 25, 10, 5 or fewer conservative substitutions or has about 57%, 60%, 70%, 80%, 85%, 90%, 95%, 98%, or 99% or more identity to SEQ ID NO:2 and has activating mutations at positions 16, 17, 68, 95, 104, 139, 166, 183, 186, 212, 274, 292, 321 and 384. In one embodiment, the activating mutations are an I16V, E17G, I68V, F95L, E104G (or E104A), M139L, N166D, I183F, V186A, L212P, F274S, T292S, T321A, and V384A. In yet another embodiment, a mutant TrpB polypeptide is provided that has or consists of the sequence of SEQ ID NO:2, but has the following mutations: I16V, E17G, I68V, F95L, E104G (or E104A), M139L, N166D, I183F, V186A, L212P, F274S, T292S, T321A, and V384A.

In yet another embodiment, a mutant TrpB polypeptide is provided that comprises SEQ ID NO:4 and has at least 50, 25, 10, 5 or fewer conservative substitutions or has about 57%, 60%, 70%, 80%, 85%, 90%, 95%, 98%, or 99% or more identity to SEQ ID NO:4 and has activating mutations at positions 29, 30, 80, 107, 116, 151, 178, 195, 198, 224, 285, 303, 332, and 395. In one embodiment, the activating mutations are an I29V, P30V, I80V, F107L, E116G (or E116A), M151L, N178D, I195F, V198A, I224P, L285S, T303S, T332A, and R395A. In yet another embodiment, a mutant TrpB polypeptide is provided that has or consists of the sequence of SEQ ID NO:4, but has the following mutations: I29V, P30V, I80V, F107L, E116G (or E116A), M151L, N178D, I195F, V198A, I224P, L285S, T303S, T332A, and R395A.

In yet another embodiment, a mutant TrpB polypeptide is provided that comprises SEQ ID NO:6 and has at least 50, 25, 10, 5 or fewer conservative substitutions or has about 57%, 60%, 70%, 80%, 85%, 90%, 95%, 98%, or 99% or more identity to SEQ ID NO:6 and has activating mutations at positions 18, 19, 69, 96, 105, 140, 167, 184, 187, 213, 274, 292, and 381. In one embodiment, the activating mutations are an M18V, P19G, I69V, K96L, E105G (or E105A), P140L, N167D, I184F, V187A, L213P, L274S, T292S, and H381A. In yet another embodiment, a mutant TrpB polypeptide is provided that has or consists of the sequence of SEQ ID NO:6, but has the following mutations: M18V, P19G, I69V, K96L, E105G (or E105A), P140L, N167D, I184F, V187A, L213P, L274S, T292S, and H381A.

In yet another embodiment, a mutant TrpB polypeptide is provided that comprises SEQ ID NO:8 and has at least 50, 25, 10, 5 or fewer conservative substitutions or has about 57%, 60%, 70%, 80%, 85%, 90%, 95%, 98%, or 99% or more identity to SEQ ID NO:8 and has activating mutations at positions 22, 23, 73, 100, 109, 144, 171, 188, 217, 279, 326, and 390. In one embodiment, the activating mutations are an M22V, P23G, L73V, R100L, E109G (or E109A), P144L, N171D, L188F, L217P, Y279S, S326A, and I390A. In yet another embodiment, a mutant TrpB polypeptide is provided that has or consists of the sequence of SEQ ID NO:8, but has the following mutations: M22V, P23G, L73V, R100L, E109G (or E109A), P144L, N171D, L188F, L217P, Y279S, S326A, and I390A.

"Conservative amino acid substitution" or, simply, "conservative variations" of a particular sequence refers to the replacement of one amino acid, or series of amino acids, with essentially identical amino acid sequences. One of skill will recognize that individual substitutions, deletions, or additions which alter, add, or delete a single amino acid or a percentage of amino acids in an encoded sequence result in "conservative variations" where the alterations result in the deletion of an amino acid, addition of an amino acid, or substitution of an amino acid with a chemically similar amino acid.

Conservative substitution tables providing functionally similar amino acids are well known in the art. For example, one conservative substitution group includes Alanine (A), Serine (S), and Threonine (T). Another conservative substitution group includes Aspartic acid (D) and Glutamic acid (E). Another conservative substitution group includes Asparagine (N) and Glutamine (Q). Yet another conservative substitution group includes Arginine (R) and Lysine (K). Another conservative substitution group includes Isoleucine, (I) Leucine (L), Methionine (M), and Valine (V). Another conservative substitution group includes Phenylalanine (F), Tyrosine (Y), and Tryptophan (W).

Thus, "conservative amino acid substitutions" of a listed polypeptide sequence (e.g., SEQ ID NOs: 2, 4, 6, or 8) include substitutions of a percentage, typically less than 10%, of the amino acids of the polypeptide sequence, with a conservatively selected amino acid of the same conservative substitution group. Accordingly, a conservatively substituted variation of a polypeptide of the disclosure can contain 100, 75, 50, 25, or 10 substitutions with a conservatively substituted variation of the same conservative substitution group.

It is understood that the addition of sequences which do not alter the encoded activity of a nucleic acid molecule, such as the addition of a non-functional or non-coding sequence, is a conservative variation of the basic nucleic acid. One of skill in the art will appreciate that many conservative variations of the nucleic acid constructs, which are disclosed, yield a functionally identical construct. For example, owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the polypeptides provided herein.

The "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., concentration or weight), or in terms of affinity or dissociation constants. As used interchangeably herein a "TrpB mutant activity", "mutant TrpB activity", "biological activity of TrpB mutant" or "functional activity of TrpB mutant", refers to an activity exerted by a TrpB mutant polypeptide of the disclosure on a TrpB substrate, as determined in vivo or in vitro, according to standard techniques. The biological activity of TrpB mutants is described herein as, for example, the ability to utilize indole or analogs thereof and L-serine or L-threonine in the generation of NCAAs, UAAs or other desired chemical entities. Other measurements are described in the examples below.

It will be appreciated by those skilled in the art that due to the degeneracy of the genetic code, a multitude of nucleotide sequences encoding mutant TrpBs of the disclosure may be produced, some of which bear substantial identity to the nucleic acid sequences explicitly disclosed herein (e.g., SEQ ID NO:1, 3, 5, or 7). For instance, codons AGA, AGG, CGA, CGC, CGG, and CGU all encode the amino acid arginine. Thus, at every position in the nucleic acids of the disclosure where an arginine is specified by a codon, the codon can be altered to any of the corresponding codons described above without altering the encoded polypeptide. It is understood that U in an RNA sequence corresponds to T in a DNA sequence.

"Conservative variants" are proteins or enzymes in which a given amino acid residue has been changed without altering overall conformation and function of the protein or enzyme, including, but not limited to, replacement of an amino acid with one having similar properties, including polar or non-polar character, size, shape, and charge. Amino acids other than those indicated as conserved may differ in a protein or enzyme so that the percent protein or amino acid sequence similarity between any two proteins of similar function may vary and can be, for example, at least 30%, at least 50%, at least 70%, at least 80%, at least 90%, at least 95%, at least 98%, or at least 99%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that result in the highest sequence similarity.

"Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that result in the highest sequence similarity. For example, the "identity" or "percent identity" with respect to a particular pair of aligned amino acid sequences can refer to the percent amino acid sequence identity that is obtained by ClustalW analysis (version W 1.8 available from European Bioinformatics Institute, Cambridge, UK), counting the number of identical matches in the alignment and dividing such number of identical matches by the greater of (i) the length of the aligned sequences, and (ii) 96, and using the following default ClustalW parameters to achieve slow/accurate pairwise alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins" in "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Nat'l. Acad. Sci. USA 89: 10915-10919 (each of which is incorporated by reference). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm, e.g., gapped BLAST 2.0, described in Altschul et al. (1997) Nucl. Acids Res. 25: 3389-3402 (incorporated by reference herein), and made available to the public at the National Center for Biotechnology Information (NCBI) Website. Optimal alignments, including multiple alignments, can be prepared using, e.g., PSI-BLAST, available through the NCB1 website and described by Altschul et al. (1997) Nucl. Acids Res. 25:3389-3402 (incorporated by reference herein).

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. For example, in SEQ ID NO:2, position 12 is P, position 13 is E, etc. When a test sequence is optimally aligned with SEQ ID NO:2, a residue in the test sequence that aligns with the P at position 12 is said to "correspond to position 12" of SEQ ID NO:2. Owing to deletions, insertion, truncations, fusions, etc., that must be taken into account when determining an optimal alignment, in general the amino acid residue number in a test sequence as determined by simply counting from the N-terminal end will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

Non-conservative modifications of a particular polypeptide are those, which substitute any amino acid not characterized as a conservative substitution. For example, any substitution which crosses the bounds of the six groups set forth above. These include substitutions of basic or acidic amino acids for neutral amino acids, (e.g., Asp, Glu, Asn, or Gln for Val, Ile, Leu or Met), aromatic amino acid for basic or acidic amino acids (e.g., Phe, Tyr or Trp for Asp, Asn, Glu or Gln) or any other substitution not replacing an amino acid with a like amino acid. Basic side chains include lysine (K), arginine (R), histidine (H); acidic side chains include aspartic acid (D), glutamic acid (E); uncharged polar side chains include glycine (G), asparagine (N), glutamine (Q), serine (S), threonine (T), tyrosine (Y), cysteine (C); nonpolar side chains include alanine (A), valine (V), leucine (L), isoleucine (I), proline (P), phenylalanine (F), methionine (M), tryptophan (W); beta-branched side chains include threonine (T), valine (V), isoleucine (I); aromatic side chains include tyrosine (Y), phenylalanine (F), tryptophan (W), histidine (H).

Accordingly, some amino acid residues at specific positions in a polypeptide are "excluded" from conservative amino acid substitutions. Instead, these restricted amino acids are generally chosen from a specific group or selected amino acids or are not substituted or mutated at all. For example, with reference to FIG. 2, the line indicated as "Mutations" are positions that include specific and/or non-conservative mutations.

A polynucleotide, polypeptide, or other component is "isolated" or "purified" when it is partially or completely separated from components with which it is normally associated (other proteins, nucleic acids, cells, synthetic reagents, etc.). A nucleic acid or polypeptide is "recombinant" when it is artificial or engineered, or derived from an artificial or engineered protein or nucleic acid through the process of mutation. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant or engineered mutant of a naturally occurring gene, is recombinant. For example, an "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Typically, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

The disclosure envisions multi-unit polypeptides. Such a multi-unit polypeptide would comprise for example: TrpA-mTrpB-mTrpB-TrpA. The tryptophan-α (TrpA) domain (and sequences thereof) of TrpS for each of *Pyrococcus furiosus, Archaeoglobus fulgidus, Thermotoga maritima*, and *Escherichia coli* are well known in the art.

In other embodiments, isolated nucleic acid molecules are provided. In one embodiment, the disclosure provides a novel family of isolated or recombinant polynucleotides referred to herein as "TrpB mutant polynucleotides" or "TrpB mutant nucleic acid molecules." TrpB mutant polynucleotide sequences are characterized by the ability to encode a TrpB mutant polypeptide. In general, the disclosure includes any nucleotide sequence that encodes any of the TrpB mutant polypeptides described herein. In some aspects of the disclosure, a TrpB mutant polynucleotide that encodes a TrpB mutant polypeptide with TrpB mutant activity is provided. The terms "polynucleotide," "nucleotide sequence," and "nucleic acid molecule" are used to refer to a polymer of nucleotides (A, C, T or U, G, etc. or naturally occurring or artificial nucleotide analogues), e.g., DNA or RNA, or a representation thereof, e.g., a character string, etc., depending on the relevant context. A given polynucleotide or complementary polynucleotide can be determined from any specified nucleotide sequence.

In one embodiment, the TrpB mutant polynucleotides comprise recombinant or isolated forms of naturally occurring nucleic acids isolated from an organism, which have been mutated by, for example, directed evolution. Exemplary TrpB polynucleotides include those that encode the wild-type polypeptides set forth in SEQ ID NO: 2, 4, 6, or 8. In another aspect of the disclosure, TrpB mutant polynucleotides are produced by diversifying, e.g., recombining and/or mutating one or more naturally occurring, isolated, or recombinant TrpB polynucleotides. As described in more detail elsewhere herein, it is often possible to generate diversified TrpB mutant polynucleotides encoding TrpB mutant polypeptides with superior functional attributes, e.g., increased catalytic function, increased stability, novel substrate or product production, or higher expression level, than a TrpB polynucleotide used as a substrate or parent in the diversification process.

The polynucleotides of the disclosure have a variety of uses in, for example, recombinant production (i.e., expression) of the TrpB mutant polypeptides of the disclosure and as substrates for further diversity generation, e.g., recombination reactions or mutation reactions to produce new and/or improved TrpB mutant homologues, and the like.

It is important to note that certain specific, substantial, and credible utilities of TrpB mutant polynucleotides do not require that the polynucleotide encodes a polypeptide with substantial TrpB mutant activity or even TrpB mutant activity. For example, TrpB mutant polynucleotides that do not encode active enzymes can be valuable sources of parental polynucleotides for use in diversification procedures to arrive at TrpB mutant polynucleotide with desirable functional properties (e.g., high $k_{cat}$ or $k_{cat}/K_m$, low $K_m$, high stability toward heat or other environmental factors, high transcription or translation rates, resistance to proteolytic cleavage, etc.).

TrpB mutant polynucleotides, including nucleotide sequences that encode TrpB polypeptides and variants thereof, fragments of TrpB mutant polypeptides, related fusion proteins, or functional equivalents thereof, are used in recombinant DNA molecules that direct the expression of the TrpB mutant polypeptides in appropriate host cells, such as bacterial cells. Due to the inherent degeneracy of the genetic code, other nucleic acid sequences which encode substantially the same or a functionally equivalent amino acid sequence can also be used to clone and express the TrpB mutant polynucleotides.

The term "host cell", as used herein, includes any cell type which is susceptible to transformation with a nucleic acid construct. The term "transformation" means the introduction of a foreign (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may include regulatory or control sequences, such as start, stop, promoter, signal, secretion, or other sequences used by the genetic machinery of the cell. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang et al. (1991) Gene 105:61-72; incorporated by reference herein). Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508; incorporated by reference herein) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for S. cerevisiae and mammals are UAA and UGA, respectively. The preferred stop codon for monocotyledonous plants is UGA, whereas insects and E. coli prefer to use UAA as the stop codon (Dalphin et al. (1996) Nucl. Acids Res. 24: 216-218; incorporated by reference herein). Methodology for optimizing a nucleotide sequence for expression in a plant is provided, for example, in U.S. Pat. No. 6,015,891, and the references cited therein (incorporated herein by reference).

In some embodiments, nucleic acid molecules of the disclosure include: (a) a nucleic acid molecule which encodes a polypeptide comprising the amino acid sequence selected from the group consisting of SEQ ID NO:10, 12, 14, 16, 18, 20, 22, 24, and 26; (b) a nucleic acid molecule which encodes a polypeptide consisting of the amino acid sequence selected from the group consisting of SEQ ID NO: 10, 12, 14, 16, 18, 20, 22, 24, and 26; (c) a nucleic acid molecule which hybridizes under stringent conditions to a polynucleotide consisting of a sequence selected from the group consisting of SEQ ID NO:1, 3, 5, 7, 9, 11, 13, 15, 17, 19, 21, 23, and 25 and which encodes a TrpB mutant polypeptide that as an independent subunit catalyze the production of NCAAs, UAAs from an indole or indole derivative and L-serine or L-threonine; or (d) a nucleic acid molecule which hybridizes under stringent conditions to a polynucleotide consisting of sequence selected from the group consisting of SEQ ID NO:1, 3, 5, 7, 9, 11, 13, 15, 17, 19, 21, 23, and 25 and which encodes a polypeptide that comprises the amino acid sequence selected from the group consisting of SEQ ID NO: 10, 12, 14, 16, 18, 20, 22, 24, and 26.

In one embodiment, an isolated nucleic acid molecule that includes a nucleic acid molecule of the disclosure and a nucleotide sequence encoding a heterologous polypeptide or peptide is provided. For example, a coding sequence for a tag (e.g., a polyHis Tag) can be linked to a polynucleotide of the disclosure.

In general, the disclosure includes any TrpB mutant polypeptide encoded by a modified TrpB polynucleotide derived by mutation, recursive sequence recombination, and/or diversification of the polynucleotide sequences described herein, wherein the polypeptide has novel substrate specificity, can catalyze a reaction independent of the TrpA subunit and can produce NCAAs, UAAs and/or other novel/desired chemical entities including intermediates for further metabolic and/or chemical modifications.

A nucleic acid molecule of the disclosure, e.g., a nucleic acid molecule that encodes a polypeptide set forth in any of SEQ NOs:2, 4, 6, 8, 10, 12, 14, 16, 18, 20, 22, 24, or 26, or having the nucleotide sequence of set forth in any of SEQ ID NOs:1, 3, 5, 7, 9, 11, 13, 15, 17, 19, 21, 23, or 25, or a portion thereof, can be isolated using standard molecular biology techniques and the sequence information provided herein.

A nucleic acid of the disclosure can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer. In some embodiments, an isolated nucleic acid molecule of the disclosure comprises a nucleic acid molecule which is a complement of a nucleotide sequence encoding a polypeptide having a sequence selected from the group consisting of SEQ NOs: 10, 12, 14, 16, 18, 20, 22, 24, and 26. In still another embodiment, an isolated nucleic acid molecule of the disclosure comprises a nucleotide sequence which is at least about 50%, 54%, 55%, 60%, 62%, 65%, 70%, 75%, 78%, 80%, 85%, 86%, 90%, 95%, 97%, 98% or more identical to the nucleotide sequence encoding a polypeptide selected from the group consisting of SEQ NOs: 2, 4, 6, 8, 10, 12, 14, 16, 18, 20, 22, 24, and 26, and having mTrpB activity or having the nucleotide sequence selected from the group consisting of SEQ ID NOs: 9, 11, 13, 15, 17, 19, 21, 23, and 25.

Nucleic acid molecules are "hybridizable" to each other when at least one strand of one polynucleotide can anneal to another polynucleotide under defined stringency conditions. Stringency of hybridization is determined, e.g., by (a) the temperature at which hybridization and/or washing is performed, and (b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.) require correspondingly less overall complementarity between the hybridizing sequences (1×SSC is 0.15 M NaCl, 0.015 M Na citrate). Nucleic acid molecules that hybridize include those which anneal under suitable stringency conditions and which encode polypeptides or enzymes having the same function, such as the ability to catalyze the conversion of an indole or indole derivative and L-serine or L-threonine to a NCAA or UAA. Further, the term "hybridizes under stringent conditions" is intended to describe conditions for hybridization and washing under which nucleotide sequences at least 60% or greater in homology to each other typically remain hybridized to each other. Preferably, the conditions are such that sequences at least about 70%, more preferably at least about 80%, even more preferably at least about 85% or 90% homologous to each other typically remain hybridized to each other.

The skilled artisan will appreciate that changes can be introduced by mutation into the nucleotide sequences of any nucleic acid sequence provided herein or any nucleic acid encoding a polypeptide of the disclosure.

Also contemplated are those situations where it is desirable to alter the activity of a parent polypeptide such that the polypeptide has new or increased activity on a particular substrate. It is understood that these amino acid substitutions will generally not constitute "conservative" substitutions. Instead, these substitutions constitute non-conservative substitutions introduced into a sequence in order to obtain a new or improved activity. For example, a polypeptide set forth SEQ ID NOs: 10, 12, 14, 16, 18, 20, 22, 24, or 26 include specific amino acid substitutions that include one or more mutations at a position selected from the group consisting of 16, 17, 68, 95, 104, 139, 166, 183, 186, 212, 274, 292, 321, 384 compared to the wild-type sequence of SEQ ID NO:2 and which mutations contribute to the alteration of the activity of the polypeptide.

It is also understood that an isolated nucleic acid molecule encoding a polypeptide having identity to or homologous to a polypeptide of SEQ ID NO: 2, 4, 6, 8, 10, 12, 14, 16, 18, 20, 22, 24, or 26 can be created by introducing one or more nucleotide substitutions, additions, or deletions into the nucleotide sequence encoding the particular polypeptide, such that one or more amino acid substitutions, additions or deletions are introduced into the encoded protein. Mutations can be introduced into the nucleic acid sequence by standard techniques, such as site-directed mutagenesis and PCR-mediated mutagenesis. In contrast to those positions where it may be desirable to make a non-conservative amino acid substitutions (see above), in some positions it is preferable to make conservative amino acid substitutions.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100:468-500; and Zoller &

Smith (1987) "Oligonucleotide-directed mutagenesis: a simple method using two oligonucleotide primers and a single-stranded DNA template" Methods in Enzymol. 154: 329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787; Nakamaye & Eckstein (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999) (each of which is incorporated by reference).

Additional suitable methods include point mismatch repair (Kramer et al. (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh & Henikoff (1986) "Use of oligonucleotides to generate large deletions" Nucl. Acids Res. 14: 5115), restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the α-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shot-gun' gene synthesis" Nucl. Acids Res. 13: 3305-3316); double-strand break repair (Mandecki (1986); Arnold (1993) "Protein engineering for unusual environments" Current Opinion in Biotechnology 4:450-455; and "Oligonucleotide-directed double-strand break repair in plasmids of *Escherichia coli*: a method for site-specific mutagenesis" Proc. Natl. Acad. Sci. USA, 83:7177-7181) (each of which is incorporated by reference). Additional details on many of the above methods can be found in Methods in Enzymology Volume 154, which also describes useful controls for trouble-shooting problems with various mutagenesis methods.

Additional details regarding various diversity generating methods can be found in the following U.S. patents, PCT publications, and EPO publications: U.S. Pat. No. 5,605,793 to Stemmer (Feb. 25, 1997), "Methods for In vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/13487 by Stemmer et al., "Methods for Optimization of Gene Therapy by Recursive Sequence Shuffling and Selection;" WO 00/00632, "Methods for Generating Highly Diverse Libraries;" WO 00/09679, "Methods for Obtaining in vitro Recombined Polynucleotide Sequence Banks and Resulting Sequences;" WO 98/42832 by Arnold et al., "Recombination of Polynucleotide Sequences Using Random or Defined Primers;" WO 99/29902 by Arnold et al., "Method for Creating Polynucleotide and Polypeptide Sequences;" WO 98/41653 by Vind, "An in vitro Method for Construction of a DNA Library;" WO 98/41622 by Borchert et al., "Method for Constructing a Library Using DNA Shuffling;" WO 98/42727 by Pati and Zarling, "Sequence Alterations using Homologous Recombination;" WO 00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" WO 01/23401 by Welch et al., "Use of Codon-Varied Oligonucleotide Synthesis for Synthetic Shuffling;" and WO 01/64864 "Single-Stranded Nucleic Acid Template-Mediated Recombination and Nucleic Acid Fragment Isolation" by Affholter (each of which is incorporated by reference).

Also provided are recombinant constructs comprising one or more of the nucleic acid sequences as broadly described above. The constructs comprise a vector, such as, a plasmid, a cosmid, a phage, a virus, a bacterial artificial chromosome (BAC), a yeast artificial chromosome (YAC), or the like, into which a nucleic acid sequence of the disclosure has been inserted, in a forward or reverse orientation. In a preferred aspect of this embodiment, the construct further comprises regulatory sequences including, for example, a promoter operably linked to the sequence. Large numbers of suitable vectors and promoters are known to those of skill in the art, and are commercially available.

Accordingly, in other embodiments, vectors that include a nucleic acid molecule of the disclosure are provided. In other embodiments, host cells transfected with a nucleic acid molecule of the invention, or a vector that includes a nucleic acid molecule of the invention, are provided. Host cells include eucaryotic cells such as yeast cells, insect cells, or animal cells. Host cells also include prokaryotic cells such as bacterial cells.

The terms "vector", "vector construct" and "expression vector" mean the vehicle by which a DNA or RNA sequence (e.g. a foreign gene) can be introduced into a host cell, so as to transform the host and typically express (e.g. transcription and translation) the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can be readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

Polynucleotides provided herein can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses and many others. Any vector that transduces genetic material into a cell, and, if replication is desired, which is replicable and viable in the relevant host can be used.

Vectors can be employed to transform an appropriate host to permit the host to express a mutant TrpB polypeptide or protein. Examples of appropriate expression hosts include: bacterial cells, such as *E. coli, B. subtilis, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 br Bowes melanoma; or plant cells or explants, etc.

In bacterial systems, a number of expression vectors may be selected depending upon the use intended for the mutant TrpB polypeptide. For example, when large quantities of mutant TrpB polypeptide or fragments thereof are needed for commercial production or for induction of antibodies, vectors which direct high-level expression of fusion proteins that are readily purified can be desirable. Such vectors include, but are not limited to, multifunctional *E. coli* cloning and expression vectors such as BLUESCRIPT (Stratagene), in which the mutant TrpB polypeptide coding sequence may be ligated into the vector in-frame with sequences for the amino-terminal Met and the subsequent 7 residues of beta-galactosidase so that a hybrid protein is produced; pIN vectors (Van Heeke & Schuster (1989) J. Biol. Chem. 264: 5503-5509); pET vectors (Novagen, Madison Wis.); and the like.

Similarly, in the yeast *Saccharomyces cerevisiae* a number of vectors containing constitutive or inducible promoters such as alpha factor, alcohol oxidase and PGH may be used for production of the TrpB polypeptides of the invention. For reviews, see Ausubel (supra) and Grant et al. (1987) Methods in Enzymology 153:516-544 (incorporated herein by reference).

Also provided are engineered host cells that are transduced (transformed or transfected) with a vector provided herein (e.g., a cloning vector or an expression vector), as well as the production of polypeptides of the disclosure by recombinant techniques. The vector may be, for example, a plasmid, a viral particle, a phage, etc. The engineered host cells can be cultured in conventional nutrient media modified as appropriate for activating promoters, selecting transformants, etc. Culture conditions, such as temperature, pH and the like, are those previously used with the host cell selected for expression, and will be apparent to those skilled in the art and in the references cited herein, including, e.g., Sambrook, Ausubel and Berger, as well as e.g., Freshney (1994) Culture of Animal Cells: A Manual of Basic Technique, 3rd ed. (Wiley-Liss, New York) and the references cited therein.

In other embodiments, methods for producing a cell that converts an indole or indole derivative a substrate (e.g., L-serine or L-threonine) to a desired chemical entity, are provided. Such methods generally include transforming a cell with an isolated nucleic acid molecule (or vector containing the same) encoding a mutant TrpB polypeptide of the disclosure.

In other embodiments, methods for producing NCAAs, UAAs and desired chemical entities are provided. The methods include: (a) providing a cell containing a nucleic acid construct comprising a nucleotide sequence that encodes a mutant TrpB, (b) culturing the cell in the presence of a suitable indole or indole derivative and L-serine or L-threonine and under conditions where the mutant TrpB is expressed at an effective level; and (c) producing an NCAA, UAA or chemical entity. In another embodiments, the methods include: (a) providing a cell containing a nucleic acid construct comprising a nucleotide sequence that encodes a mutant TrpB, (b) culturing the cells under conditions to express the mTrpB; (c) isolating the mTrpB to obtain a substantially purified mTrpB preparation or preparing a disrupted or cell-free preparation of mTrpB; (d) contacting/Admixing the mTrpB with a suitable indole or indole derivative and L-serine; and (e) producing an NCAA, UAA or chemical entity.

In another embodiment, methods of producing di-substituted tryptophan analogs, 4-, 5-, 6- or 7-nitrotryptophan or tryptophan analogs thereof are provided. The method includes (a) providing L-serine, an indole or indole derivative or nitro-indole, and a mutant TrpB of the disclosure. Admixing the components for sufficient time and under suitable conditions to produce the di-substituted tryptophan analogs, 4-, 5-, 6- or 7-nitrotryptophan or tryptophan analogs.

TrpB from *P. furiosus* and *Thermotoga maritima* are optimal parents for directed evolution, due to their high thermostability. The wild-type proteins (PfTrpB and TmTrpB), as well as the already-generated stand-alone variants were tested for their ability to produce 4-nitroTrp. The wild-type enzymes exhibited only trace activity. In addition, many of the variants formed a significant amount of the isotryptophan (1, FIG. 4) as a side product. One variant, Pf2B9 (SEQ ID NO:10), provided 18% conversion of 4-nitroindole to 4-nitroTrp. Notably, this variant, which has eight mutations from wild-type PfTrpB, was initially evolved for activity with indole and threonine (Thr). Thus, the fortuitous improvement for 4-nitroindole and Ser lent support to the hypothesis that optimizing a catalyst for production of 4-nitroTrp would provide simultaneous gains for other substrates.

The TrpB catalytic mechanism was analyzed in order to identify what might be limiting conversion of 4-nitroindole. TrpB uses the cofactor pyridoxal phosphate (PLP), which is covalently bound to a lysine residue in the active site (FIG. 4A, intermediate I). The lysine is displaced by Ser (intermediate II), which then undergoes α-deprotonation (intermediate III) and β-elimination to generate the active electrophile, amino-acrylate IV. Ideally, this would be attacked by the nucleophilic substrate, such as 4-nitroindole, to form the Trp product.

Figures 6A, 6B:
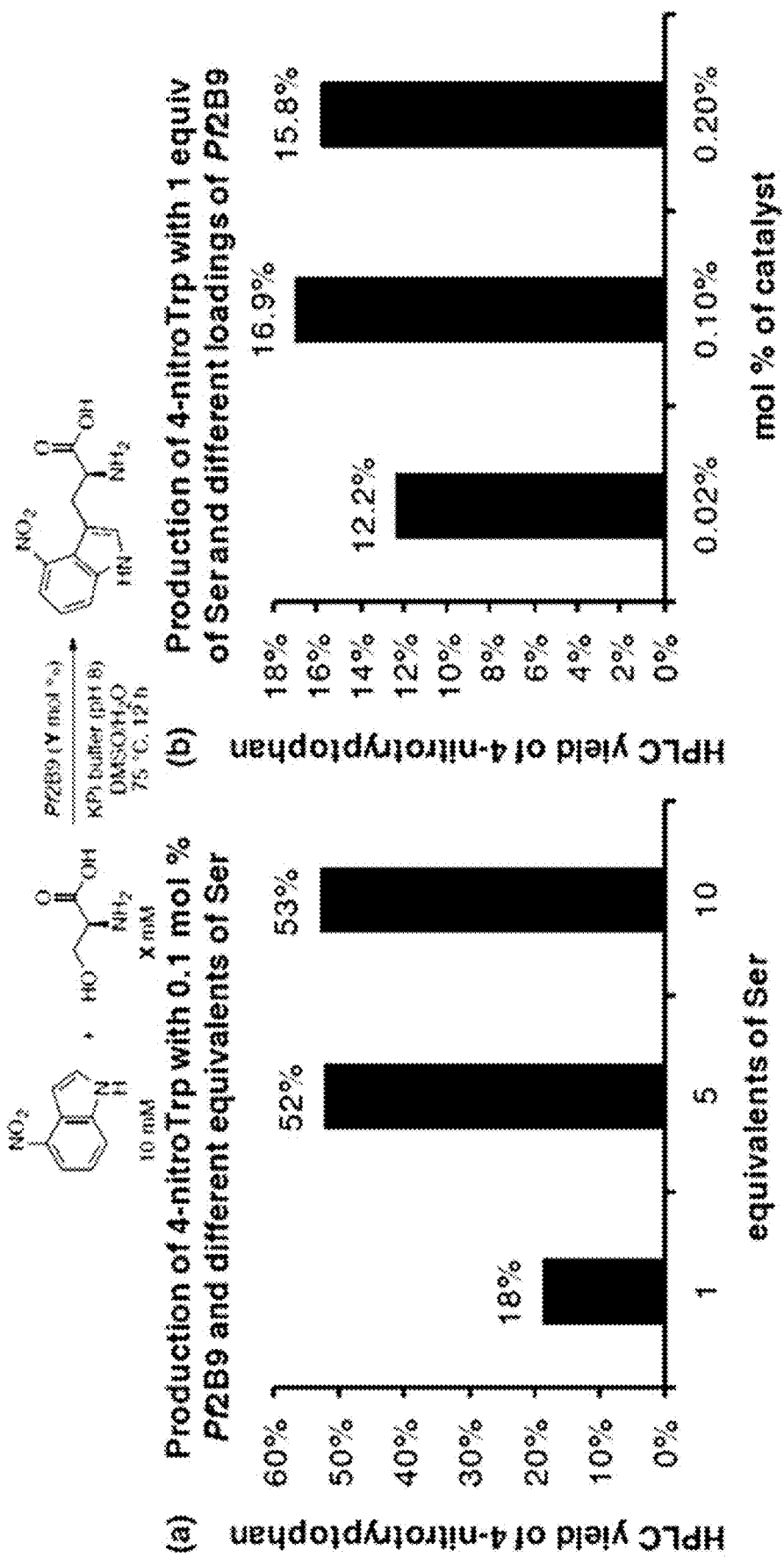
FIG. 6A-B shows production of 4-nitrotryptophan under different conditions. (A) HPLC yield with 0.02, 0.05, 0.1, and 0.2 mol % of Pf2B9 (1 equiv of Ser). (B) HPLC yield with 1, 5, and 10 equivalents of Ser (0.1 mol % of Pf2B9).

Increasing the catalyst loading had a negligible effect on production of 4-nitroTrp (FIG. 6A), but the Ser was completely consumed at the end of the reaction period. By contrast, production of 4-nitroTrp was improved by addition of excess Ser (FIG. 6B). These observations are consistent with the known side reaction in which the amino-acrylate is ejected from the PLP cofactor and undergoes hydrolytic decomposition to pyruvate (FIG. 4B). In addition, and especially at early reaction times, formation of isotryptophan 1 was observed (FIG. 4C), in which 4-nitroindole atom (N1) rather than the desired carbon atom (C3). While this reaction appears to be reversible, it undoubtedly slows the desired reaction. The goal was to engineer a TrpB that would rapidly and quantitatively convert equimolar amounts of 4-nitroindole and Ser into 4-nitroTrp with perfect regio- and enantioselectivity.

Figure 5A:
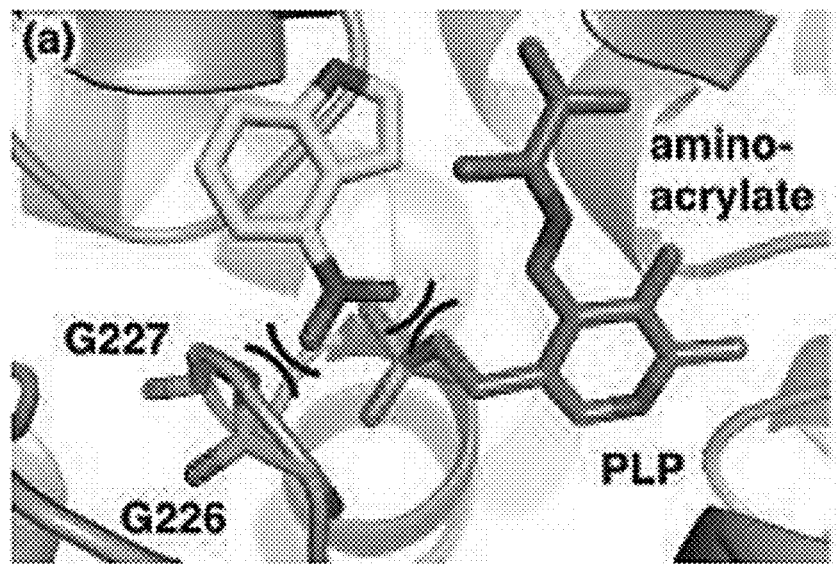
FIG. 5A-B shows a model of 4-nitroindole in the active site of Pf2B9 (PDB ID: 5VM5). (A) Nitro group clashes with the protein backbone and the PLP cofactor. (B) Alternative view showing side-chains extending in to the active site and hydrogen bond with E104.
Figure 5B:
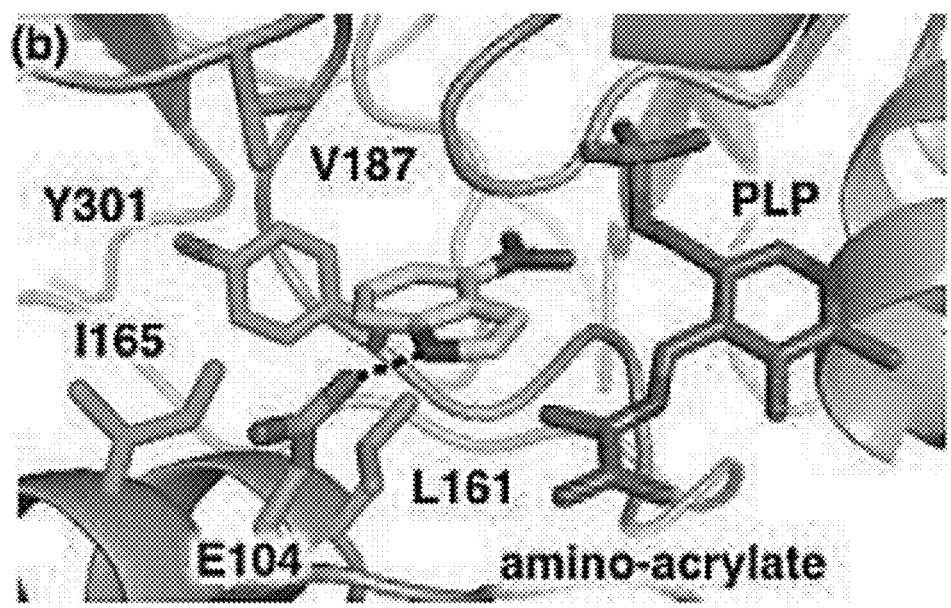

Small site-saturation mutagenesis libraries were developed that could be screened by high-performance liquid chromatography (HPLC). 4-nitroindole was modeled into the binding pose necessary to achieve C—C bond formation, in the hope of identifying steric clashes that could be alleviated by mutations. The model suggested that the nitro group was clashing with the protein main chain as well as with the PLP cofactor (FIG. 5A). Nonetheless, four residues were identified whose side chains extended into the indole-binding pocket: L161, I165, V187, and Y301 (FIG. 5B). The sidechain of E104 also occupies the active site, but this residue is thought to bind indole through the NH moiety, thereby promoting attack from C3. Since this residue is universally conserved in TrpB homologs, and 4-nitroindole already suffers from poor regioselectivity, mutagenesis at this position was avoided. It was hypothesized that mutation at the other four positions could create space for 4-nitroindole to bind in an alternative pose that relieved the steric clashes but still allowed for attack of the amino-acrylate.

Figure 7:
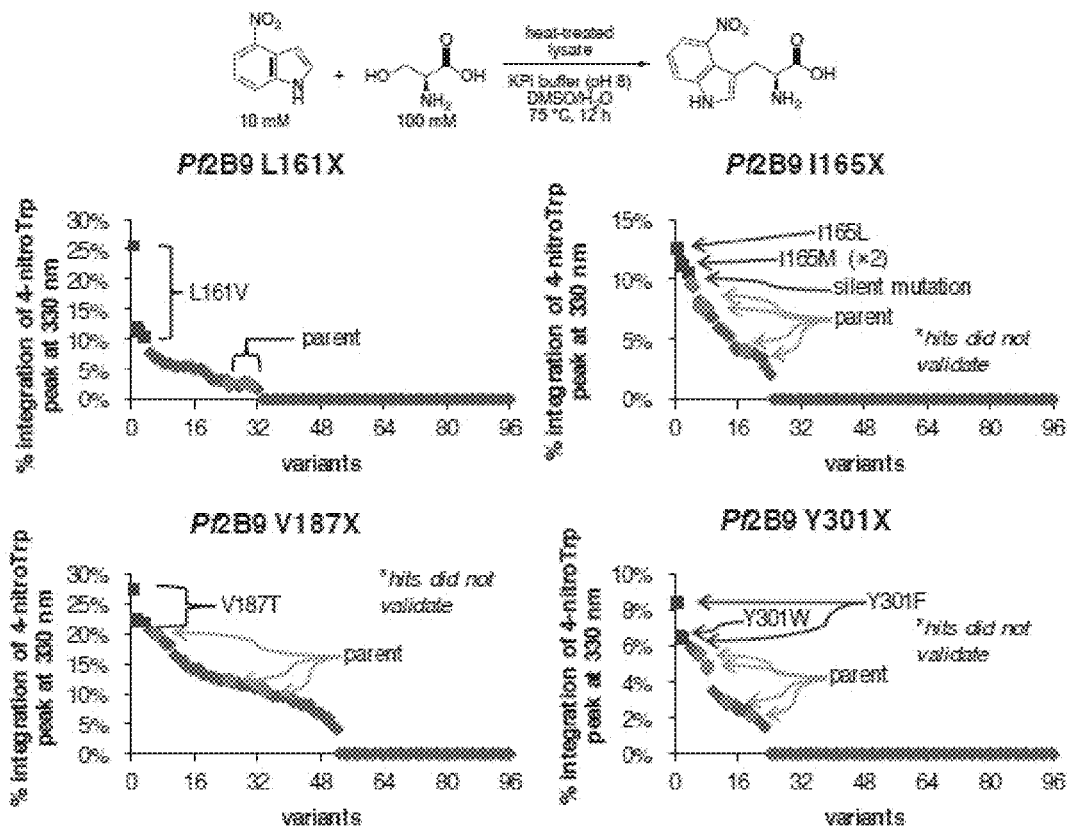
FIG. 7 shows site-saturation of Pf2B9 at L161, I165, V187, and Y301 for production of 4-nitrotryptophan. Product formation was measured by HPLC.

Surprisingly, mutations at the targeted residues were almost uniformly deleterious (FIG. 7), with the exception of L161V, which boosted the yield of 4-nitroTrp to 25%. While this improvement is modest, the mutation also suppressed the formation of isotryptophan 1. It is worth noting that although the side-chain of valine is indeed smaller than that of leucine, mutation of this position to alanine is deleterious.

Figure 8:
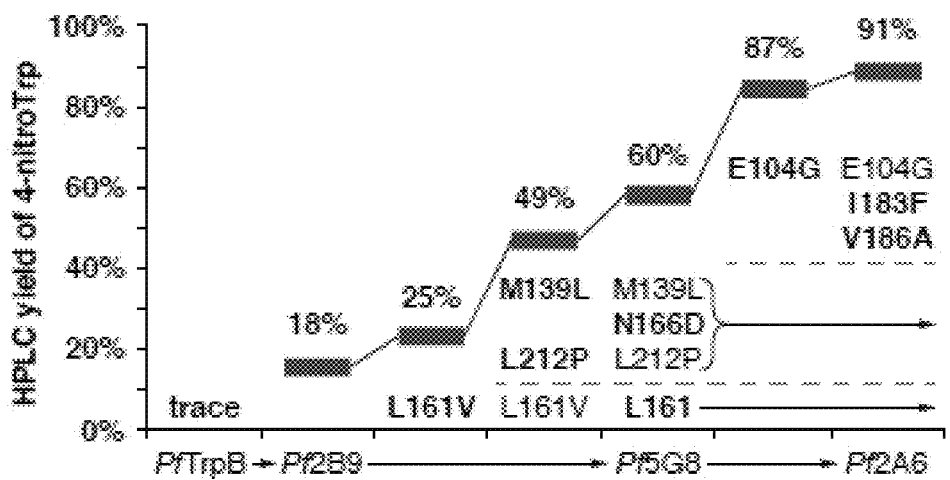
FIG. 8 shows evolutionary progression in production of 4-nitroTrp. Mutations in bold were added in the corresponding round of mutagenesis and screening. Dashed lines denote a new round of random mutagenesis. The horizontal axis indicates catalyst designations.

A random mutagenesis library, generated by error-prone polymerase chain reaction, was used and identified a variant, with mutations M139L and L212P, that almost doubled the HPLC yield of 4-nitroTrp to 49% (FIG. 8). A library which randomly recombined those two mutations and N166D, a beneficial mutation, was tested. The active-site L161V mutation was randomly varied, since its effect had been comparatively minor. Indeed, in the best variant from this library (Pf5G8; SEQ ID NO:14), the active-site mutation had reverted back to leucine and the other three mutations were retained. This variant formed 4-nitroTrp in 60% HPLC yield from equimolar amounts of 4-nitroindole and Ser.

Figure 9:
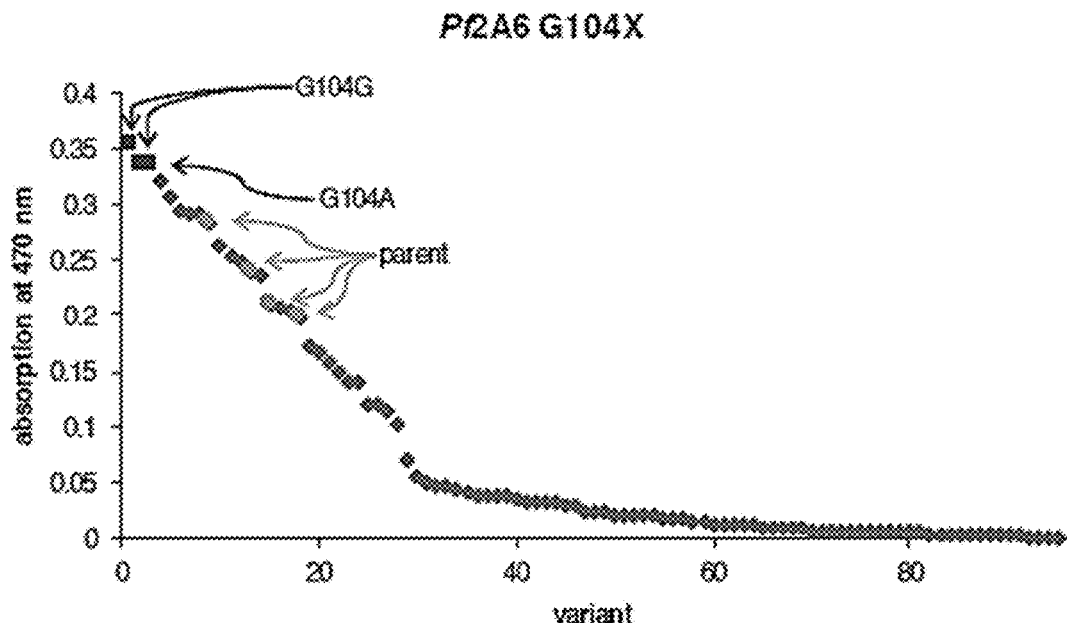
FIG. 9 shows site-saturation of Pf2A6 at position G104 for production of 4-nitrotryptophan. Production was measured on a UV-vis plate reader.

Another random mutagenesis library was generated with Pf5G8 as the parent protein. From this library, two mutations (I183F and V186A) that increased HPLC yield slightly, to ~70%. A further improvement, however, came from a variant bearing the mutation E104G (SEQ ID NO:16), which increased HPLC yield to ~87% and eviscerated the earlier supposition that an H-bonding interaction with 4-nitroindole and the side-chain of E104 would promote the reaction. A recombination library was then screened and it was found that the E104G mutation recombined with I183F and V186A to produce 4-nitroTrp in 91% HPLC yield. A site-saturation library was screened at position 104 and it was determined that glycine at this position was optimal, with Ala yielding similar, but slightly inferior results (FIG. 9).

The identified enzymes Pf5G8 (SEQ ID NO:14) and Pf2A6 (SEQ ID NO:18) were also tested against other nitroindole derivatives (Table B). Pf5G8 showed improvement for all substrates compared to Pf2B9 (SEQ ID NO:10), forming all isomeric nitrotryptophans in about 60% HPLC yield (Table 1, entries 1 and 2). Enzyme Pf2A6, on the other hand, showed almost quantitative conversion of 7-nitroindole to the corresponding nitroTrp, but had lower activity with 5- and 6-nitroindole (Table 1, entry 3). Because catalysts were identified that exhibited moderate activity with these substrates, experiments were further performed to detemring if a subset of the mutations from Pf2A6 would further activate them for 5- and 6-nitroindole.

TABLE B

Nitro substitution positions:

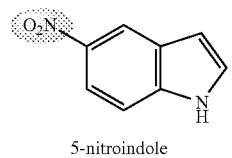

5-nitroindole

TABLE B-continued

Nitro substitution positions:

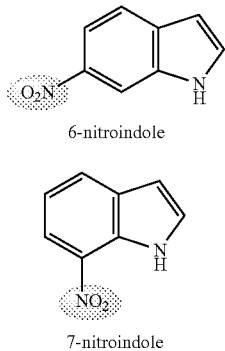

6-nitroindole 7-nitroindole

TABLE 1

Catalyst activity to other nitroindole isomers:

| Entry | Catalyst | HPLC yield of nitroTrp (%)[a] | | | |
|---|---|---|---|---|---|
| | | 4-nitro | 5-nitro | 6-nitro | 7-nitro |
| 1 | Pf2B9 | 18 | 7.5 | 17 | 33 |
| 2 | Pf5G8 | 60 | 69 | 66 | 60 |
| 3 | Pf2A6 | 91 | 3.5 | 22 | >99 |
| 4 | Tm2F3[b] | | 76 | | |
| 5 | Tm2F3 I184F | | 86 | | |
| 6 | Pf2B9 I165F Y301H | | | 66 | |
| 7 | Pf0A9[c] | | | 86 | |
| 8 | Pf0A9 E104G | | | 91 | |

[a]Reactions used equimolar amounts of nitroindole and Ser. [b]TmTrpB plus mutations P19G, I68V, K96L, P140L, N167D, L213P, T292S. [c]Pf2B9 plus mutations M139L, I165F, N166D, and Y301H.

Engineered variants of TmTrpB had higher activity with 5-substituted indoles than their PfTrpB homologs. In addition, when certain beneficial mutations in PfTrpB variants were transferred to the corresponding positions in TmTrpB, then the activating effects were also transferred. Thus, a library in which the mutations of Pf2A6 were randomly recombined at the corresponding positions in TmTrpB were made (see, alignment in FIG. 2). When this library was tested for activity with 5-nitroindole, two variants were identified that outperformed all previous catalysts in the production of 5-nitrotryptophan. The first variant, Tm2F3, contained five mutations that were originally found in Pf2B9 plus all three mutations from Pf5G8; this variant formed 5-nitrotryptophan in 76% HPLC yield (Table 1, entry 4). The second variant was identical, but also contained one of the mutations found in Pf2A6 (I184F, according to numbering in T. maritima). This variant gave a further boost in yield to 86% (Table 1, entry 5).

Figure 10:
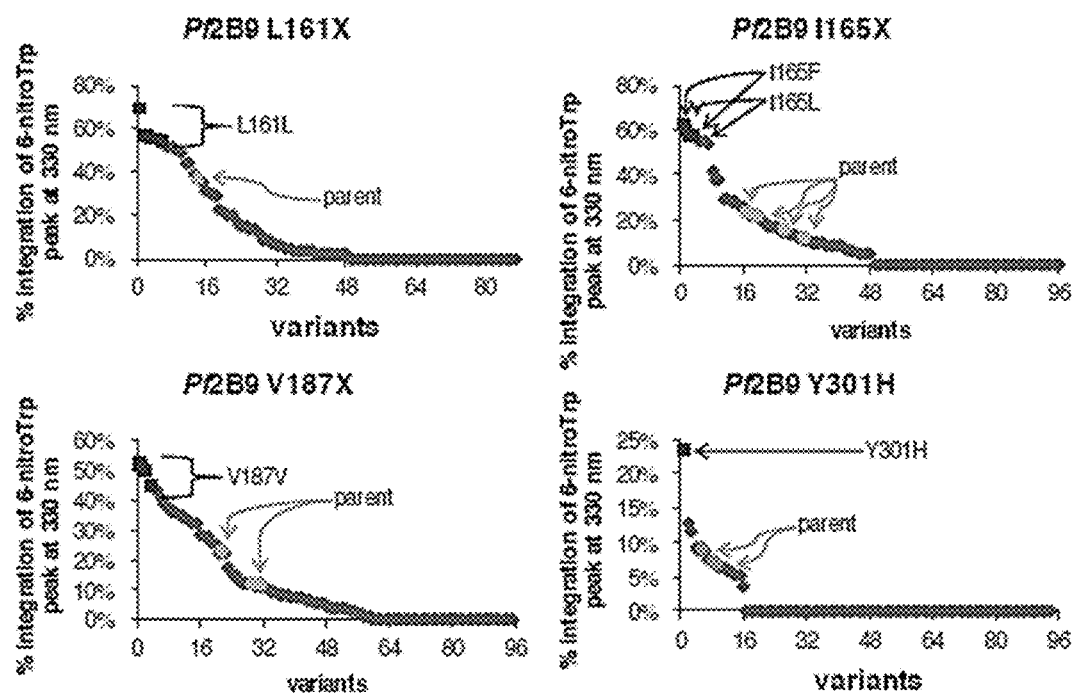
FIG. 10 shows site-saturation of Pf2B9 at L161, I165, V187, and Y301 for production of 6-nitrotryptophan. Product formation was measured by HPLC.

To improve activity with 6-nitroindole, mutation I165F and Y301H in SEQ ID NO:10 were both beneficial (FIG. 10). Ultimately, the best variant contained both of these mutations and formed 6-nitroTrp in 66% HPLC yield (Table 1, entry 6). Thus, the disclosure also provides a mutant TrpB comprising SEQ ID NO:10 with mutations at I165 and Y301 that (or sequences that are 85%, 90%, 95%, 98%, 99% identical to SEQ ID NO:10 and having mutations at I165 and Y301 wherein the polypeptide produces 6-nitroTrp from serine and 6-nitroindole).

A further random recombination library of the mutations from Pf2A6, from which a new variant, Pf0A9, was identified bearing mutations M139L and N166D, which increased the yield to 86% (Table 1, entry 7). Surprisingly, the mutation E104G also enhanced activity, albeit modestly, to 91% yield (Table 1, entry 8).

When the catalysts (mTrpBs of the disclosure) were applied to various indole analog substrates, the catalysts accepted essentially every indole analog tested, often forming the corresponding tryptophan product in excellent yield. For preparative reactions, however, halogenated and electron-deficient indoles were used, since historically these have been the most challenging.

With 4-nitroindole, Pf2A6 can achieve ~5000 turnovers, but the reaction seems to slow. As a result, a higher catalyst loading is used to achieve the high conversion observed in the catalyst evolution (Table 2, entry 1). Fortunately, the catalysts are expressed at high levels (>200 mg/L of E. coli culture) and can be used as heat-treated lysate, without additional protein purification. As a result, over a gram of 4-nitrotryptophan was obtained using the protein from a 1-L bacterial culture (Scheme 2). 4-fluorotryptophan was also obtained in excellent yield (Table 2, entry 2), as well as 4-bromo- and 4-cyanotryptophan (Table 2, entries 2 and 3, respectively).

Scheme 2

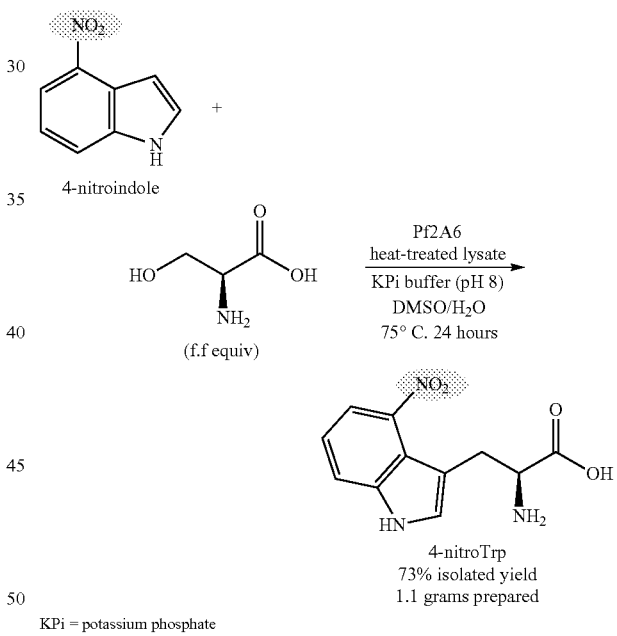

KPi = potassium phosphate

As with 4-nitroindole, the reaction with 5-nitroindole slowed toward the end. Nonetheless, 5-nitrotryptophan could be obtained in 88% yield with a higher catalyst loading (Table 2, entry 5). Good results were also obtained with other electron-withdrawing substituents, such as nitrile, carboxamide, and boronate (Table 2, entries 6-8). Notably, promising activity with 5-iodo- and 5-trifluoromethylindole (Table 2, entries 9 and 10) was observed.

The 6-substituted indoles proved to be the best behaved and most predictable series of substrates. At this position, high yields were obtained with the nitro substituent (Table 2, entry 11), as well as halo substituents (Table 2, entries 12 and 13) and other electron-withdrawing substituents like nitrile (Table 2, entry 14) and boronate (Table 2, entry 15).

Activity was also observed with 7-substituted indoles. While 7-nitroindole and 7-cyanoindole favored Pf2A6 (Table 2, entries 16 and 17), Pf0A9 gave optimal activity for 7-chloro- and 7-iodoindole (Table 2, entries 18 and 19). 7-bromotryptophan could be formed in modest yield with catalyst Pf5G8 (Table 2, entry 20).

The production of tryptophan analogs with multiple substituents was also examined (Table C). This capability is important both because poly-substituted Trp derivatives are precursors to many natural products and because polyhalogenated arenes are prevalent in bioactive compounds in general. The mTrpB's of the disclosure were capable of producing 5,6-disubstituted Trp 2 and 5,7-disubstituted Trp 3 in good yields using Pf5G8 and Tm2F3 I184F, respectively. The bulkier 5,7-disubstituted product 4 was also accessible.

TABLE C

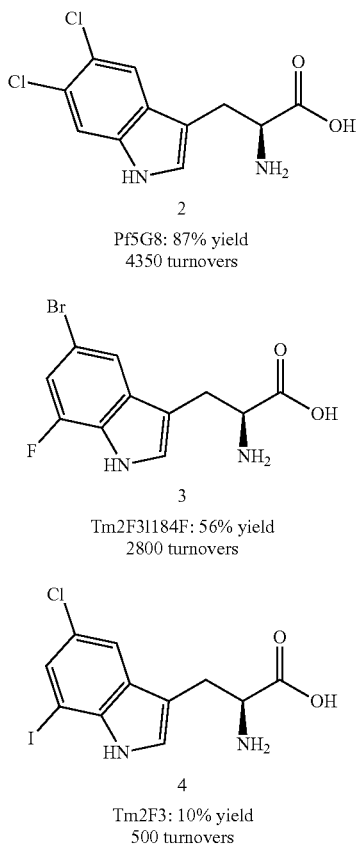

2
Pf5G8: 87% yield
4350 turnovers

3
Tm2F3I184F: 56% yield
2800 turnovers

4
Tm2F3: 10% yield
500 turnovers

While the poor solubility of 4-nitroindole affected the ability to measure Michaelis-Menten kinetics, the initial rate of 4-nitroTrp production was estimated under the reaction conditions by measuring conversion at short reaction times (Table 3). In addition, the rate of Ser deamination was measured by incubating the enzymes with Ser, in the absence of a nucleophilic substrate, and measuring the production of pyruvate. Compared to the initial variant, Pf2B9 (SEQ ID NO:10), variant Pf5G8 exhibits an increase in the rate of 4-nitroTrp production, but a six-fold decrease in the rate of Ser deamination (Table 3, entries 1 and 2). The mutation E104G improves both kinetic parameters in approximately equal measure (Table 3, entry 3). The addition of I183F and V186A actually increases the rate of Ser deamination, but increases the rate of the desired reaction even more (Table 3, entry 4).

TABLE 3

| | Kinetics | | |
|---|---|---|---|
| | | Initial turnover frequency (min$^{-1}$) | |
| Entry | Catalyst | to 4-nitroTrp | to pyruvate |
| 1 | Pf2B9 | 1.25 | 12 |
| 2 | Pf5G8 | 1.87 | 2.0 |
| 3 | Pf5G8 E104G | 3.33 | 0.87 |
| 4 | Pf2A6 | 6.82 | 1.4 |

Figure 11A:
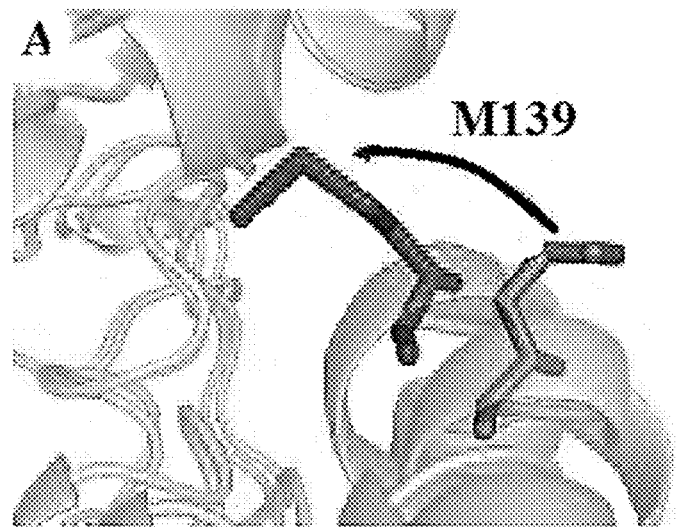
FIG. 11A-B shows overlaid crystal structures of PfTrpB (PDB ID: 5DVZ) in the open state and Pf2B9 (PDB ID: 5VM5) in the closed state showing the side-chain motion of (A) M139, (B) N166, and H275.
Figure 11B:
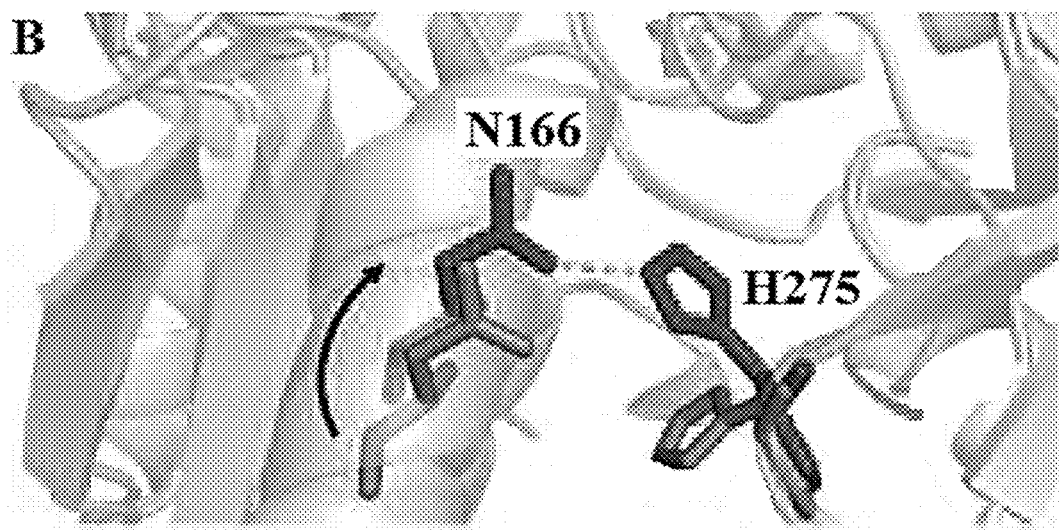

A comparison of the structures of wild-type PfTrpB in the open state, as well as Pf2B9 in the closed state revealed that the side-chain of M139, which is mutated to leucine in Pf5G8, undergoes a substantial movement when the protein transitions from open to closed (FIG. 11A). Thus, it is unsurprising that mutation at this position would influence the transition from open to closed. Residue N166, which is mutated to aspartate in Pf5G8, exhibits only a minor conformational change between open and closed, but its side-chain forms a hydrogen bond in the closed state with the side-chain of H275, which undergoes a rotameric switch that closes the active site (FIG. 11B). It is therefore plausible that strengthening of this interaction with the more basic aspartate would stabilize the closed state of the enzyme.

The mutations E104G, I183F, and V186A occur at positions in the enzyme active site. In the case of I183 and V186, the side chains do not interact directly with the substrates, nor do they undergo significant movement during the transition from the open to closed state. The beneficial effects of the mutations are likely due to subtle reshaping of the active site to accommodate the added bulk of 4-nitroindole and bind the substrate in a more reactive conformation. This is consistent with the observation that addition of these two mutations greatly increases the rate of 4-nitroTrp production while exerting little effect on the rate of Ser deamination (Table 3, entries 2 and 3).

Various roles have been assigned to the side-chain of E104, including activation of the Ser β-hydroxyl group as a leaving group, as well as binding and activation of the indole nucleophile (see FIG. 4, intermediates II and III). Indeed, studies of TrpS from *S. typhimurium* (StTrpS) showed that mutation of the corresponding residue to alanine eliminated activity with indole and Ser. However, this activity was rescued by the introduction of certain monovalent cations, such as Cs$^+$, indicating that neither of the aforementioned roles of E104 are essential. It therefore seems that its most significant role is in modulating the transition of the enzyme to the closed state. This was supported by the observation that increasing concentrations of CsCl shifted the catalytic steady state of the variant away from the external aldimine (FIG. 4, intermediate II) toward the amino-acrylate as the major species, a trend that is a hallmark of closed-state stabilization. By contrast, the amino-acrylate predominates in the steady state of both Pf5G8 and the E104G variant. In fact, the E104G mutation appears to stabilize the closed state, as inferred from the twofold decrease in deamination rate (Table 3, entries 1 and 2). Thus, it may be that the other mutations in Pf5G8 have changed the function of E104.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel") (each of which is incorporated by reference). Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the invention are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13: 563-564 (each of which is incorporated by reference). Improved methods for cloning in vitro amplified nucleic acids are described in Wallace et al., U.S. Pat. No. 5,426,039. Improved methods for amplifying large nucleic acids by PCR are summarized in Cheng et al. (1994) Nature 369: 684-685 and the references cited therein (incorporated by reference herein), in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The invention is illustrated in the following examples, which are provided by way of illustration and are not intended to be limiting.

EXAMPLES

Cloning, expression, and purification of TrpB variants. The genes encoding Pf2B9 and TmTrpB (UNIPROT ID P50909) were cloned into pET22(b)+ with a C-terminal His-tag. Protein expression of the variants was carried out in *Escherichia coli* BL21 E. cloni Express cells (Lucigen) by inoculating 5 mL of Lysogeny Broth containing 100 μg/mL ampicillin (LBamp) with a single colony and incubating this pre-culture overnight at 37° C. and 230 rpm. The overnight cultures were used to inoculate 500 mL of Terrific Broth containing 100 μg/mL ampicillin (TBamp). The expression cultures were shaken at 37° C. and 230 rpm for ~3 h, at which point the OD600 was 0.6-0.8. The cultures were then chilled on ice for >30 min and then induced with by the addition of 1 M aq. isopropyl β-D-thiogalactopyranoside (IPTG, 500 μL, final concentration of 1 mM). Expression of the homologs took place at 230 rpm and 20° C. for another 20 h. The cultures were subjected to centrifugation at 5,000×g and 4° C. for 5 minutes. The cell pellets were decanted, then frozen and stored at −30° C. until further use.

For protein purification, cells were thawed, then resuspended in potassium phosphate buffer (25 mM, pH 8) that contained 20 mM imidazole, 100 mM NaCl, 200 μM PLP, 1 mg/mL of hen egg white lysozyme (HEWL, Sigma Aldrich), and 0.1 mg/mL of bovine pancreas DNase I. BugBuster (Novagen) was added, then the mixture was vortexed to suspend the pellet. The suspension was shaken at 37° C. and 230 rpm for 15 min, then subjected to centrifugation at 5000×g and 4° C. for 10 minutes. Without decanting, the cell lysate was immersed in a water bath at 75° C. After 30 minutes, the suspension was subjected to another centrifugation step (15,000×g and 4° C. for 15 minutes). The supernatant was purified using a 1-mL histrap HP column with an AKTA purifier FPLC system (GE Healthcare) and a linear gradient from buffer A (25 mM potassium phosphate, 20 mM imidazole, 100 mM NaCl, pH 8) to buffer B (25 mM potassium phosphate, 500 mM imidazole, 100 mM NaCl, pH 8) over 10 volumes. Proteins eluted at approximately 140 mM imidazole. Purified proteins were dialyzed into potassium phosphate buffer (50 mM, pH 8), then flash-frozen in liquid N2 and stored at −80° C. until further use. Protein concentrations were determined via the Bradford assay (Bio-Rad).

Construction of site-saturation mutagenesis libraries. PCR was conducted using Phusion polymerase (New England Biolabs) according to the standard protocol. For the given site of mutagenesis, three primers were designed containing codons NDT (encoding for Ile, Asn, Ser, Gly, Asp, Val, Arg, His, Leu, Phe, Tyr, and Cys), VHG (encoding for Met, Thr, Lys, Glu, Ala, Val, Gln, Pro, and Leu), and TGG (Trp), respectively, thereby including all 20 natural amino acids. These three primers were mixed in a ratio 12:9:1. Then, the plasmid was constructed by site-directed mutagenesis by overlap extension (SOE) PCR using a plasmid that contained the parent gene in the pET22(b)+ vector as template. The linear plasmid was digested with DpnI, purified by preparative agarose gel, then cyclized via the Gibson method.

Construction of random recombination libraries. These libraries were constructed in an analogous manner to the site-saturation libraries, using primers that coded for both the native residue and the mutation. The mutant genes were first constructed as fragments, using flanking primers that corresponded to the NdeI and XhoI restriction sites on pET22(b)+. The fragments were purified by preparative agarose gel, then assembled into a contiguous gene using flanking primers that corresponded to the NdeI and XhoI sites of the pET22(b)+ vector. After a final purification by agarose gel, the assembled gene was cloned into an empty pET22(b)+ vector between restriction sites NdeI and XhoI using the Gibson method.

To improve production of 5-nitrotryptophan, recombination was performed in three stages. First, the mutations M18V, P19G, I69V, K96L, T292S, and H381A (relative to SEQ ID NO:6) were randomly recombined in the parent TmTrpB M145T N167D (relative to SEQ ID NO:6). The best variant from this library added the mutations P19G, I69V, K96L, and T292S (relative to SEQ ID NO:6). This served as the parent polypeptide for the second round, in which the mutations P140L, M145T, N167D, and L213P (relative to SEQ ID NO:6) were randomly recombined. The best variant from this library (Tm2F3; SEQ ID NO:24) added the mutations P140L and L213P, retained the mutation N167D, and reverted the mutation M145T to the native residue (M). This served as the parent for the third round, in which the mutations E105G, I185F, and V187A were randomly recombined. The best variant from this library added the mutation I184F (see, e.g., SEQ ID NO:26).

To improve production of 6-nitrotryptophan, recombination was performed in two stages. First, the mutations M139L, N166D, and L212P were randomly recombined in the parent Pf2B9 (SEQ ID NO:10) further including I165F and Y301H. The best variant from this library (Pf0A9; SEQ ID NO:20) added mutations M139L and N166D. This served as the parent polypeptide for the second round, in which the mutations E104G, I183F, and V186A were randomly recombined. The best variant from this library added the mutation E104G (SEQ ID NO:22).

Construction of random mutagenesis libraries. Random mutagenesis was achieved with error-prone PCR using Taq polymerase (New England Biolabs):

| Reagents mixed in a PCR tube | | Thermocycler program | | |
|---|---|---|---|---|
| Taq buffer (10×) | 10 µL | 95° C. | 40 s | |
| dNTP mix (200 µM) | 2 µL | 95° C. | 30 s | |
| forward primer[a] (100 µM) | 2 µL | 55° C. | 30 s | 30 cycles |
| reverse primer[b] (100 µM) | 2 µL | 68° C. | 80 s | |
| template DNA | 1 µL | 68° C. | 5 min | |
| MnCl$_2$ (1 mM) | 20/30/40 µL | 10° C. | ∞ | |
| Taq DNA Polymerase (added last) | 0.5 µL | | | |
| H$_2$O | Add to 100 µL total volume | | | |

[a]Forward Primer corresponded to the NdeI restriction site for the pET22 (b) + vector.
[b]Reverse primer corresponded to the XhoI restriction site of the pET22 (b) + vector.

The PCR product was purified by preparative agarose gel, then cloned into an empty pET22(b)+ vector between restriction sites of NdeI and XhoI using the Gibson method. 5 Libraries generated with 200, 300, and 400 µM MnCl2 were tested (one 96-well plate, each) to determine which library gave the optimal balance of high diversity and low rate of inactivation. The chosen library was then tested further.

Transformation of BL21 E. coli cells. In preparation, SOC medium, 50 µL aliquots of electrocompetent BL21 E. coli cells, and electroporation cuvettes were chilled in ice. The plasmid (1 µL) was added to the cells, which were then transferred to a sterile electroporation cuvette. An electric potential was applied with a Gene Pulser Xcell (2.5 kV, 25 pF, 200Ω). Then, SOC medium (750 µL) was immediately added and the cuvette was shaken at 37° C. and 230 rpm. After 45 min, aliquots of cell suspension were plated onto LBamp agar plates. The plates were incubated overnight at 37° C., then stored at 4° C. until further use.

Library expression and screening. BL21 E. cloni Express cells carrying parent and variant plasmids were grown in 96-well deep-well plates (300 µL/well TBamp) at 37° C. and 80% humidity. After shaking at 250 rpm overnight, 20 µL of the overnight cultures were transferred to new deep-well plates containing 630 µL/well TBamp, which were allowed to grow at 37° C. and 80% humidity. After shaking at 250 rpm for 3 h, the plates were chilled on ice for 30 min, then induced by the addition of IPTG in TBamp (1 mM final concentration). The cultures were shaken at 250 rpm and 20° C. After 20 hours, the cultures were subjected to centrifugation at 4,000×g for 10 min. The cell pellets were frozen at −30° C. for a minimum of 2 hours. For screening, cells were thawed at room temperature and then subjected to lysis by the addition of 400 µL/well of potassium phosphate buffer (50 mM, pH 8.0), with 1 mg/mL HEWL, 0.1 mg/mL DNase I, 40 µM PLP, and 2 mM MgCl$_2$. The plates were incubated for 1 h at 37° C., then transferred to a water bath equilibrated to 75° C. After 30 min, the plates were chilled in ice, then subjected to centrifugation at 5,000×g and 4° C. for 20 min.

The reactions were performed in 96-well deep-well plates. In general, each well was charged with the nitroindole substrate as a solution in DMSO (10 µL/well). Then, a solution of Ser in potassium phosphate buffer (200 mM, pH 8.0) was added. Finally, the enzymes were added as heat-treated lysate, such that the total volume in the wells was 200 µL. All libraries were screened with 2 µmol of nitroindole and 2 µmol of Ser, except for the first rand ommutagenesis library, which used 0.2 µmol 4-nitroindole and 2 µmol of Ser. The volume of heat-treated lysate was decreased in each successive round of evolution (80 µL to 20 µL), in order to apply greater selective pressure.

The plates were sealed with Teflon sealing mats, then immersed in a water bath equilibrated to 75° C. After ~12 hours, the plates were chilled in ice and subjected to brief centrifugation (5,000×g, 2 min) to settle the reaction contents to the bottom of the wells. Each well was charged with 700 µL of ethyl acetate and 500 µL of aq. 1 M HCl. The plates were again sealed with Teflon sealing mats, then shaken vigorously to dissolve all precipitates and partition the product and substrate between the aqueous and organic phases, respectively. The plates were again subjected to centrifugation (5,000×g, 2 min), then 200 µL of the aqueous phase were transferred to 96-well UV-vis assay plates. The activity of each well was determined by measuring the absorption at a given wavelength; the wavelength was determined by scanning one of the parent controls from 390 to 500 nm and choosing the wavelength at which the absorption was ~0.5.

For smaller libraries, such as for site-saturation mutagenesis, the reactions could also be analyzed by HPLC. In this case, the reactions were diluted with 300 µL of 83% cetonitrile/water (for 4-nitroindole reactions, 1 M aq. HCl was used in place of water). The plates were subjected to centrifugation at 5,000×g and 4° C. for 10 minutes, then the supernatants were transferred to a fresh assay plate. Each well was analyzed with a C-18 silica column (4.6×50 mm) using acetonitrile/water (0.1% acetic acid by volume): 5% to 95% acetonitrile over 2 minutes, 95% for 1 min; 1 mL/min. The yield was approximated by comparing the integrations of the nitrotryptophan signal to the nitroindole signal at 330 nm (no reference wavelength).

Small-scale reactions with heat-treated lysate. The enzyme was expressed as a 5-mL culture in TBamp according to the procedure in Section 5.1. The cell pellet was suspended in 400 µL potassium phosphate buffer (50 mM, pH 8) that contained 1 mg/mL HEWL, 0.1 mg/mL DNase I, and 200 µM PLP. BugBuster was added, then the suspension was shaken at 37° C. and 230 rpm. After 15 minutes, the suspension was chilled in ice, then subjected to centrifugation at 5,000×g and 4° C. (10 minutes). The supernatant was transferred to a 1.5-mL Eppendorf tube, then heated to 75° C. After 30 minutes, the suspensions were chilled in ice, then subjected to centrifugation at 20,000×g and 4° C. (10 minutes). The heat-treated lysate was used directly in the biocatalytic reactions.

A 2-mL HPLC vial was charged with nitroindole as a 200-mM solution in DMSO (10 μL, 2 μmol nitroindole). Next, Ser (2 μmol) was added as a solution in 180 μL of potassium phosphate buffer (200 mM, pH 8). Finally, 10 μL of heat-treated lysate was added, then the reaction was heated to 75° C. After 12 hours, the reaction was chilled in ice, then diluted with 800 μL of 1:1 CH$_3$CN/1 M aq. HCl. The reaction mixture was subjected to centrifugation at 20,000×g and 4° C. (10 minutes), then the supernatant was analyzed by HPLC with a C-18 silica column (1.8 μm, 2.1×50 mm) using acetonitrile/water (0.1% acetic acid by volume): 5% to 95% acetonitrile over 4 min; 1 mL/min. For 4-nitrotryptophan, the HPLC yield was determined using the method described in Section 5.9. For the other nitrotryptophans, the HPLC yield was estimated by comparing the integrations of the product and substrate peaks at 330 nm (no reference wavelength).

Small-scale reactions with purified protein. A 2-mL HPLC vial was charged with nitroindole as a 200-mM solution in DMSO (10 μL, 2 μmol nitroindole). Next, Ser (2 μmol) and PLP (5 equiv relative to enzyme) was added as a solution in 182 μL of potassium phosphate buffer (200 mM, pH 8). Finally, 8 μL of purified protein solution was added (concentration was adjusted depending on the desired catalyst loading).

Calibration for measuring HPLC yield of 4-nitrotryptophan. Using an authentic standard of 4-nitrotryptophan, mixtures were prepared that contained 4-nitroindole and 4-nitrotryptophan in different ratios (9:1, 3:1, 1:1, 1:3, and 1:9). Each mixture was prepared in duplicate, then all were analyzed by HPLC. The ratios of the product and substrate peaks at 254 nm (reference 360 nm, bandwidth 100 nm) and 330 nm (no reference wavelength) were correlated to the actual ratios by a linear relationship.

Turnover frequency of Ser deamination. The sample holder of a UV1800 spectrophotometer (Shimadzu) was heated to 75° C. For the reactions, enzyme and Ser in potassium phosphate buffer (200 mM, pH 8) were added to a quartz cuvette (1 cm path length), such that the total volume was 500 μL, and the final concentrations were 20 μM enzyme and 20 mM Ser. The potassium phosphate buffer was added first, then the cuvette was placed in the sample holder at 75° C. for at least 3 minutes, after which the baseline was measured (300 to 550 nm). Next, the enzyme was added, then the sample was again equilibrated to 75° C. for 3 minutes. After recording the UV-vis absorption spectrum (300 to 550 nm), Ser was added, then the absorption spectrum (300 to 550 nm) was measured every minute for 30 minutes. The change in absorption at 320 nm was correlated with the production of pyruvate using the extinction coefficient ε=20 M$^{-1}$ cm$^{-1}$. Three replicates of each measurement were performed.

| Enzyme | Turnover frequency of Ser deamination (min$^{-1}$) | | | | |
|---|---|---|---|---|---|
| | #1 | #2 | #3 | Average | Std. deviation |
| Pf2B9 | 11.8 | 11.9 | 13.0 | 12.2 | 0.5 |
| Pf5G8 | 2.2 | 1.7 | 2.2 | 2.0 | 0.2 |
| Pf5G8 E104G | 0.7 | 1.0 | 0.8 | 0.9 | 0.1 |
| Pf2A6 | 1.5 | 1.3 | 1.3 | 1.4 | 0.1 |

Turnover frequency of 4-nitrotryptophan production. Using the procedure described above reactions with 0.02 mol % of enzyme were run for 1 hour. The HPLC yield of 4-nitrotryptophan was then determined by HPLC using the calibration described above. Two replicates were performed of each experiment.

| Enzyme | Turnover frequency of 4-nitroTrp (min$^{-1}$) | | | |
|---|---|---|---|---|
| | #1 | #2 | Average | Std. deviation |
| Pf2B9 | 1.34 | 1.16 | 1.25 | 0.09 |
| Pf5G8 | 1.85 | 1.89 | 1.87 | 0.02 |
| Pf5G8 E104G | 3.25 | 3.41 | 3.33 | 0.08 |
| Pf2A6 | 6.79 | 6.86 | 6.82 | 0.03 |

Synthesis and characterization of tryptophan derivatives. Proton and carbon NMR spectra were recorded either on a Bruker 400 MHz (100 MHz) spectrometer equipped with a cryogenic probe, or on a Varian 500 MHz (125 MHz) spectrometer. Fluorine NMR spectra were recorded on a Varian 500 MHz (400 MHz) spectrometer. Proton chemical shifts are reported in ppm (δ) relative to tetramethylsilane and calibrated using the residual solvent resonance (D2O, δ 4.79 ppm, unless specified otherwise). Data are reported as follows: chemical shift (multiplicity [singlet (s), doublet (d), doublet of doublets (dd), doublet of doublets of doublets (ddd), triplet (t), triplet of doubles (td), multiplet (m)], coupling constants [Hz], integration). Carbon NMR spectra were recorded with complete proton decoupling. Carbon chemical shifts are reported in ppm relative to tetramethylsilane and calibrated using the residual solvent proton resonance as an absolute reference, unless specified otherwise. All NMR spectra were recorded at ambient temperature (about 25° C.). Preparative reversed-phase chromatography was performed on a Biotage Isolera One purification system, using C-18 silica as the stationary phase, with methanol as the strong solvent and water (0.1% HCl by weight) as the weak solvent. The gradient of the eluent (∇) is given as % strong solvent/column volume (CV). High-resolution mass spectrometry (HRMS) was conducted with an Agilent 6200 TOF, with samples ionized by electrospray ionization (ESI), or a JMS-600H (JEOL) instrument, with samples ionized by fast atom bombardment (FAB). All starting materials were purchased from commercial sources and used without further purification. Liquid chromatography/mass spectrometry (LCMS) was performed on an Agilent 1290 UPLC-LCMS equipped with a 2.1×50 mm C-18 silica column, using acetonitrile as the strong solvent and 0.1% (v/v) acetic acid/water as the weak solvent. The optical purity of the products was determined by derivatization with N-(5-fluoro-2,4-dinitrophenyl)alanamide (FDNPalanamide).

Screening catalyst panel against substrates. Reactions used the procedure described above. Product formation was approximated using HPLC by comparing the integration of product and substrate peaks at 277 nm. Catalyst loadings for each substrate are indicated in Table 2.

TABLE 2

Tryptophan analogs produced by catalyst panel.
Reactions used 0.02 mol % catalyst loading (maximum 5000 turnovers) and 1.1 equiv Ser relative to indole substrate. Catalyst loading was 0.1 mol % (maximum 1000 turnovers). Reaction gives alkylation at nitrogen.

| Entry | Substrate | R | Catalyst | Isolated Yield (%) |
|---|---|---|---|---|
| 1 | 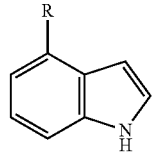 | NO$_2$ | Pf2A6 | 95[b] |
| 2 | | F | Tm2F3 | 97 |
| 3 | | Br | Tm2F3 | 72 |
| 4 | | CN | Tm2F3 I184F | 41 |
| 5 | 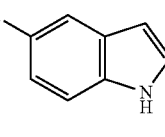 | NO$_2$ | Tm2F3 I184F | 88[b] |
| 6 | | CN | Tm2F3 | 79 |
| 7 | | CONH$_2$ | Tm2F3 | 77 |
| 8 | | B(OH)$_2$ | Pf0A9 | 37 |
| 9 | | I | Pf0A9 | 74[b] |
| 10 | | CF$_3$ | Pf2A6 | 19[b,c] |
| 11 | 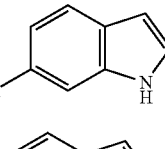 | NO$_2$ | Pf0A9 E104G | 91 |
| 12 | | Cl | Pf0A9 | 98 |
| 13 | | Br | Pf0A9 | 97 |
| 14 | | CN | Pf0A9 | 99 |
| 15 | | B(OH)$_2$ | Pf0A9 | 49 |
| 16 | 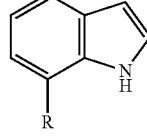 | NO$_2$ | Pf2A6 | 98 |
| 17 | | CN | Pf2A6 | 98 |
| 18 | | Cl | Pf0A9 | 99 |
| 19 | | I | Pf0A9 | 91 |
| 20 | | Br | Pf5G8 | 53 |

HPLC yields of tryptophan analogs with the catalyst panel.

| Substitution | Pf5G8 | Pf2A6 | Tm2F3 | Tm2F3 I184F | Pf0A9 | Pf0A9 E104G |
|---|---|---|---|---|---|---|
| 4-fluoro | 86% | 97% | 100% | 83% | 99% | 38% |
| 4-bromo | 57% | 29% | 69% | 40% | 30% | 0% |
| 4-cyano | 11% | 0% | 10% | 20% | 0% | 8% |
| 5-cyano | 30% | 3% | 81% | 69% | 8% | 3% |
| 5-aminocarbonyl | 55% | 0% | 79% | 79% | 64% | 0% |
| 5-borono | 31% | 0% | 41% | 31% | 44% | 0% |
| 5-iodo | 12% | 29% | 14% | 27% | 60% | 13% |
| 5-trifluoromethyl | 0% | 30% | 0% | 0% | 0% | 0% |
| 6-chloro | 100% | 53% | 100% | 100% | 100% | 47% |
| 6-bromo | 100% | 28% | 100% | 100% | 100% | 38% |
| 6-cyano | 21% | 14% | 6% | 5% | 100% | 73% |
| 6-borono | 3% | 0% | 0% | 2% | 63% | 0% |
| 7-cyano | 68% | 100% | 100% | 79% | 92% | 79% |
| 7-chloro | 56% | 100% | 83% | 80% | 100% | 80% |
| 7-bromo | 63% | 61% | 62% | 63% | 62% | 62% |
| 7-iodo | 87% | 91% | 90% | 63% | 100% | 58% |
| 5,6-dichloro | 100% | 11% | 73% | 55% | 83% | 48% |
| 5-bromo-7-fluoro | 70% | 9% | 89% | 91% | 81% | 83% |
| 5-chloro-7-iodo | 0% | 4% | 20% | 11% | 16% | 19% |

Preparative reactions for product characterization. General procedure: the indole analog (100 μmol) and Ser (110 μmol) were added to a 40-mL reaction vial, followed by DMSO (500 μL). PLP (5 equiv with respect to enzyme) was added as an aqueous solution (1.5 mM), then followed by enough potassium phosphate buffer (200 mM, pH 8) to make the final volume (with enzyme) 10 mL. The vial was sealed, then placed in a water bath that had been equilibrated to 75° C. After 1 min, the enzyme was added. The reaction was kept at 75° C. After 12 hours, the reaction mixture was frozen at −78° C., then the water was removed by lyophilization. The residual solid was washed twice as follows to remove the DMSO: toluene (6 mL) was added, then the suspension was heated to 75° C. After 2 minutes, the suspension was cooled in ice, then the toluene was removed.

The residual solid was suspended in 1:1 CH$_3$CN/1 M aq. HCl, then the volume was reduced in vacuo. This process was repeated once more. Once the organic solvent had been completely removed, the residual aqueous component was loaded onto a C-18 column (12 g) that had been equilibrated to 1% methanol/water (0.1% HCl by mass). The column was washed with 2 column volumes (CV) of this solvent mixture to remove salts and trace DMSO. Finally, the product was eluted with a gradient from 1% to 100% methanol over 10 CV. The fractions containing product were combined, then the organic solvent was removed in vacuo. The residual water was frozen and removed by lyophilization. The products were obtained as the hydrochloride salts.

Gram-scale preparation of 4-nitrotryptophan. The enzyme Pf2A6 was prepared in a 1-L TBamp expression culture according to the procedure described above. For lysis, the cell pellet (10.3 grams) was suspended in 41 mL of 50-mM potassium phosphate buffer (pH 8) that contained 2.18 mg PLP, 41.2 mg HEWL, and 4.12 mg DNase. BugBuster (4.12 mL, 10× concentration) was added, and then the suspension was shaken at 230 RPM and 37° C. After 15 minutes, the suspension was subjected to centrifugation at 4,500×g and 4° C. (5 minutes), and then immersed in a water bath at 75° C. After 30 minutes, the suspension was cooled in ice, then subjected to centrifugation at 15,000×g and 4° C. (15 minutes).

In a 500-mL Erlenmeyer flask, 4-nitroindole (973 mg, 6.00 mmol) and serine (694 mg, 6.60 mmol) were suspended in DMSO (6 mL) and 200-mM potassium phosphate buffer (84 mL, pH 8). Heat-treated lysate (30 mL) was added, then the reaction mixture was immersed in a water bath that was pre-heated to 75° C. After 24 hours, the reaction mixture was cooled in ice, whereupon most of the 4-nitrotryptophan precipitated. The precipitate was collected by filtration, then washed with water and ethyl acetate. To remove insoluble impurities, such as precipitated protein, the product was dissolved in 1:1 1 M aq. HCl/CH$_3$CN, then filtered again. The filtrate was concentrated in vacuo to afford 4-nitrotryptophan as the hydrochloride salt (yellow solid, 1.3 g, 73% yield).

Determination of optical purity. FDNP-alanamide was used as a solution in acetone (33 mM). In a 2-mL vial, the amino acid (0.50 μmol) was dissolved in 1 M aq. NaHCO$_3$ (100 μL). FDNP-alanamide (10 μL, 0.33 μmol) was added, then the vial was placed in an incubator at 37° C. and shaken at 230 RPM. After 2 h, the reaction mixture was allowed to cool to room temperature, then diluted with 1:1 CH$_3$CN/1 M aq. HCl (600 μL). The resulting solution was analyzed directly by LCMS (5% to 95% acetonitrile, monitored using the total ion count filtered for the expected mass). Each amino acid was derivatized with both racemic and enantio-pure FDNP-alanamide for comparison. Absolute stereochemistry was inferred by analogy to L-tryptophan. All products were >99% ee, unless otherwise specified.

A number of embodiments of the invention have been described. Nevertheless, it will be understood that various modifications may be made without departing from the spirit and scope of the invention. Accordingly, other embodiments are within the scope of the following claims.

What is claimed is:

1. An isolated nucleic acid encoding a recombinant tryptophan synthase β-subunit (TrpB) mutant polypeptide comprising a sequence that is at least 85% identical to one of SEQ ID NOS: 2, 4, or 6, wherein the polypeptide comprises at least one activating mutation at a position corresponding to residues 104, 139, 165, 183, 186, 212, and 301 of SEQ ID NO:2.

2. The isolated nucleic acid of claim 1, wherein the recombinant polypeptide comprises a sequence selected from the group consisting of:
   (a) about 85% or more identity to SEQ ID NO:2 and has activating mutations at positions 16, 17, 68, 95, 104, 139, 166, 183, 186, 212, 274, 292, 321 and 384;
   (b) about 85% or more identity to SEQ ID NO:4 and has activating mutations at positions 29, 30, 80, 107, 116, 151, 178, 195, 198, 224, 285, 303, 332, and 395; and
   (c) about 85% or more identity to SEQ ID NO:6 and has activating mutations at positions 18, 19, 69, 96, 105, 140, 167, 184, 187, 213, 274, 292, and 381.

3. The isolated nucleic acid of claim 2, wherein the activating mutations of (a) are selected from the group consisting of I16V, E17G, I68V, F95L, E104G, E104A, M139L, N166D, I183F, V186A, L212P, F274S, T292S, T321A, V384A and any combination thereof relative to SEQ ID NO:2.

4. The isolated nucleic acid of claim 2, wherein the activating mutation of (b) are selected from the group consisting of I29V, P30V, I80V, F107L, E116G, E116A, M151L, N178D, I195F, V198A, I224P, L285S, T303S, T332A, R395A and any combination thereof relative to SEQ ID NO:4.

5. The isolated nucleic acid of claim 2, wherein the activating mutation of (c) are selected from the group consisting of M18V, P19G, I69V, K96L, E105G, E105A, P140L, N167D, I184F, V187A, L213P, L274S, T292S, H381A and any combination thereof relative to SEQ ID NO:6.

6. The isolated nucleic acid of claim 1, wherein the polypeptide comprises:
   a G or A residue at the position corresponding to residue 104 of SEQ ID NO:2; and/or
   an L residue at the position corresponding to residue 139 of SEQ ID NO:2; and/or
   an F residue at the position corresponding to residue 165 of SEQ ID NO:2; and/or
   an F residue at the position corresponding to residue 183 of SEQ ID NO:2; and/or
   an A residue at the position corresponding to residue 186 of SEQ ID NO:2; and/or
   a P residue at the position corresponding to residue 212 of SEQ ID NO:2; and/or an H residue at the position corresponding to residue 301 of SEQ ID NO:2.

7. The isolated nucleic acid of claim 1, wherein the polypeptide further comprises one or more activating mutations at positions corresponding to residues 16, 17, 68, 95, 274, 292, 321 and 384 of SEQ ID NO:2.

8. The isolated nucleic acid of claim 1, wherein the polypeptide is at least 85% identical to SEQ ID NO: 2 and is selected from the group consisting of SEQ ID NOS:14, 16, 18, 20, and 22, or wherein the polypeptide is at least 85% identical to SEQ ID NO: 6 and is selected from the group consisting of SEQ ID NOS: 24 and 26.

9. The isolated nucleic acid of claim 1, wherein the polypeptide comprises:
   (a) an activating mutation at positions corresponding to residue 139 of SEQ ID NO:2;
   (b) an activating mutation at positions corresponding to residues 139, 165, and 301 of SEQ ID NO:2;
   (c) an activating mutation at positions corresponding to residues 139, and 212 of SEQ ID NO:2;
   (d) an activating mutation at positions corresponding to residues 139, 183, and 212 of SEQ ID NO:2; or
   (e) an activating mutation at positions corresponding to residues 139, 183, 186, and 212 of SEQ ID NO:2.

10. The isolated nucleic acid of claim 9, wherein the polypeptide comprises:
   an L residue at the position corresponding to residue 139 of SEQ ID NO:2; and/or
   an F residue at the position corresponding to residue 165 of SEQ ID NO:2; and/or
   an F residue at the position corresponding to residue 183 of SEQ ID NO:2; and/or
   an A residue at the position corresponding to residue 186 of SEQ ID NO:2; and/or
   a P residue at the position corresponding to residue 212 of SEQ ID NO:2; and/or
   an H residue at the position corresponding to residue 301 of SEQ ID NO:2.

11. The isolated nucleic acid of claim 9, wherein the polypeptide further comprises an activating mutation at a position corresponding to residue 104 of SEQ ID NO:2.

12. The isolated nucleic acid of claim 11, wherein the polypeptide further comprises a G or A residue at the position corresponding to residue 104 of SEQ ID NO:2.

13. A vector comprising the nucleic acid molecule of claim 1.

14. The vector of claim 13, which is an expression vector.

15. A host cell transfected with the isolated nucleic acid of claim 1.

16. A host cell transfected with the vector of claim 13.

17. A recombinant nucleic acid consisting of a polynucleotide sequence encoding the polypeptide of SEQ ID NO: 20, 24, or 26.

18. A recombinant nucleic acid consisting of the nucleotide sequence of SEQ ID NO: 19, 23, or 25.

* * * * *

SEQUENCE LISTING

<160> NUMBER OF SEQ IDS NOS: 26

<210> SEQ ID NO 1
<211> LENGTH: 1191
<212> TYPE: DNA
<213> ORGANISM: Pyrococcus furiosus
<220> FEATURE:
<221> NAME/KEY: CDS
<222> LOCATION: (1)..(1191)

<400> SEQUENCE: 1

```
atg tgg ttc ggt gaa ttt ggt ggt cag tac gtg cca gaa acg ctg att      48
Met Trp Phe Gly Glu Phe Gly Gly Gln Tyr Val Pro Glu Thr Leu Ile
1               5                   10                  15 gaa ccg ctg aaa gag ctg gaa aaa gct tac aaa cgt ttc aaa gat gac      96
Glu Pro Leu Lys Glu Leu Glu Lys Ala Tyr Lys Arg Phe Lys Asp Asp
            20                  25                  30 gaa gaa ttc aat cgt caa ctg aat tac tac ctg aaa acc tgg gca ggt     144
Glu Glu Phe Asn Arg Gln Leu Asn Tyr Tyr Leu Lys Thr Trp Ala Gly
        35                  40                  45 cgt cca acc cca ctg tac tac gca aaa cgc ctg act gaa aaa atc ggt     192
Arg Pro Thr Pro Leu Tyr Tyr Ala Lys Arg Leu Thr Glu Lys Ile Gly
    50                  55                  60 ggt gct aaa atc tac ctg aaa cgt gaa gac ctg gtt cac ggt ggt gca     240
Gly Ala Lys Ile Tyr Leu Lys Arg Glu Asp Leu Val His Gly Gly Ala
65                  70                  75                  80 cac aag acc aac aac gcc atc ggt cag gca ctg ctg gca aag ttc atg     288
His Lys Thr Asn Asn Ala Ile Gly Gln Ala Leu Leu Ala Lys Phe Met
                85                  90                  95 ggt aaa act cgt ctg atc gct gag acc ggt gct ggt cag cac ggc gta     336
Gly Lys Thr Arg Leu Ile Ala Glu Thr Gly Ala Gly Gln His Gly Val
            100                 105                 110 gcg act gca atg gct ggt gca ctg ctg ggc atg aaa gtg gac att tac     384
Ala Thr Ala Met Ala Gly Ala Leu Leu Gly Met Lys Val Asp Ile Tyr
        115                 120                 125 atg ggt gct gag gac gta gaa cgt cag aaa atg aac gta ttc cgt atg     432
Met Gly Ala Glu Asp Val Glu Arg Gln Lys Met Asn Val Phe Arg Met
    130                 135                 140 aag ctg ctg ggt gca aac gta att cca gtt aac tcc ggt tct cgc acc     480
Lys Leu Leu Gly Ala Asn Val Ile Pro Val Asn Ser Gly Ser Arg Thr
145                 150                 155                 160 ctg aaa gac gca atc aac gag gct ctg cgt gat tgg gtg gct act ttt     528
Leu Lys Asp Ala Ile Asn Glu Ala Leu Arg Asp Trp Val Ala Thr Phe
                165                 170                 175 gaa tac acc cac tac ctg atc ggt tcc gtg gtc ggt cca cat ccg tat     576
Glu Tyr Thr His Tyr Leu Ile Gly Ser Val Val Gly Pro His Pro Tyr
            180                 185                 190 ccg acc atc gtt cgt gat ttt cag tct gtt atc ggt cgt gag gct aaa     624
Pro Thr Ile Val Arg Asp Phe Gln Ser Val Ile Gly Arg Glu Ala Lys
        195                 200                 205 gcg cag atc ctg gag gct gaa ggt cag ctg cca gat gta atc gtt gct     672
Ala Gln Ile Leu Glu Ala Glu Gly Gln Leu Pro Asp Val Ile Val Ala
    210                 215                 220 tgt gtt ggt ggt ggc tct aac gcg atg ggt atc ttt tac ccg ttc gtg     720
Cys Val Gly Gly Gly Ser Asn Ala Met Gly Ile Phe Tyr Pro Phe Val
225                 230                 235                 240 aac gac aaa aaa gtt aag ctg gtt ggc gtt gag gct ggt ggt aaa ggc     768
Asn Asp Lys Lys Val Lys Leu Val Gly Val Glu Ala Gly Gly Lys Gly
                245                 250                 255 ctg gaa tct ggt aag cat tcc gct agc ctg aac gca ggt cag gtt ggt     816
Leu Glu Ser Gly Lys His Ser Ala Ser Leu Asn Ala Gly Gln Val Gly
```

```
                 260                 265                 270
gtg ttc cat ggc atg ctg tcc tac ttt ctg cag gac gaa gaa ggt cag        864
Val Phe His Gly Met Leu Ser Tyr Phe Leu Gln Asp Glu Glu Gly Gln
            275                 280                 285 atc aaa cca act cac tcc atc gca cca ggt ctg gat tat cca ggt gtt        912
Ile Lys Pro Thr His Ser Ile Ala Pro Gly Leu Asp Tyr Pro Gly Val
290                 295                 300 ggt cca gaa cac gct tac ctg aaa aaa att cag cgt gct gaa tac gtg        960
Gly Pro Glu His Ala Tyr Leu Lys Lys Ile Gln Arg Ala Glu Tyr Val
305                 310                 315                 320 act gta acc gat gaa gaa gca ctg aaa gcg ttc cat gaa ctg agc cgt       1008
Thr Val Thr Asp Glu Glu Ala Leu Lys Ala Phe His Glu Leu Ser Arg
                325                 330                 335 acc gaa ggt atc atc cca gct ctg gaa tct gcg cat gct gtg gct tac       1056
Thr Glu Gly Ile Ile Pro Ala Leu Glu Ser Ala His Ala Val Ala Tyr
            340                 345                 350 gct atg aaa ctg gct aag gaa atg tct cgt gat gag atc atc atc gta       1104
Ala Met Lys Leu Ala Lys Glu Met Ser Arg Asp Glu Ile Ile Ile Val
        355                 360                 365 aac ctg tct ggt cgt ggt gac aaa gac ctg gat att gtt ctg aaa gtg       1152
Asn Leu Ser Gly Arg Gly Asp Lys Asp Leu Asp Ile Val Leu Lys Val
370                 375                 380 tct ggc aac gtg ctc gag cac cat cac cat cac cat tga                   1191
Ser Gly Asn Val Leu Glu His His His His His His
385                 390                 395
```

<210> SEQ ID NO 2
<211> LENGTH: 396
<212> TYPE: PRT
<213> ORGANISM: Pyrococcus furiosus

<400> SEQUENCE: 2

```
Met Trp Phe Gly Glu Phe Gly Gly Gln Tyr Val Pro Glu Thr Leu Ile
1               5                   10                  15

Glu Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
        35                  40                  45

Arg Pro Thr Pro Leu Tyr Tyr Ala Lys Arg Leu Thr Glu Lys Ile Gly
    50                  55                  60

Gly Ala Lys Ile Tyr Leu Lys Arg Glu Asp Leu Val His Gly Gly Ala
65                  70                  75                  80

His Lys Thr Asn Asn Ala Ile Gly Gln Ala Leu Leu Ala Lys Phe Met
                85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Met Asn Val Phe Arg Met
    130                 135                 140

Lys Leu Leu Gly Ala Asn Val Ile Pro Val Asn Ser Gly Ser Arg Thr
145                 150                 155                 160

Leu Lys Asp Ala Ile Asn Glu Ala Leu Arg Asp Trp Val Ala Thr Phe
                165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
```

```
            195                 200                 205
Ala Gln Ile Leu Glu Ala Glu Gly Gln Leu Pro Asp Val Ile Val Ala
        210                 215                 220

Cys Val Gly Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
            260                 265                 270

Val Phe His Gly Met Leu Ser Tyr Phe Leu Gln Asp Glu Glu Gly Gln
        275                 280                 285

Ile Lys Pro Thr His Ser Ile Ala Pro Gly Leu Asp Tyr Pro Gly Val
    290                 295                 300

Gly Pro Glu His Ala Tyr Leu Lys Lys Ile Gln Arg Ala Glu Tyr Val
305                 310                 315                 320

Thr Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
        355                 360                 365

Asn Leu Ser Gly Arg Gly Asp Lys Asp Leu Asp Ile Val Leu Lys Val
    370                 375                 380

Ser Gly Asn Val Leu Glu His His His His His His
385                 390                 395

<210> SEQ ID NO 3
<211> LENGTH: 1218
<212> TYPE: DNA
<213> ORGANISM: Archaeoglobus fulgidus
<220> FEATURE:
<221> NAME/KEY: CDS
<222> LOCATION: (1)..(1218)

<400> SEQUENCE: 3 atg cgt tgc tgg ctg gaa aac ctg tct ggc ggt cgt aaa atg aag ttt      48
Met Arg Cys Trp Leu Glu Asn Leu Ser Gly Gly Arg Lys Met Lys Phe
1               5                   10                  15 ggt gag ttt ggc ggt cgt ttc gtt ccg gag gta ctg atc cca ccg ctg      96
Gly Glu Phe Gly Gly Arg Phe Val Pro Glu Val Leu Ile Pro Pro Leu
                20                  25                  30 gaa gaa ctg gaa aaa gca tat gac cgc ttt aaa gat gat gag gaa ttt     144
Glu Glu Leu Glu Lys Ala Tyr Asp Arg Phe Lys Asp Asp Glu Glu Phe
            35                  40                  45 aaa gca cgt ctg gaa tac tac ctg aaa tcc tat gca ggt cgt ccg acc     192
Lys Ala Arg Leu Glu Tyr Tyr Leu Lys Ser Tyr Ala Gly Arg Pro Thr
        50                  55                  60 cca ctg tac ttc gct gag aac ctg agc cgt gaa ctg ggc gtc aaa atc     240
Pro Leu Tyr Phe Ala Glu Asn Leu Ser Arg Glu Leu Gly Val Lys Ile
65                  70                  75                  80 tat ctg aaa cgc gaa gac ctg ctg cat ggt ggt gcg cac aaa atc aac     288
Tyr Leu Lys Arg Glu Asp Leu Leu His Gly Gly Ala His Lys Ile Asn
                85                  90                  95 aat acc atc ggt caa gcg ctg ctg gcg aaa ttc atg ggt aaa aag cgt     336
Asn Thr Ile Gly Gln Ala Leu Leu Ala Lys Phe Met Gly Lys Lys Arg
            100                 105                 110 gtt att gcg gaa acc ggt gca ggt cag cac ggt gtg gcg act gcg atg     384
Val Ile Ala Glu Thr Gly Ala Gly Gln His Gly Val Ala Thr Ala Met
```

```
              115                 120                 125
gct gcg gca ctg ctg ggc ctg gaa gcg gaa att tat atg ggt gct gaa      432
Ala Ala Ala Leu Leu Gly Leu Glu Ala Glu Ile Tyr Met Gly Ala Glu
    130                 135                 140 gac tat gag cgc caa aaa atg aac gtg ttt cgt atg gaa ctg ctg ggt      480
Asp Tyr Glu Arg Gln Lys Met Asn Val Phe Arg Met Glu Leu Leu Gly
145                 150                 155                 160 gcc aaa gtc acc gct gta gaa agc ggt tcc cgt acc ctg aaa gac gca      528
Ala Lys Val Thr Ala Val Glu Ser Gly Ser Arg Thr Leu Lys Asp Ala
                165                 170                 175 atc aac gag gca ctg cgt gac tgg gtg gaa tct ttc gaa cac act cac      576
Ile Asn Glu Ala Leu Arg Asp Trp Val Glu Ser Phe Glu His Thr His
            180                 185                 190 tac ctg atc ggt tct gta gta ggt ccg cat ccg ttc ccg act atc gtc      624
Tyr Leu Ile Gly Ser Val Val Gly Pro His Pro Phe Pro Thr Ile Val
        195                 200                 205 cgc gac ttc caa gct gtg atc ggc aag gag gca cgc cgt cag atc atc      672
Arg Asp Phe Gln Ala Val Ile Gly Lys Glu Ala Arg Arg Gln Ile Ile
    210                 215                 220 gaa gcg gaa ggt ggt atg ccg gat gct atc atc gcg tgc gta ggc ggt      720
Glu Ala Glu Gly Gly Met Pro Asp Ala Ile Ile Ala Cys Val Gly Gly
225                 230                 235                 240 ggc tcc aac gct atg ggc atc ttc cac ccg ttc ctg aac gac gac gta      768
Gly Ser Asn Ala Met Gly Ile Phe His Pro Phe Leu Asn Asp Asp Val
                245                 250                 255 cgt ctg att ggt gta gaa gct ggc ggt gaa ggt atc gaa tct ggt cgt      816
Arg Leu Ile Gly Val Glu Ala Gly Gly Glu Gly Ile Glu Ser Gly Arg
            260                 265                 270 cat tcc gca agc ctg acc gct ggc tct aaa ggt gtt ctg cac ggt atg      864
His Ser Ala Ser Leu Thr Ala Gly Ser Lys Gly Val Leu His Gly Met
        275                 280                 285 ctg agc tat ttc ctg cag gac gaa gag ggt atg atg ctg gac acc cac      912
Leu Ser Tyr Phe Leu Gln Asp Glu Glu Gly Met Met Leu Asp Thr His
    290                 295                 300 tcc gta tct gca ggt ctg gat tat ccg ggt gtt ggt ccg gaa cac gcc      960
Ser Val Ser Ala Gly Leu Asp Tyr Pro Gly Val Gly Pro Glu His Ala
305                 310                 315                 320 tac ctg aag gaa acg ggt cgt tgt gag tac gtt acc gta aat gac gaa     1008
Tyr Leu Lys Glu Thr Gly Arg Cys Glu Tyr Val Thr Val Asn Asp Glu
                325                 330                 335 gaa gcg ctg cgt gct ttc aaa acc ctg tcc aaa ctg gaa ggt atc att     1056
Glu Ala Leu Arg Ala Phe Lys Thr Leu Ser Lys Leu Glu Gly Ile Ile
            340                 345                 350 cct gcg ctg gaa tcc gct cac gcc att gca tat gct atg aaa atg gcc     1104
Pro Ala Leu Glu Ser Ala His Ala Ile Ala Tyr Ala Met Lys Met Ala
        355                 360                 365 gag gaa atg cag cgt gat gat gtg ctg gtt gta aac ctg tcc ggt cgt     1152
Glu Glu Met Gln Arg Asp Asp Val Leu Val Val Asn Leu Ser Gly Arg
    370                 375                 380 ggc gat aaa gat atg gac atc gta cgt cgt cgt ctg gct ctc gag cac     1200
Gly Asp Lys Asp Met Asp Ile Val Arg Arg Arg Leu Ala Leu Glu His
385                 390                 395                 400 cac cac cac cac cac tga                                             1218
His His His His His
                405

<210> SEQ ID NO 4
<211> LENGTH: 405
<212> TYPE: PRT
<213> ORGANISM: Archaeoglobus fulgidus
```

<400> SEQUENCE: 4

```
Met Arg Cys Trp Leu Glu Asn Leu Ser Gly Gly Arg Lys Met Lys Phe
1               5                   10                  15
Gly Glu Phe Gly Gly Arg Phe Val Pro Glu Val Leu Ile Pro Pro Leu
            20                  25                  30
Glu Glu Leu Glu Lys Ala Tyr Asp Arg Phe Lys Asp Asp Glu Glu Phe
        35                  40                  45
Lys Ala Arg Leu Glu Tyr Tyr Leu Lys Ser Tyr Ala Gly Arg Pro Thr
50                  55                  60
Pro Leu Tyr Phe Ala Glu Asn Leu Ser Arg Glu Leu Gly Val Lys Ile
65                  70                  75                  80
Tyr Leu Lys Arg Glu Asp Leu Leu His Gly Gly Ala His Lys Ile Asn
                85                  90                  95
Asn Thr Ile Gly Gln Ala Leu Leu Ala Lys Phe Met Gly Lys Lys Arg
            100                 105                 110
Val Ile Ala Glu Thr Gly Ala Gly Gln His Gly Val Ala Thr Ala Met
        115                 120                 125
Ala Ala Ala Leu Leu Gly Leu Glu Ala Glu Ile Tyr Met Gly Ala Glu
130                 135                 140
Asp Tyr Glu Arg Gln Lys Met Asn Val Phe Arg Met Glu Leu Leu Gly
145                 150                 155                 160
Ala Lys Val Thr Ala Val Glu Ser Gly Ser Arg Thr Leu Lys Asp Ala
                165                 170                 175
Ile Asn Glu Ala Leu Arg Asp Trp Val Glu Ser Phe Glu His Thr His
            180                 185                 190
Tyr Leu Ile Gly Ser Val Val Gly Pro His Pro Phe Pro Thr Ile Val
        195                 200                 205
Arg Asp Phe Gln Ala Val Ile Gly Lys Glu Ala Arg Arg Gln Ile Ile
210                 215                 220
Glu Ala Glu Gly Gly Met Pro Asp Ala Ile Ile Ala Cys Val Gly Gly
225                 230                 235                 240
Gly Ser Asn Ala Met Gly Ile Phe His Pro Phe Leu Asn Asp Asp Val
                245                 250                 255
Arg Leu Ile Gly Val Glu Ala Gly Gly Glu Gly Ile Glu Ser Gly Arg
            260                 265                 270
His Ser Ala Ser Leu Thr Ala Gly Ser Lys Gly Val Leu His Gly Met
        275                 280                 285
Leu Ser Tyr Phe Leu Gln Asp Glu Glu Gly Met Met Leu Asp Thr His
290                 295                 300
Ser Val Ser Ala Gly Leu Asp Tyr Pro Gly Val Gly Pro Glu His Ala
305                 310                 315                 320
Tyr Leu Lys Glu Thr Gly Arg Cys Glu Tyr Val Thr Val Asn Asp Glu
                325                 330                 335
Glu Ala Leu Arg Ala Phe Lys Thr Leu Ser Lys Leu Glu Gly Ile Ile
            340                 345                 350
Pro Ala Leu Glu Ser Ala His Ala Ile Ala Tyr Ala Met Lys Met Ala
        355                 360                 365
Glu Glu Met Gln Arg Asp Val Leu Val Asn Leu Ser Gly Arg
370                 375                 380
Gly Asp Lys Asp Met Asp Ile Val Arg Arg Leu Ala Leu Glu His
385                 390                 395                 400
His His His His His
```

<210> SEQ ID NO 5
<211> LENGTH: 1194
<212> TYPE: DNA
<213> ORGANISM: Thermotoga maritima
<220> FEATURE:
<221> NAME/KEY: CDS
<222> LOCATION: (1)..(1194)

<400> SEQUENCE: 5

| | | | | | | | | | | | | | | | | |
|---|---|---|---|---|---|---|---|---|---|---|---|---|---|---|---|---|
| atg | aaa | ggc | tac | ttc | ggt | ccg | tac | ggt | ggc | cag | tac | gtg | ccg | gaa | atc | 48 |
| Met | Lys | Gly | Tyr | Phe | Gly | Pro | Tyr | Gly | Gly | Gln | Tyr | Val | Pro | Glu | Ile | |
| 1 | | | | 5 | | | | | 10 | | | | | 15 | | |
| ctg | atg | cca | gct | ctg | gaa | gaa | ctg | gaa | gct | gcg | tac | gaa | gaa | atc | atg | 96 |
| Leu | Met | Pro | Ala | Leu | Glu | Glu | Leu | Glu | Ala | Ala | Tyr | Glu | Glu | Ile | Met | |
| | | | 20 | | | | | 25 | | | | | 30 | | | |
| aaa | gat | gag | tct | ttc | tgg | aaa | gaa | ttc | aat | gac | ctg | ctg | cgc | gat | tat | 144 |
| Lys | Asp | Glu | Ser | Phe | Trp | Lys | Glu | Phe | Asn | Asp | Leu | Leu | Arg | Asp | Tyr | |
| | | | 35 | | | | | 40 | | | | 45 | | | | |
| gcg | ggt | cgt | ccg | act | ccg | ctg | tac | ttc | gca | cgt | cgt | ctg | tcc | gaa | aaa | 192 |
| Ala | Gly | Arg | Pro | Thr | Pro | Leu | Tyr | Phe | Ala | Arg | Arg | Leu | Ser | Glu | Lys | |
| | 50 | | | | | 55 | | | | | 60 | | | | | |
| tac | ggt | gct | cgc | atc | tat | ctg | aaa | cgt | gaa | gac | ctg | ctg | cat | act | ggt | 240 |
| Tyr | Gly | Ala | Arg | Ile | Tyr | Leu | Lys | Arg | Glu | Asp | Leu | Leu | His | Thr | Gly | |
| 65 | | | | | 70 | | | | | 75 | | | | | 80 | |
| gcg | cat | aaa | atc | aat | aac | gct | atc | ggc | cag | gtt | ctg | ctg | gca | aaa | aaa | 288 |
| Ala | His | Lys | Ile | Asn | Asn | Ala | Ile | Gly | Gln | Val | Leu | Leu | Ala | Lys | Lys | |
| | | | | 85 | | | | | 90 | | | | | 95 | | |
| atg | ggc | aaa | acc | cgt | atc | att | gct | gaa | acg | ggt | gct | ggt | cag | cac | ggc | 336 |
| Met | Gly | Lys | Thr | Arg | Ile | Ile | Ala | Glu | Thr | Gly | Ala | Gly | Gln | His | Gly | |
| | | | 100 | | | | | 105 | | | | | 110 | | | |
| gta | gca | act | gct | acc | gca | gca | gcg | ctg | ttc | ggt | atg | gaa | tgt | gta | atc | 384 |
| Val | Ala | Thr | Ala | Thr | Ala | Ala | Ala | Leu | Phe | Gly | Met | Glu | Cys | Val | Ile | |
| | | | 115 | | | | | 120 | | | | | 125 | | | |
| tat | atg | ggc | gaa | gaa | gac | acg | atc | cgc | cag | aaa | ccg | aac | gtt | gaa | cgt | 432 |
| Tyr | Met | Gly | Glu | Glu | Asp | Thr | Ile | Arg | Gln | Lys | Pro | Asn | Val | Glu | Arg | |
| | 130 | | | | | 135 | | | | | 140 | | | | | |
| atg | aaa | ctg | ctg | ggt | gct | aaa | gtt | gta | ccg | gta | aaa | tcc | ggt | agc | cgt | 480 |
| Met | Lys | Leu | Leu | Gly | Ala | Lys | Val | Val | Pro | Val | Lys | Ser | Gly | Ser | Arg | |
| 145 | | | | | 150 | | | | | 155 | | | | | 160 | |
| acc | ctg | aaa | gac | gca | att | aac | gaa | gct | ctg | cgt | gac | tgg | att | acc | aac | 528 |
| Thr | Leu | Lys | Asp | Ala | Ile | Asn | Glu | Ala | Leu | Arg | Asp | Trp | Ile | Thr | Asn | |
| | | | | 165 | | | | | 170 | | | | | 175 | | |
| ctg | cag | acc | acc | tat | tac | gtg | atc | ggc | tct | gtg | gtt | ggt | ccg | cat | cca | 576 |
| Leu | Gln | Thr | Thr | Tyr | Tyr | Val | Ile | Gly | Ser | Val | Val | Gly | Pro | His | Pro | |
| | | | 180 | | | | | 185 | | | | | 190 | | | |
| tat | ccg | att | atc | gta | cgt | aac | ttc | caa | aag | gtt | atc | ggc | gaa | gag | acc | 624 |
| Tyr | Pro | Ile | Ile | Val | Arg | Asn | Phe | Gln | Lys | Val | Ile | Gly | Glu | Glu | Thr | |
| | | | 195 | | | | | 200 | | | | | 205 | | | |
| aaa | aaa | cag | att | ctg | gaa | aaa | gaa | ggc | cgt | ctg | ccg | gac | tac | atc | gtt | 672 |
| Lys | Lys | Gln | Ile | Leu | Glu | Lys | Glu | Gly | Arg | Leu | Pro | Asp | Tyr | Ile | Val | |
| | 210 | | | | | 215 | | | | | 220 | | | | | |
| gcg | tgc | gtg | ggt | ggt | ggt | tct | aac | gct | gcc | ggt | atc | ttc | tat | ccg | ttt | 720 |
| Ala | Cys | Val | Gly | Gly | Gly | Ser | Asn | Ala | Ala | Gly | Ile | Phe | Tyr | Pro | Phe | |
| 225 | | | | | 230 | | | | | 235 | | | | | 240 | |
| atc | gat | tct | ggt | gtg | aag | ctg | atc | ggc | gta | gaa | gcc | ggt | ggc | gaa | ggt | 768 |
| Ile | Asp | Ser | Gly | Val | Lys | Leu | Ile | Gly | Val | Glu | Ala | Gly | Gly | Glu | Gly | |
| | | | | 245 | | | | | 250 | | | | | 255 | | |
| ctg | gaa | acc | ggt | aaa | cat | gcg | gct | tct | ctg | ctg | aaa | ggt | aaa | atc | ggc | 816 |
| Leu | Glu | Thr | Gly | Lys | His | Ala | Ala | Ser | Leu | Leu | Lys | Gly | Lys | Ile | Gly | |

```
tac ctg cac ggt tct aag acg ttc gtt ctg cag gat gac tgg ggt caa    864
Tyr Leu His Gly Ser Lys Thr Phe Val Leu Gln Asp Asp Trp Gly Gln
            275                 280                 285 gtt cag gtg acg cac tcc gtc tcc gct ggc ctg gac tac tcc ggt gtc    912
Val Gln Val Thr His Ser Val Ser Ala Gly Leu Asp Tyr Ser Gly Val
        290                 295                 300 ggt ccg gaa cac gcc tat tgg cgt gag acc ggt aaa gtg ctg tac gat    960
Gly Pro Glu His Ala Tyr Trp Arg Glu Thr Gly Lys Val Leu Tyr Asp
305                 310                 315                 320 gct gtg acc gat gaa gaa gct ctg gac gca ttc atc gaa ctg tct cgc   1008
Ala Val Thr Asp Glu Glu Ala Leu Asp Ala Phe Ile Glu Leu Ser Arg
                325                 330                 335 ctg gaa ggc atc atc cca gcc ctg gag tct tct cac gca ctg gct tat   1056
Leu Glu Gly Ile Ile Pro Ala Leu Glu Ser Ser His Ala Leu Ala Tyr
            340                 345                 350 ctg aag aag atc aac atc aag ggt aaa gtt gtg gtg gtt aat ctg tct   1104
Leu Lys Lys Ile Asn Ile Lys Gly Lys Val Val Val Val Asn Leu Ser
        355                 360                 365 ggt cgt ggt gac aag gat ctg gaa tct gta ctg aac cac ccg tat gtt   1152
Gly Arg Gly Asp Lys Asp Leu Glu Ser Val Leu Asn His Pro Tyr Val
370                 375                 380 cgc gaa cgc atc cgc ctc gag cac cac cac cac cac cac tga           1194
Arg Glu Arg Ile Arg Leu Glu His His His His His His
385                 390                 395

<210> SEQ ID NO 6
<211> LENGTH: 397
<212> TYPE: PRT
<213> ORGANISM: Thermotoga maritima

<400> SEQUENCE: 6

Met Lys Gly Tyr Phe Gly Pro Tyr Gly Gly Gln Tyr Val Pro Glu Ile
1               5                   10                  15

Leu Met Pro Ala Leu Glu Glu Leu Glu Ala Ala Tyr Glu Glu Ile Met
            20                  25                  30

Lys Asp Glu Ser Phe Trp Lys Glu Phe Asn Asp Leu Leu Arg Asp Tyr
        35                  40                  45

Ala Gly Arg Pro Thr Pro Leu Tyr Phe Ala Arg Leu Ser Glu Lys
    50                  55                  60

Tyr Gly Ala Arg Ile Tyr Leu Lys Arg Glu Asp Leu Leu His Thr Gly
65                  70                  75                  80

Ala His Lys Ile Asn Asn Ala Ile Gly Gln Val Leu Leu Ala Lys Lys
                85                  90                  95

Met Gly Lys Thr Arg Ile Ile Ala Glu Thr Gly Ala Gly Gln His Gly
            100                 105                 110

Val Ala Thr Ala Thr Ala Ala Ala Leu Phe Gly Met Glu Cys Val Ile
        115                 120                 125

Tyr Met Gly Glu Glu Asp Thr Ile Arg Gln Lys Pro Asn Val Glu Arg
    130                 135                 140

Met Lys Leu Leu Gly Ala Lys Val Val Pro Val Lys Ser Gly Ser Arg
145                 150                 155                 160

Thr Leu Lys Asp Ala Ile Asn Glu Ala Leu Arg Asp Trp Ile Thr Asn
                165                 170                 175

Leu Gln Thr Thr Tyr Tyr Val Ile Gly Ser Val Val Gly Pro His Pro
            180                 185                 190

Tyr Pro Ile Ile Val Arg Asn Phe Gln Lys Val Ile Gly Glu Glu Thr
```

```
                195                 200                 205
Lys Lys Gln Ile Leu Glu Lys Glu Gly Arg Leu Pro Asp Tyr Ile Val
    210                 215                 220

Ala Cys Val Gly Gly Ser Asn Ala Ala Gly Ile Phe Tyr Pro Phe
225                 230                 235                 240

Ile Asp Ser Gly Val Lys Leu Ile Gly Val Glu Ala Gly Gly Glu Gly
                245                 250                 255

Leu Glu Thr Gly Lys His Ala Ala Ser Leu Leu Lys Gly Lys Ile Gly
            260                 265                 270

Tyr Leu His Gly Ser Lys Thr Phe Val Leu Gln Asp Asp Trp Gly Gln
        275                 280                 285

Val Gln Val Thr His Ser Val Ser Ala Gly Leu Asp Tyr Ser Gly Val
    290                 295                 300

Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg
                325                 330                 335

Leu Glu Gly Ile Ile Pro Ala Leu Glu Ser Ser His Ala Leu Ala Tyr
            340                 345                 350

Leu Lys Lys Ile Asn Ile Lys Gly Lys Val Val Val Asn Leu Ser
        355                 360                 365

Gly Arg Gly Asp Lys Asp Leu Glu Ser Val Leu Asn His Pro Tyr Val
    370                 375                 380

Arg Glu Arg Ile Arg Leu Glu His His His His His His
385                 390                 395

<210> SEQ ID NO 7
<211> LENGTH: 1218
<212> TYPE: DNA
<213> ORGANISM: Escherichia coli
<220> FEATURE:
<221> NAME/KEY: CDS
<222> LOCATION: (1)..(1218)

<400> SEQUENCE: 7 atg act act ctg ctg aac ccg tac ttc ggt gag ttc ggt ggt atg tac      48
Met Thr Thr Leu Leu Asn Pro Tyr Phe Gly Glu Phe Gly Gly Met Tyr
1               5                   10                  15 gtg cca cag atc ctg atg cct gcg ctg cgc cag ctg gag gag gcg ttt      96
Val Pro Gln Ile Leu Met Pro Ala Leu Arg Gln Leu Glu Glu Ala Phe
                20                  25                  30 gtt agc gcc cag aaa gat ccg gag ttc cag gct cag ttc aac gac ctg     144
Val Ser Ala Gln Lys Asp Pro Glu Phe Gln Ala Gln Phe Asn Asp Leu
            35                  40                  45 ctg aaa aac tat gct ggt cgt ccg acc gcg ctg acg aaa tgc cag aac     192
Leu Lys Asn Tyr Ala Gly Arg Pro Thr Ala Leu Thr Lys Cys Gln Asn
        50                  55                  60 atc act gct ggt acg aac acc acc ctg tac ctg aag cgt gag gac ctg     240
Ile Thr Ala Gly Thr Asn Thr Thr Leu Tyr Leu Lys Arg Glu Asp Leu
65                  70                  75                  80 ctg cat ggt ggc gcg cac aaa acc aac cag gtc ctg ggt caa gca ctg     288
Leu His Gly Gly Ala His Lys Thr Asn Gln Val Leu Gly Gln Ala Leu
                85                  90                  95 ctg gca aaa cgt atg ggc aaa act gaa att att gcg gaa acg ggt gca     336
Leu Ala Lys Arg Met Gly Lys Thr Glu Ile Ile Ala Glu Thr Gly Ala
            100                 105                 110 ggt cag cac ggt gta gct tct gcg ctg gcc agc gca ctg ctg ggt ctg     384
Gly Gln His Gly Val Ala Ser Ala Leu Ala Ser Ala Leu Leu Gly Leu
```

|      |     |     |     |     |     |     |     |     |     |     |     |     |     |     |     |      |
|------|-----|-----|-----|-----|-----|-----|-----|-----|-----|-----|-----|-----|-----|-----|-----|------|
|      |     |     | 115 |     |     |     |     | 120 |     |     |     |     | 125 |     |     |      |
| aag  | tgt | cgt | atc | tat | atg | ggt | gcg | aaa | gat | gtg | gag | cgt | cag | tct | ccg | 432  |
| Lys  | Cys | Arg | Ile | Tyr | Met | Gly | Ala | Lys | Asp | Val | Glu | Arg | Gln | Ser | Pro |      |
|      | 130 |     |     |     | 135 |     |     |     |     | 140 |     |     |     |     |     |      |
| aac  | gta | ttc | cgc | atg | cgt | ctg | atg | ggt | gca | gaa | gtg | atc | ccg | gta | cac | 480  |
| Asn  | Val | Phe | Arg | Met | Arg | Leu | Met | Gly | Ala | Glu | Val | Ile | Pro | Val | His |      |
| 145  |     |     |     |     | 150 |     |     |     |     | 155 |     |     |     |     | 160 |      |
| tct  | ggt | tcc | gca | act | ctg | aaa | gac | gca | tgt | aat | gaa | gca | ctg | cgt | gac | 528  |
| Ser  | Gly | Ser | Ala | Thr | Leu | Lys | Asp | Ala | Cys | Asn | Glu | Ala | Leu | Arg | Asp |      |
|      |     |     |     | 165 |     |     |     |     | 170 |     |     |     |     | 175 |     |      |
| tgg  | tcc | ggt | tct | tat | gaa | act | gct | cac | tac | atg | ctg | ggc | acc | gca | gct | 576  |
| Trp  | Ser | Gly | Ser | Tyr | Glu | Thr | Ala | His | Tyr | Met | Leu | Gly | Thr | Ala | Ala |      |
|      |     |     | 180 |     |     |     |     | 185 |     |     |     |     | 190 |     |     |      |
| ggt  | cct | cac | ccg | tac | ccg | acc | atc | gta | cgt | gaa | ttc | cag | cgc | atg | att | 624  |
| Gly  | Pro | His | Pro | Tyr | Pro | Thr | Ile | Val | Arg | Glu | Phe | Gln | Arg | Met | Ile |      |
|      |     | 195 |     |     |     |     | 200 |     |     |     |     | 205 |     |     |     |      |
| ggt  | gaa | gaa | acc | aaa | gcg | cag | atc | ctg | gaa | cgt | gaa | ggt | cgc | ctg | cca | 672  |
| Gly  | Glu | Glu | Thr | Lys | Ala | Gln | Ile | Leu | Glu | Arg | Glu | Gly | Arg | Leu | Pro |      |
|      | 210 |     |     |     | 215 |     |     |     |     | 220 |     |     |     |     |     |      |
| gat  | gcg | gtg | atc | gcg | tgc | gta | ggt | ggt | ggt | tcc | aac | gcg | atc | ggt | atg | 720  |
| Asp  | Ala | Val | Ile | Ala | Cys | Val | Gly | Gly | Gly | Ser | Asn | Ala | Ile | Gly | Met |      |
| 225  |     |     |     | 230 |     |     |     |     | 235 |     |     |     |     | 240 |     |      |
| ttc  | gct | gat | ttc | atc | aac | gaa | acc | aac | gtt | ggc | ctg | att | ggt | gta | gaa | 768  |
| Phe  | Ala | Asp | Phe | Ile | Asn | Glu | Thr | Asn | Val | Gly | Leu | Ile | Gly | Val | Glu |      |
|      |     |     |     | 245 |     |     |     |     | 250 |     |     |     |     | 255 |     |      |
| cca  | ggc | ggc | cac | ggc | att | gaa | act | ggc | gag | cac | ggt | gca | cct | ctg | aaa | 816  |
| Pro  | Gly | Gly | His | Gly | Ile | Glu | Thr | Gly | Glu | His | Gly | Ala | Pro | Leu | Lys |      |
|      |     |     | 260 |     |     |     |     | 265 |     |     |     |     | 270 |     |     |      |
| cac  | ggt | cgc | gta | ggc | att | tac | ttc | ggt | atg | aaa | gct | ccg | atg | atg | cag | 864  |
| His  | Gly | Arg | Val | Gly | Ile | Tyr | Phe | Gly | Met | Lys | Ala | Pro | Met | Met | Gln |      |
|      |     | 275 |     |     |     |     | 280 |     |     |     |     | 285 |     |     |     |      |
| act  | gaa | gac | ggt | cag | atc | gaa | gaa | tct | tac | tcc | att | tct | gca | ggt | ctg | 912  |
| Thr  | Glu | Asp | Gly | Gln | Ile | Glu | Glu | Ser | Tyr | Ser | Ile | Ser | Ala | Gly | Leu |      |
|      | 290 |     |     |     | 295 |     |     |     |     | 300 |     |     |     |     |     |      |
| gac  | ttc | ccg | tct | gtt | ggt | ccg | caa | cac | gca | tat | ctg | aac | tct | acc | ggt | 960  |
| Asp  | Phe | Pro | Ser | Val | Gly | Pro | Gln | His | Ala | Tyr | Leu | Asn | Ser | Thr | Gly |      |
| 305  |     |     |     | 310 |     |     |     |     | 315 |     |     |     |     | 320 |     |      |
| cgt  | gcg | gac | tac | gtg | tct | atc | act | gac | gac | gag | gct | ctg | gag | gcc | ttt | 1008 |
| Arg  | Ala | Asp | Tyr | Val | Ser | Ile | Thr | Asp | Asp | Glu | Ala | Leu | Glu | Ala | Phe |      |
|      |     |     |     | 325 |     |     |     |     | 330 |     |     |     |     | 335 |     |      |
| aaa  | act | ctg | tgc | ctg | cac | gaa | ggt | atc | att | cca | gct | ctg | gaa | tcc | agc | 1056 |
| Lys  | Thr | Leu | Cys | Leu | His | Glu | Gly | Ile | Ile | Pro | Ala | Leu | Glu | Ser | Ser |      |
|      |     |     | 340 |     |     |     |     | 345 |     |     |     |     | 350 |     |     |      |
| cac  | gca | ctg | gca | cac | gca | ctg | aaa | atg | atg | cgt | gaa | aac | cca | gac | aaa | 1104 |
| His  | Ala | Leu | Ala | His | Ala | Leu | Lys | Met | Met | Arg | Glu | Asn | Pro | Asp | Lys |      |
|      |     | 355 |     |     |     |     | 360 |     |     |     |     | 365 |     |     |     |      |
| gaa  | cag | ctg | ctg | gtg | gtt | aac | ctg | agc | ggt | cgt | ggt | gac | aag | gat | atc | 1152 |
| Glu  | Gln | Leu | Leu | Val | Val | Asn | Leu | Ser | Gly | Arg | Gly | Asp | Lys | Asp | Ile |      |
|      | 370 |     |     |     | 375 |     |     |     |     | 380 |     |     |     |     |     |      |
| ttc  | acg | gtt | cac | gac | atc | ctg | aag | gct | cgt | ggt | gaa | atc | ctc | gag | cac | 1200 |
| Phe  | Thr | Val | His | Asp | Ile | Leu | Lys | Ala | Arg | Gly | Glu | Ile | Leu | Glu | His |      |
| 385  |     |     |     |     | 390 |     |     |     |     | 395 |     |     |     |     | 400 |      |
| cac  | cac | cac | cac | cac | tga |     |     |     |     |     |     |     |     |     |     | 1218 |
| His  | His | His | His | His |     |     |     |     |     |     |     |     |     |     |     |      |
|      |     |     |     | 405 |     |     |     |     |     |     |     |     |     |     |     |      |

<210> SEQ ID NO 8
<211> LENGTH: 405
<212> TYPE: PRT
<213> ORGANISM: Escherichia coli -continued

<400> SEQUENCE: 8

```
Met Thr Thr Leu Leu Asn Pro Tyr Phe Gly Glu Phe Gly Gly Met Tyr
1               5                   10                  15

Val Pro Gln Ile Leu Met Pro Ala Leu Arg Gln Leu Glu Glu Ala Phe
            20                  25                  30

Val Ser Ala Gln Lys Asp Pro Glu Phe Gln Ala Gln Phe Asn Asp Leu
        35                  40                  45

Leu Lys Asn Tyr Ala Gly Arg Pro Thr Ala Leu Thr Lys Cys Gln Asn
    50                  55                  60

Ile Thr Ala Gly Thr Asn Thr Thr Leu Tyr Leu Lys Arg Glu Asp Leu
65                  70                  75                  80

Leu His Gly Gly Ala His Lys Thr Asn Gln Val Leu Gly Gln Ala Leu
                85                  90                  95

Leu Ala Lys Arg Met Gly Lys Thr Glu Ile Ile Ala Glu Thr Gly Ala
            100                 105                 110

Gly Gln His Gly Val Ala Ser Ala Leu Ala Ser Ala Leu Leu Gly Leu
        115                 120                 125

Lys Cys Arg Ile Tyr Met Gly Ala Lys Asp Val Glu Arg Gln Ser Pro
    130                 135                 140

Asn Val Phe Arg Met Arg Leu Met Gly Ala Glu Val Ile Pro Val His
145                 150                 155                 160

Ser Gly Ser Ala Thr Leu Lys Asp Ala Cys Asn Glu Ala Leu Arg Asp
                165                 170                 175

Trp Ser Gly Ser Tyr Glu Thr Ala His Tyr Met Leu Gly Thr Ala Ala
            180                 185                 190

Gly Pro His Pro Tyr Pro Thr Ile Val Arg Glu Phe Gln Arg Met Ile
        195                 200                 205

Gly Glu Glu Thr Lys Ala Gln Ile Leu Glu Arg Glu Gly Arg Leu Pro
    210                 215                 220

Asp Ala Val Ile Ala Cys Val Gly Gly Gly Ser Asn Ala Ile Gly Met
225                 230                 235                 240

Phe Ala Asp Phe Ile Asn Glu Thr Asn Val Gly Leu Ile Gly Val Glu
                245                 250                 255

Pro Gly Gly His Gly Ile Glu Thr Gly Glu His Gly Ala Pro Leu Lys
            260                 265                 270

His Gly Arg Val Gly Ile Tyr Phe Gly Met Lys Ala Pro Met Met Gln
        275                 280                 285

Thr Glu Asp Gly Gln Ile Glu Glu Ser Tyr Ser Ile Ser Ala Gly Leu
    290                 295                 300

Asp Phe Pro Ser Val Gly Pro Gln His Ala Tyr Leu Asn Ser Thr Gly
305                 310                 315                 320

Arg Ala Asp Tyr Val Ser Ile Thr Asp Asp Glu Ala Leu Glu Ala Phe
                325                 330                 335

Lys Thr Leu Cys Leu His Glu Gly Ile Ile Pro Ala Leu Glu Ser Ser
            340                 345                 350

His Ala Leu Ala His Ala Leu Lys Met Met Arg Glu Asn Pro Asp Lys
        355                 360                 365

Glu Gln Leu Leu Val Val Asn Leu Ser Gly Arg Gly Asp Lys Asp Ile
    370                 375                 380

Phe Thr Val His Asp Ile Leu Lys Ala Arg Gly Glu Ile Leu Glu His
385                 390                 395                 400

His His His His
```

<210> SEQ ID NO 9
<211> LENGTH: 1191
<212> TYPE: DNA
<213> ORGANISM: Artificial Sequence
<220> FEATURE:
<223> OTHER INFORMATION: PfTrpB2B9
<220> FEATURE:
<221> NAME/KEY: CDS
<222> LOCATION: (1)..(1191)

<400> SEQUENCE: 9

| | | | | | | | | | | | | | | | | |
|---|---|---|---|---|---|---|---|---|---|---|---|---|---|---|---|---|
| atg | tgg | ttc | ggt | gaa | ttt | ggt | ggt | cag | tac | gtg | cca | gaa | acg | ctg | gtt | 48 |
| Met | Trp | Phe | Gly | Glu | Phe | Gly | Gly | Gln | Tyr | Val | Pro | Glu | Thr | Leu | Val | |
| 1 | | | | 5 | | | | | 10 | | | | | 15 | | |
| gga | ccc | ctg | aaa | gag | ctg | gaa | aaa | gct | tac | aaa | cgt | ttc | aaa | gat | gac | 96 |
| Gly | Pro | Leu | Lys | Glu | Leu | Glu | Lys | Ala | Tyr | Lys | Arg | Phe | Lys | Asp | Asp | |
| | | | 20 | | | | | 25 | | | | | 30 | | | |
| gaa | gaa | ttc | aat | cgt | cag | ctg | aat | tac | tac | ctg | aaa | acc | tgg | gca | ggt | 144 |
| Glu | Glu | Phe | Asn | Arg | Gln | Leu | Asn | Tyr | Tyr | Leu | Lys | Thr | Trp | Ala | Gly | |
| | | 35 | | | | | 40 | | | | | 45 | | | | |
| cgt | cca | acc | cca | ctg | tac | tac | gca | aaa | cgc | ctg | act | gaa | aaa | atc | ggt | 192 |
| Arg | Pro | Thr | Pro | Leu | Tyr | Tyr | Ala | Lys | Arg | Leu | Thr | Glu | Lys | Ile | Gly | |
| | 50 | | | | | 55 | | | | | 60 | | | | | |
| ggt | gct | aaa | gtc | tac | ctg | aaa | cgt | gaa | gac | ctg | gtt | cac | ggt | ggt | gca | 240 |
| Gly | Ala | Lys | Val | Tyr | Leu | Lys | Arg | Glu | Asp | Leu | Val | His | Gly | Gly | Ala | |
| 65 | | | | | 70 | | | | | 75 | | | | | 80 | |
| cac | aag | acc | aac | aac | gcc | atc | ggt | cag | gca | ctg | ctg | gca | aag | ctc | atg | 288 |
| His | Lys | Thr | Asn | Asn | Ala | Ile | Gly | Gln | Ala | Leu | Leu | Ala | Lys | Leu | Met | |
| | | | | 85 | | | | | 90 | | | | | 95 | | |
| ggt | aaa | act | cgt | ctg | atc | gct | gag | acc | ggt | gct | ggt | cag | cac | ggc | gta | 336 |
| Gly | Lys | Thr | Arg | Leu | Ile | Ala | Glu | Thr | Gly | Ala | Gly | Gln | His | Gly | Val | |
| | | | 100 | | | | | 105 | | | | | 110 | | | |
| gcg | act | gca | atg | gct | ggt | gca | ctg | ctg | ggc | atg | aaa | gtg | gac | att | tac | 384 |
| Ala | Thr | Ala | Met | Ala | Gly | Ala | Leu | Leu | Gly | Met | Lys | Val | Asp | Ile | Tyr | |
| | | 115 | | | | | 120 | | | | | 125 | | | | |
| atg | ggt | gct | gag | gac | gta | gaa | cgt | cag | aaa | atg | aac | gta | ttc | cgt | atg | 432 |
| Met | Gly | Ala | Glu | Asp | Val | Glu | Arg | Gln | Lys | Met | Asn | Val | Phe | Arg | Met | |
| | 130 | | | | | 135 | | | | | 140 | | | | | |
| aag | ctg | ctg | ggt | gca | aac | gta | att | cca | gtt | aac | tcc | ggt | tct | cgc | acc | 480 |
| Lys | Leu | Leu | Gly | Ala | Asn | Val | Ile | Pro | Val | Asn | Ser | Gly | Ser | Arg | Thr | |
| 145 | | | | | 150 | | | | | 155 | | | | | 160 | |
| ctg | aaa | gac | gca | atc | aac | gag | gct | ctg | cgt | gat | tgg | gtg | gct | act | ttt | 528 |
| Leu | Lys | Asp | Ala | Ile | Asn | Glu | Ala | Leu | Arg | Asp | Trp | Val | Ala | Thr | Phe | |
| | | | | 165 | | | | | 170 | | | | | 175 | | |
| gaa | tac | acc | cac | tac | cta | atc | ggt | tcc | gtg | gtc | ggt | cca | cat | ccg | tat | 576 |
| Glu | Tyr | Thr | His | Tyr | Leu | Ile | Gly | Ser | Val | Val | Gly | Pro | His | Pro | Tyr | |
| | | | 180 | | | | | 185 | | | | | 190 | | | |
| ccg | acc | atc | gtt | cgt | gat | ttt | cag | tct | gtt | atc | ggt | cgt | gag | gct | aaa | 624 |
| Pro | Thr | Ile | Val | Arg | Asp | Phe | Gln | Ser | Val | Ile | Gly | Arg | Glu | Ala | Lys | |
| | | 195 | | | | | 200 | | | | | 205 | | | | |
| gcg | cag | atc | ctg | gag | gct | gaa | ggt | cag | ctg | cca | gat | gta | atc | gtt | gct | 672 |
| Ala | Gln | Ile | Leu | Glu | Ala | Glu | Gly | Gln | Leu | Pro | Asp | Val | Ile | Val | Ala | |
| | 210 | | | | | 215 | | | | | 220 | | | | | |
| tgt | gtt | ggt | ggt | ggc | tct | aac | gcg | atg | ggt | atc | ttt | tac | ccg | ttc | gtg | 720 |
| Cys | Val | Gly | Gly | Gly | Ser | Asn | Ala | Met | Gly | Ile | Phe | Tyr | Pro | Phe | Val | |
| 225 | | | | | 230 | | | | | 235 | | | | | 240 | |
| aac | gac | aaa | aaa | gtt | aag | ctg | gtt | ggc | gtt | gag | gct | ggt | ggt | aaa | ggc | 768 |
| Asn | Asp | Lys | Lys | Val | Lys | Leu | Val | Gly | Val | Glu | Ala | Gly | Gly | Lys | Gly | |
| | | | | 245 | | | | | 250 | | | | | 255 | | |

```
ctg gaa tct ggt aag cat tcc gct agc ctg aac gca ggt cag gtt ggt      816
Leu Glu Ser Gly Lys His Ser Ala Ser Leu Asn Ala Gly Gln Val Gly
        260                 265                 270 gtg tcc cat ggc atg ctg tcc tac ttt ctg cag gac gaa gaa ggt cag      864
Val Ser His Gly Met Leu Ser Tyr Phe Leu Gln Asp Glu Glu Gly Gln
    275                 280                 285 atc aaa cca agc cac tcc atc gca cca ggt ctg gat tat cca ggt gtt      912
Ile Lys Pro Ser His Ser Ile Ala Pro Gly Leu Asp Tyr Pro Gly Val
290                 295                 300 ggt cca gaa cac gct tac ctg aaa aaa att cag cgt gct gaa tac gtg      960
Gly Pro Glu His Ala Tyr Leu Lys Lys Ile Gln Arg Ala Glu Tyr Val
305                 310                 315                 320 gct gta acc gat gaa gaa gca ctg aaa gcg ttc cat gaa ctg agc cgt     1008
Ala Val Thr Asp Glu Glu Ala Leu Lys Ala Phe His Glu Leu Ser Arg
        325                 330                 335 acc gaa ggt atc atc cca gct ctg gaa tct gcg cat gct gtg gct tac     1056
Thr Glu Gly Ile Ile Pro Ala Leu Glu Ser Ala His Ala Val Ala Tyr
    340                 345                 350 gct atg aaa ctg gct aag gaa atg tct cgt gat gag atc atc atc gta     1104
Ala Met Lys Leu Ala Lys Glu Met Ser Arg Asp Glu Ile Ile Ile Val
355                 360                 365 aac ctg tct ggt cgt ggt gac aaa gac ctg gat att gtc ctg aaa gcg     1152
Asn Leu Ser Gly Arg Gly Asp Lys Asp Leu Asp Ile Val Leu Lys Ala
370                 375                 380 tct ggc aac gtg ctc gag cac cac cac cac cac cac tga                 1191
Ser Gly Asn Val Leu Glu His His His His His His
385                 390                 395
```

<210> SEQ ID NO 10
<211> LENGTH: 396
<212> TYPE: PRT
<213> ORGANISM: Artificial Sequence
<220> FEATURE:
<223> OTHER INFORMATION: Synthetic Construct

<400> SEQUENCE: 10

```
Met Trp Phe Gly Glu Phe Gly Gly Gln Tyr Val Pro Glu Thr Leu Val
1               5                   10                  15

Gly Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
        35                  40                  45

Arg Pro Thr Pro Leu Tyr Tyr Ala Lys Arg Leu Thr Glu Lys Ile Gly
    50                  55                  60

Gly Ala Lys Val Tyr Leu Lys Arg Glu Asp Leu Val His Gly Gly Ala
65                  70                  75                  80

His Lys Thr Asn Asn Ala Ile Gly Gln Ala Leu Leu Ala Lys Leu Met
                85                  90                  95

Gly Lys Thr Arg Leu Ile Ala Glu Thr Gly Ala Gly Gln His Gly Val
            100                 105                 110

Ala Thr Ala Met Ala Gly Ala Leu Gly Met Lys Val Asp Ile Tyr
        115                 120                 125

Met Gly Ala Glu Asp Val Glu Arg Gln Lys Met Asn Val Phe Arg Met
    130                 135                 140

Lys Leu Leu Gly Ala Asn Val Ile Pro Val Asn Ser Gly Ser Arg Thr
145                 150                 155                 160

Leu Lys Asp Ala Ile Asn Glu Ala Leu Arg Asp Trp Val Ala Thr Phe
                165                 170                 175
```

```
Glu Tyr Thr His Tyr Leu Ile Gly Ser Val Val Gly Pro His Pro Tyr
                180                 185                 190

Pro Thr Ile Val Arg Asp Phe Gln Ser Val Ile Gly Arg Glu Ala Lys
            195                 200                 205

Ala Gln Ile Leu Glu Ala Glu Gly Gln Leu Pro Asp Val Ile Val Ala
        210                 215                 220

Cys Val Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
            260                 265                 270

Val Ser His Gly Met Leu Ser Tyr Phe Leu Gln Asp Glu Glu Gly Gln
        275                 280                 285

Ile Lys Pro Ser His Ser Ile Ala Pro Gly Leu Asp Tyr Pro Gly Val
    290                 295                 300

Gly Pro Glu His Ala Tyr Leu Lys Lys Ile Gln Arg Ala Glu Tyr Val
305                 310                 315                 320

Ala Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
        355                 360                 365

Asn Leu Ser Gly Arg Gly Asp Lys Asp Leu Asp Ile Val Leu Lys Ala
    370                 375                 380

Ser Gly Asn Val Leu Glu His His His His His His
385                 390                 395

<210> SEQ ID NO 11
<211> LENGTH: 1164
<212> TYPE: DNA
<213> ORGANISM: Artificial Sequence
<220> FEATURE:
<223> OTHER INFORMATION: Pf2B9 L161V
<220> FEATURE:
<221> NAME/KEY: CDS
<222> LOCATION: (1)..(1164)

<400> SEQUENCE: 11 atg tgg ttc ggt gaa ttt ggt ggt cag tac gtg cca gaa acg ctg gtt      48
Met Trp Phe Gly Glu Phe Gly Gly Gln Tyr Val Pro Glu Thr Leu Val
1               5                  10                  15 gga ccc ctg aaa gag ctg gaa aaa gct tac aaa cgt ttc aaa gat gac      96
Gly Pro Leu Lys Glu Leu Glu Lys Ala Tyr Lys Arg Phe Lys Asp Asp
            20                  25                  30 gaa gaa ttc aat cgt cag ctg aat tac tac ctg aaa acc tgg gca ggt     144
Glu Glu Phe Asn Arg Gln Leu Asn Tyr Tyr Leu Lys Thr Trp Ala Gly
        35                  40                  45 cgt cca acc cca ctg tac tac gca aaa cgc ctg act gaa aaa atc ggt     192
Arg Pro Thr Pro Leu Tyr Tyr Ala Lys Arg Leu Thr Glu Lys Ile Gly
    50                  55                  60 ggt gct aaa gtc tac ctg aaa cgt gaa gac ctg gtt cac ggt ggt gca     240
Gly Ala Lys Val Tyr Leu Lys Arg Glu Asp Leu Val His Gly Gly Ala
65                  70                  75                  80 cac aag acc aac aac gcc atc ggt cag gca ctg ctg gca aag ctc atg     288
His Lys Thr Asn Asn Ala Ile Gly Gln Ala Leu Leu Ala Lys Leu Met
                85                  90                  95
```

-continued

| | | |
|---|---|---|
| ggt aaa act cgt ctg atc gct gag acc ggt gct ggt cag cac ggc gta<br>Gly Lys Thr Arg Leu Ile Ala Glu Thr Gly Ala Gly Gln His Gly Val<br>100                                   105                           110 | | 336 |
| gcg act gca atg gct ggt gca ctg ctg ggc atg aaa gtg gac att tac<br>Ala Thr Ala Met Ala Gly Ala Leu Leu Gly Met Lys Val Asp Ile Tyr<br>                115                       120                       125 | | 384 |
| atg ggt gct gag gac gta gaa cgt cag aaa atg aac gta ttc cgt atg<br>Met Gly Ala Glu Asp Val Glu Arg Gln Lys Met Asn Val Phe Arg Met<br>130                                   135                           140 | | 432 |
| aag ctg ctg ggt gca aac gta att cca gtt aac tcc ggt tct cgc acc<br>Lys Leu Leu Gly Ala Asn Val Ile Pro Val Asn Ser Gly Ser Arg Thr<br>145                                   150                           155                           160 | | 480 |
| gtg aaa gac gca atc aac gag gct ctg cgt gat tgg gtg gct act ttt<br>Val Lys Asp Ala Ile Asn Glu Ala Leu Arg Asp Trp Val Ala Thr Phe<br>                         165                       170                       175 | | 528 |
| gaa tac acc cac tac cta atc ggt tcc gtg gtc ggt cca cat ccg tat<br>Glu Tyr Thr His Tyr Leu Ile Gly Ser Val Val Gly Pro His Pro Tyr<br>                         180                       185                       190 | | 576 |
| ccg acc atc gtt cgt gat ttt cag tct gtt atc ggt cgt gag gct aaa<br>Pro Thr Ile Val Arg Asp Phe Gln Ser Val Ile Gly Arg Glu Ala Lys<br>                195                       200                       205 | | 624 |
| gcg cag atc ctg gag gct gaa ggt cag ctg cca gat gta atc gtt gct<br>Ala Gln Ile Leu Glu Ala Glu Gly Gln Leu Pro Asp Val Ile Val Ala<br>210                                   215                           220 | | 672 |
| tgt gtt ggt ggt ggc tct aac gcg atg ggt atc ttt tac ccg ttc gtg<br>Cys Val Gly Gly Gly Ser Asn Ala Met Gly Ile Phe Tyr Pro Phe Val<br>225                                   230                           235                           240 | | 720 |
| aac gac aaa aaa gtt aag ctg gtt ggc gtt gag gct ggt ggt aaa ggc<br>Asn Asp Lys Lys Val Lys Leu Val Gly Val Glu Ala Gly Gly Lys Gly<br>                         245                       250                       255 | | 768 |
| ctg gaa tct ggt aag cat tcc gct agc ctg aac gca ggt cag gtt ggt<br>Leu Glu Ser Gly Lys His Ser Ala Ser Leu Asn Ala Gly Gln Val Gly<br>                         260                       265                       270 | | 816 |
| gtg tcc cat ggc atg ctg tcc tac ttt ctg cag gac gaa gaa ggt cag<br>Val Ser His Gly Met Leu Ser Tyr Phe Leu Gln Asp Glu Glu Gly Gln<br>                275                       280                       285 | | 864 |
| atc aaa cca agc cac tcc atc gca cca ggt ctg gat tat cca ggt gtt<br>Ile Lys Pro Ser His Ser Ile Ala Pro Gly Leu Asp Tyr Pro Gly Val<br>290                                   295                           300 | | 912 |
| ggt cca gaa cac gct tac ctg aaa aaa att cag cgt gct gaa tac gtg<br>Gly Pro Glu His Ala Tyr Leu Lys Lys Ile Gln Arg Ala Glu Tyr Val<br>305                                   310                           315                           320 | | 960 |
| gct gta acc gat gaa gaa gca ctg aaa gcg ttc cat gaa ctg agc cgt<br>Ala Val Thr Asp Glu Glu Ala Leu Lys Ala Phe His Glu Leu Ser Arg<br>                         325                       330                       335 | | 1008 |
| acc gaa ggt atc atc cca gct ctg gaa tct gcg cat gct gtg gct tac<br>Thr Glu Gly Ile Ile Pro Ala Leu Glu Ser Ala His Ala Val Ala Tyr<br>                         340                       345                       350 | | 1056 |
| gct atg aaa ctg gct aag gaa atg tct cgt gat gag atc atc atc gta<br>Ala Met Lys Leu Ala Lys Glu Met Ser Arg Asp Glu Ile Ile Ile Val<br>                355                       360                       365 | | 1104 |
| aac ctg tct ggt cgt ggt gac aaa gac ctg gat att gtc ctg aaa gcg<br>Asn Leu Ser Gly Arg Gly Asp Lys Asp Leu Asp Ile Val Leu Lys Ala<br>370                                   375                           380 | | 1152 |
| tct ggc aac gtg<br>Ser Gly Asn Val<br>385 | | 1164 |

<210> SEQ ID NO 12
<211> LENGTH: 388

<212> TYPE: PRT
<213> ORGANISM: Artificial Sequence
<220> FEATURE:
<223> OTHER INFORMATION: Synthetic Construct

<400> SEQUENCE: 12

```
Met Trp Phe Gly Glu Phe Gly Gly Gln Tyr Val Pro Glu Thr Leu Val
1               5                   10                  15

Gly Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
        35                  40                  45

Arg Pro Thr Pro Leu Tyr Tyr Ala Lys Arg Leu Thr Glu Lys Ile Gly
    50                  55                  60

Gly Ala Lys Val Tyr Leu Lys Arg Glu Asp Leu Val His Gly Gly Ala
65                  70                  75                  80

His Lys Thr Asn Asn Ala Ile Gly Gln Ala Leu Leu Ala Lys Leu Met
                85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Met Asn Val Phe Arg Met
    130                 135                 140

Lys Leu Leu Gly Ala Asn Val Ile Pro Val Asn Ser Gly Ser Arg Thr
145                 150                 155                 160

Val Lys Asp Ala Ile Asn Glu Ala Leu Arg Asp Trp Val Ala Thr Phe
                165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
        195                 200                 205

Ala Gln Ile Leu Glu Ala Glu Gly Gln Leu Pro Asp Val Ile Val Ala
    210                 215                 220

Cys Val Gly Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
            260                 265                 270

Val Ser His Gly Met Leu Ser Tyr Phe Leu Gln Asp Glu Glu Gly Gln
        275                 280                 285

Ile Lys Pro Ser His Ser Ile Ala Pro Gly Leu Asp Tyr Pro Gly Val
    290                 295                 300

Gly Pro Glu His Ala Tyr Leu Lys Lys Ile Gln Arg Ala Glu Tyr Val
305                 310                 315                 320

Ala Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
        355                 360                 365

Asn Leu Ser Gly Arg Gly Asp Lys Asp Leu Asp Ile Val Leu Lys Ala
    370                 375                 380
```

Ser Gly Asn Val
385

<210> SEQ ID NO 13
<211> LENGTH: 1164
<212> TYPE: DNA
<213> ORGANISM: Artificial Sequence
<220> FEATURE:
<223> OTHER INFORMATION: Pf5G8
<220> FEATURE:
<221> NAME/KEY: CDS
<222> LOCATION: (1)..(1164)

<400> SEQUENCE: 13

| | | | | | | | | | | | | | | | | |
|---|---|---|---|---|---|---|---|---|---|---|---|---|---|---|---|---|
| atg | tgg | ttc | ggt | gaa | ttt | ggt | ggt | cag | tac | gtg | cca | gaa | acg | ctg | gtt | 48 |
| Met | Trp | Phe | Gly | Glu | Phe | Gly | Gly | Gln | Tyr | Val | Pro | Glu | Thr | Leu | Val | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gga | ccc | ctg | aaa | gag | ctg | gaa | aaa | gct | tac | aaa | cgt | ttc | aaa | gat | gac | 96 |
| Gly | Pro | Leu | Lys | Glu | Leu | Glu | Lys | Ala | Tyr | Lys | Arg | Phe | Lys | Asp | Asp | |
| | | 20 | | | | | 25 | | | | | 30 | | | | |

| | | | | | | | | | | | | | | | | |
|---|---|---|---|---|---|---|---|---|---|---|---|---|---|---|---|---|
| gaa | gaa | ttc | aat | cgt | cag | ctg | aat | tac | tac | ctg | aaa | acc | tgg | gca | ggt | 144 |
| Glu | Glu | Phe | Asn | Arg | Gln | Leu | Asn | Tyr | Tyr | Leu | Lys | Thr | Trp | Ala | Gly | |
| | | | 35 | | | | | 40 | | | | | 45 | | | |

| | | | | | | | | | | | | | | | | |
|---|---|---|---|---|---|---|---|---|---|---|---|---|---|---|---|---|
| cgt | cca | acc | cca | ctg | tac | tac | gca | aaa | cgc | ctg | act | gaa | aaa | atc | ggt | 192 |
| Arg | Pro | Thr | Pro | Leu | Tyr | Tyr | Ala | Lys | Arg | Leu | Thr | Glu | Lys | Ile | Gly | |
| | 50 | | | | | 55 | | | | | 60 | | | | | |

| | | | | | | | | | | | | | | | | |
|---|---|---|---|---|---|---|---|---|---|---|---|---|---|---|---|---|
| ggt | gct | aaa | gtc | tac | ctg | aaa | cgt | gaa | gac | ctg | gtt | cac | ggt | ggt | gca | 240 |
| Gly | Ala | Lys | Val | Tyr | Leu | Lys | Arg | Glu | Asp | Leu | Val | His | Gly | Gly | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cac | aag | acc | aac | aac | gcc | atc | ggt | cag | gca | ctg | ctg | gca | aag | ctc | atg | 288 |
| His | Lys | Thr | Asn | Asn | Ala | Ile | Gly | Gln | Ala | Leu | Leu | Ala | Lys | Leu | Met | |
| | | | | 85 | | | | | 90 | | | | | 95 | | |

| | | | | | | | | | | | | | | | | |
|---|---|---|---|---|---|---|---|---|---|---|---|---|---|---|---|---|
| ggt | aaa | act | cgt | ctg | atc | gct | gag | acc | ggt | gct | ggt | cag | cac | ggc | gta | 336 |
| Gly | Lys | Thr | Arg | Leu | Ile | Ala | Glu | Thr | Gly | Ala | Gly | Gln | His | Gly | Val | |
| | | | 100 | | | | | 105 | | | | | 110 | | | |

| | | | | | | | | | | | | | | | | |
|---|---|---|---|---|---|---|---|---|---|---|---|---|---|---|---|---|
| gcg | act | gca | atg | gct | ggt | gca | ctg | ctg | ggc | atg | aaa | gtg | gac | att | tac | 384 |
| Ala | Thr | Ala | Met | Ala | Gly | Ala | Leu | Leu | Gly | Met | Lys | Val | Asp | Ile | Tyr | |
| | | | 115 | | | | | 120 | | | | | 125 | | | |

| | | | | | | | | | | | | | | | | |
|---|---|---|---|---|---|---|---|---|---|---|---|---|---|---|---|---|
| atg | ggt | gct | gag | gac | gta | gaa | cgt | cag | aaa | ttg | aac | gta | ttc | cgt | atg | 432 |
| Met | Gly | Ala | Glu | Asp | Val | Glu | Arg | Gln | Lys | Leu | Asn | Val | Phe | Arg | Met | |
| | 130 | | | | | 135 | | | | | 140 | | | | | |

| | | | | | | | | | | | | | | | | |
|---|---|---|---|---|---|---|---|---|---|---|---|---|---|---|---|---|
| aag | ctg | ctg | ggt | gca | aac | gta | att | cca | gtt | aac | tcc | ggt | tct | cgc | acc | 480 |
| Lys | Leu | Leu | Gly | Ala | Asn | Val | Ile | Pro | Val | Asn | Ser | Gly | Ser | Arg | Thr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ctg | aaa | gac | gca | atc | gac | gag | gct | ctg | cgt | gat | tgg | gtg | gct | act | ttt | 528 |
| Leu | Lys | Asp | Ala | Ile | Asp | Glu | Ala | Leu | Arg | Asp | Trp | Val | Ala | Thr | Phe | |
| | | | | 165 | | | | | 170 | | | | | 175 | | |

| | | | | | | | | | | | | | | | | |
|---|---|---|---|---|---|---|---|---|---|---|---|---|---|---|---|---|
| gaa | tac | acc | cac | tac | cta | atc | ggt | tcc | gtg | gtc | ggt | cca | cat | ccg | tat | 576 |
| Glu | Tyr | Thr | His | Tyr | Leu | Ile | Gly | Ser | Val | Val | Gly | Pro | His | Pro | Tyr | |
| | | | 180 | | | | | 185 | | | | | 190 | | | |

| | | | | | | | | | | | | | | | | |
|---|---|---|---|---|---|---|---|---|---|---|---|---|---|---|---|---|
| ccg | acc | atc | gtt | cgt | gat | ttt | cag | tct | gtt | atc | ggt | cgt | gag | gct | aaa | 624 |
| Pro | Thr | Ile | Val | Arg | Asp | Phe | Gln | Ser | Val | Ile | Gly | Arg | Glu | Ala | Lys | |
| | | | 195 | | | | | 200 | | | | | 205 | | | |

| | | | | | | | | | | | | | | | | |
|---|---|---|---|---|---|---|---|---|---|---|---|---|---|---|---|---|
| gcg | cag | atc | ccg | gag | gct | gaa | ggt | cag | ctg | cca | gat | gta | atc | gtt | gct | 672 |
| Ala | Gln | Ile | Pro | Glu | Ala | Glu | Gly | Gln | Leu | Pro | Asp | Val | Ile | Val | Ala | |
| | 210 | | | | | 215 | | | | | 220 | | | | | |

| | | | | | | | | | | | | | | | | |
|---|---|---|---|---|---|---|---|---|---|---|---|---|---|---|---|---|
| tgt | gtt | ggt | ggt | ggc | tct | aac | gcg | atg | ggt | atc | ttt | tac | ccg | ttc | gtg | 720 |
| Cys | Val | Gly | Gly | Gly | Ser | Asn | Ala | Met | Gly | Ile | Phe | Tyr | Pro | Phe | Val | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aac | gac | aaa | aaa | gtt | aag | ctg | gtt | ggc | gtt | gag | gct | ggt | ggt | aaa | ggc | 768 |
| Asn | Asp | Lys | Lys | Val | Lys | Leu | Val | Gly | Val | Glu | Ala | Gly | Gly | Lys | Gly | |
| | | | | 245 | | | | | 250 | | | | | 255 | | |

```
ctg gaa tct ggt aag cat tcc gct agc ctg aac gca ggt cag gtt ggt     816
Leu Glu Ser Gly Lys His Ser Ala Ser Leu Asn Ala Gly Gln Val Gly
        260                 265                 270 gtg tcc cat ggc atg ctg tcc tac ttt ctg cag gac gaa gaa ggt cag     864
Val Ser His Gly Met Leu Ser Tyr Phe Leu Gln Asp Glu Glu Gly Gln
            275                 280                 285 atc aaa cca agc cac tcc atc gca cca ggt ctg gat tat cca ggt gtt     912
Ile Lys Pro Ser His Ser Ile Ala Pro Gly Leu Asp Tyr Pro Gly Val
290                 295                 300 ggt cca gaa cac gct tac ctg aaa aaa att cag cgt gct gaa tac gtg     960
Gly Pro Glu His Ala Tyr Leu Lys Lys Ile Gln Arg Ala Glu Tyr Val
305                 310                 315                 320 gct gta acc gat gaa gaa gca ctg aaa gcg ttc cat gaa ctg agc cgt    1008
Ala Val Thr Asp Glu Glu Ala Leu Lys Ala Phe His Glu Leu Ser Arg
            325                 330                 335 acc gaa ggt atc atc cca gct ctg gaa tct gcg cat gct gtg gct tac    1056
Thr Glu Gly Ile Ile Pro Ala Leu Glu Ser Ala His Ala Val Ala Tyr
                340                 345                 350 gct atg aaa ctg gct aag gaa atg tct cgt gat gag atc atc atc gta    1104
Ala Met Lys Leu Ala Lys Glu Met Ser Arg Asp Glu Ile Ile Ile Val
                    355                 360                 365 aac ctg tct ggt cgt ggt gac aaa gac ctg gat att gtc ctg aaa gcg    1152
Asn Leu Ser Gly Arg Gly Asp Lys Asp Leu Asp Ile Val Leu Lys Ala
370                 375                 380 tct ggc aac gtg                                                    1164
Ser Gly Asn Val
385

<210> SEQ ID NO 14
<211> LENGTH: 388
<212> TYPE: PRT
<213> ORGANISM: Artificial Sequence
<220> FEATURE:
<223> OTHER INFORMATION: Synthetic Construct

<400> SEQUENCE: 14

Met Trp Phe Gly Glu Phe Gly Gly Gln Tyr Val Pro Glu Thr Leu Val
1               5                   10                  15

Gly Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
        35                  40                  45

Arg Pro Thr Pro Leu Tyr Tyr Ala Lys Arg Leu Thr Glu Lys Ile Gly
    50                  55                  60

Gly Ala Lys Val Tyr Leu Lys Arg Glu Asp Leu Val His Gly Gly Ala
65                  70                  75                  80

His Lys Thr Asn Asn Ala Ile Gly Gln Ala Leu Leu Ala Lys Leu Met
                85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Leu Asn Val Phe Arg Met
    130                 135                 140

Lys Leu Leu Gly Ala Asn Val Ile Pro Val Asn Ser Gly Ser Arg Thr
145                 150                 155                 160

Leu Lys Asp Ala Ile Asp Glu Ala Leu Arg Asp Trp Val Ala Thr Phe
                165                 170                 175
```

```
Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
            195                 200                 205

Ala Gln Ile Pro Glu Ala Glu Gly Gln Leu Pro Asp Val Ile Val Ala
210                 215                 220

Cys Val Gly Gly Ser Asn Ala Met Gly Ile Phe Tyr Pro Phe Val
225                 230                 235                 240

Asn Asp Lys Lys Val Lys Leu Val Gly Val Glu Ala Gly Lys Gly
            245                 250                 255

Leu Glu Ser Gly Lys His Ser Ala Ser Leu Asn Ala Gly Gln Val Gly
            260                 265                 270

Val Ser His Gly Met Leu Ser Tyr Phe Leu Gln Asp Glu Glu Gly Gln
            275                 280                 285

Ile Lys Pro Ser His Ser Ile Ala Pro Gly Leu Asp Tyr Pro Gly Val
            290                 295                 300

Gly Pro Glu His Ala Tyr Leu Lys Lys Ile Gln Arg Ala Glu Tyr Val
305                 310                 315                 320

Ala Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
            355                 360                 365

Asn Leu Ser Gly Arg Gly Asp Lys Asp Leu Asp Ile Val Leu Lys Ala
            370                 375                 380

Ser Gly Asn Val
385

<210> SEQ ID NO 15
<211> LENGTH: 1164
<212> TYPE: DNA
<213> ORGANISM: Artificial Sequence
<220> FEATURE:
<223> OTHER INFORMATION: Pf5G8 E104G
<220> FEATURE:
<221> NAME/KEY: CDS
<222> LOCATION: (1)..(1164)

<400> SEQUENCE: 15 atg tgg ttc ggt gaa ttt ggt ggt cag tac gtg cca gaa acg ctg gtt     48
Met Trp Phe Gly Glu Phe Gly Gly Gln Tyr Val Pro Glu Thr Leu Val
1               5                   10                  15 gga ccc ctg aaa gag ctg gaa aaa gct tac aaa cgt ttc aaa gat gac     96
Gly Pro Leu Lys Glu Leu Glu Lys Ala Tyr Lys Arg Phe Lys Asp Asp
                20                  25                  30 gaa gaa ttc aat cgt cag ctg aat tac tac ctg aaa acc tgg gca ggt    144
Glu Glu Phe Asn Arg Gln Leu Asn Tyr Tyr Leu Lys Thr Trp Ala Gly
            35                  40                  45 cgt cca acc cca ctg tac tac gca aaa cgc ctg act gaa aaa atc ggt    192
Arg Pro Thr Pro Leu Tyr Tyr Ala Lys Arg Leu Thr Glu Lys Ile Gly
        50                  55                  60 ggt gct aaa gtc tac ctg aaa cgt gaa gac ctg gtt cac ggt ggt gca    240
Gly Ala Lys Val Tyr Leu Lys Arg Glu Asp Leu Val His Gly Gly Ala
65                  70                  75                  80 cac aag acc aac aac gcc atc ggt cag gca ctg ctg gca aag ctc atg    288
His Lys Thr Asn Asn Ala Ile Gly Gln Ala Leu Leu Ala Lys Leu Met
                85                  90                  95
```

```
ggt aaa act cgt ctg atc gct ggg acc ggt gct ggt cag cac ggc gta      336
Gly Lys Thr Arg Leu Ile Ala Gly Thr Gly Ala Gly Gln His Gly Val
            100                 105                 110 gcg act gca atg gct ggt gca ctg ctg ggc atg aaa gtg gac att tac      384
Ala Thr Ala Met Ala Gly Ala Leu Leu Gly Met Lys Val Asp Ile Tyr
        115                 120                 125 atg ggt gct gag gac gta gaa cgt cag aaa ttg aac gta ttc cgt atg      432
Met Gly Ala Glu Asp Val Glu Arg Gln Lys Leu Asn Val Phe Arg Met
130                 135                 140 aag ctg ctg ggt gca aac gta att cca gtt aac tcc ggt tct cgc acc      480
Lys Leu Leu Gly Ala Asn Val Ile Pro Val Asn Ser Gly Ser Arg Thr
145                 150                 155                 160 ctg aaa gac gca atc gac gag gct ctg cgt gat tgg gtg gct act ttt      528
Leu Lys Asp Ala Ile Asp Glu Ala Leu Arg Asp Trp Val Ala Thr Phe
                165                 170                 175 gaa tac acc cac tac cta atc ggt tcc gtg gtc ggt cca cat ccg tat      576
Glu Tyr Thr His Tyr Leu Ile Gly Ser Val Val Gly Pro His Pro Tyr
            180                 185                 190 ccg acc atc gtt cgt gat ttt cag tct gtt atc ggt cgt gag gct aaa      624
Pro Thr Ile Val Arg Asp Phe Gln Ser Val Ile Gly Arg Glu Ala Lys
        195                 200                 205 gcg cag atc ccg gag gct gaa ggt cag ctg cca gat gta atc gtt gct      672
Ala Gln Ile Pro Glu Ala Glu Gly Gln Leu Pro Asp Val Ile Val Ala
210                 215                 220 tgt gtt ggt ggt ggc tct aac gcg atg ggt atc ttt tac ccg ttc gtg      720
Cys Val Gly Gly Gly Ser Asn Ala Met Gly Ile Phe Tyr Pro Phe Val
225                 230                 235                 240 aac gac aaa aaa gtt aag ctg gtt ggc gtt gag gct ggt ggt aaa ggc      768
Asn Asp Lys Lys Val Lys Leu Val Gly Val Glu Ala Gly Gly Lys Gly
                245                 250                 255 ctg gaa tct ggt aag cat tcc gct agc ctg aac gca ggt cag gtt ggt      816
Leu Glu Ser Gly Lys His Ser Ala Ser Leu Asn Ala Gly Gln Val Gly
            260                 265                 270 gtg tcc cat ggc atg ctg tcc tac ttt ctg cag gac gaa gaa ggt cag      864
Val Ser His Gly Met Leu Ser Tyr Phe Leu Gln Asp Glu Glu Gly Gln
        275                 280                 285 atc aaa cca agc cac tcc atc gca cca ggt ctg gat tat cca ggt gtt      912
Ile Lys Pro Ser His Ser Ile Ala Pro Gly Leu Asp Tyr Pro Gly Val
290                 295                 300 ggt cca gaa cac gct tac ctg aaa aaa att cag cgt gct gaa tac gtg      960
Gly Pro Glu His Ala Tyr Leu Lys Lys Ile Gln Arg Ala Glu Tyr Val
305                 310                 315                 320 gct gta acc gat gaa gaa gca ctg aaa gcg ttc cat gaa ctg agc cgt     1008
Ala Val Thr Asp Glu Glu Ala Leu Lys Ala Phe His Glu Leu Ser Arg
                325                 330                 335 acc gaa ggt atc atc cca gct ctg gaa tct gcg cat gct gtg gct tac     1056
Thr Glu Gly Ile Ile Pro Ala Leu Glu Ser Ala His Ala Val Ala Tyr
            340                 345                 350 gct atg aaa ctg gct aag gaa atg tct cgt gat gag atc atc atc gta     1104
Ala Met Lys Leu Ala Lys Glu Met Ser Arg Asp Glu Ile Ile Ile Val
        355                 360                 365 aac ctg tct ggt cgt ggt gac aaa gac ctg gat att gtc ctg aaa gcg     1152
Asn Leu Ser Gly Arg Gly Asp Lys Asp Leu Asp Ile Val Leu Lys Ala
370                 375                 380 tct ggc aac gtg                                                     1164
Ser Gly Asn Val
385
```

<210> SEQ ID NO 16

```
<211> LENGTH: 388
<212> TYPE: PRT
<213> ORGANISM: Artificial Sequence
<220> FEATURE:
<223> OTHER INFORMATION: Synthetic Construct

<400> SEQUENCE: 16

Met Trp Phe Gly Glu Phe Gly Gly Gln Tyr Val Pro Glu Thr Leu Val
1               5                   10                  15

Gly Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
        35                  40                  45

Arg Pro Thr Pro Leu Tyr Tyr Ala Lys Arg Leu Thr Glu Lys Ile Gly
    50                  55                  60

Gly Ala Lys Val Tyr Leu Lys Arg Glu Asp Leu Val His Gly Gly Ala
65                  70                  75                  80

His Lys Thr Asn Asn Ala Ile Gly Gln Ala Leu Leu Ala Lys Leu Met
                85                  90                  95

Gly Lys Thr Arg Leu Ile Ala Gly Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Leu Asn Val Phe Arg Met
    130                 135                 140

Lys Leu Leu Gly Ala Asn Val Ile Pro Val Asn Ser Gly Ser Arg Thr
145                 150                 155                 160

Leu Lys Asp Ala Ile Asp Glu Ala Leu Arg Asp Trp Val Ala Thr Phe
                165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
        195                 200                 205

Ala Gln Ile Pro Glu Ala Glu Gly Gln Leu Pro Asp Val Ile Val Ala
    210                 215                 220

Cys Val Gly Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
            260                 265                 270

Val Ser His Gly Met Leu Ser Tyr Phe Leu Gln Asp Glu Glu Gly Gln
        275                 280                 285

Ile Lys Pro Ser His Ser Ile Ala Pro Gly Leu Asp Tyr Pro Gly Val
    290                 295                 300

Gly Pro Glu His Ala Tyr Leu Lys Lys Ile Gln Arg Ala Glu Tyr Val
305                 310                 315                 320

Ala Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
        355                 360                 365

Asn Leu Ser Gly Arg Gly Asp Lys Asp Leu Asp Ile Val Leu Lys Ala
    370                 375                 380
```

Ser Gly Asn Val
385

<210> SEQ ID NO 17
<211> LENGTH: 1164
<212> TYPE: DNA
<213> ORGANISM: Artificial Sequence
<220> FEATURE:
<223> OTHER INFORMATION: Pf2A6
<220> FEATURE:
<221> NAME/KEY: CDS
<222> LOCATION: (1)..(1164)

<400> SEQUENCE: 17

```
atg tgg ttc ggt gaa ttt ggt ggt cag tac gtg cca gaa acg ctg gtt        48
Met Trp Phe Gly Glu Phe Gly Gly Gln Tyr Val Pro Glu Thr Leu Val
1               5                   10                  15 gga ccc ctg aaa gag ctg gaa aaa gct tac aaa cgt ttc aaa gat gac        96
Gly Pro Leu Lys Glu Leu Glu Lys Ala Tyr Lys Arg Phe Lys Asp Asp
            20                  25                  30 gaa gaa ttc aat cgt cag ctg aat tac tac ctg aaa acc tgg gca ggt       144
Glu Glu Phe Asn Arg Gln Leu Asn Tyr Tyr Leu Lys Thr Trp Ala Gly
        35                  40                  45 cgt cca acc cca ctg tac tac gca aaa cgc ctg act gaa aaa atc ggt       192
Arg Pro Thr Pro Leu Tyr Tyr Ala Lys Arg Leu Thr Glu Lys Ile Gly
    50                  55                  60 ggt gct aaa gtc tac ctg aaa cgt gaa gac ctg gtt cac ggt ggt gca       240
Gly Ala Lys Val Tyr Leu Lys Arg Glu Asp Leu Val His Gly Gly Ala
65                  70                  75                  80 cac aag acc aac aac gcc atc ggt cag gca ctg ctg gca aag ctc atg       288
His Lys Thr Asn Asn Ala Ile Gly Gln Ala Leu Leu Ala Lys Leu Met
                85                  90                  95 ggt aaa act cgt ctg atc gct ggg acc ggt gct ggt cag cac ggc gta       336
Gly Lys Thr Arg Leu Ile Ala Gly Thr Gly Ala Gly Gln His Gly Val
            100                 105                 110 gcg act gca atg gct ggc gca ctg ctg ggc atg aaa gtg gac att tac       384
Ala Thr Ala Met Ala Gly Ala Leu Leu Gly Met Lys Val Asp Ile Tyr
        115                 120                 125 atg ggt gct gag gac gta gaa cgt cag aaa ttg aac gta ttc cgt atg       432
Met Gly Ala Glu Asp Val Glu Arg Gln Lys Leu Asn Val Phe Arg Met
    130                 135                 140 aag ctg ctg ggt gca aac gta att cca gtt aac tcc ggt tct cgc acc       480
Lys Leu Leu Gly Ala Asn Val Ile Pro Val Asn Ser Gly Ser Arg Thr
145                 150                 155                 160 ctg aaa gac gca atc gac gag gct ctg cgt gat tgg gtg gct act ttt       528
Leu Lys Asp Ala Ile Asp Glu Ala Leu Arg Asp Trp Val Ala Thr Phe
                165                 170                 175 gaa tac acc cac tac cta ttc ggt tcc gcg gtc ggt cca cat ccg tat       576
Glu Tyr Thr His Tyr Leu Phe Gly Ser Ala Val Gly Pro His Pro Tyr
            180                 185                 190 ccg acc atc gtt cgt gat ttt cag tct gtt atc ggt cgt gag gct aaa       624
Pro Thr Ile Val Arg Asp Phe Gln Ser Val Ile Gly Arg Glu Ala Lys
        195                 200                 205 gcg cag atc ccg gag gct gaa ggt cag ctg cca gat gta atc gtt gct       672
Ala Gln Ile Pro Glu Ala Glu Gly Gln Leu Pro Asp Val Ile Val Ala
    210                 215                 220 tgt gtt ggt ggt ggc tct aac gcg atg ggt atc ttt tac ccg ttc gtg       720
Cys Val Gly Gly Gly Ser Asn Ala Met Gly Ile Phe Tyr Pro Phe Val
225                 230                 235                 240 aac gac aaa aaa gtt aag ctg gtt ggc gtt gag gct ggt ggt aaa ggc       768
Asn Asp Lys Lys Val Lys Leu Val Gly Val Glu Ala Gly Gly Lys Gly
```

```
ctg gaa tct ggt aag cat tcc gct agc ctg aac gca ggt cag gtt ggt    816
Leu Glu Ser Gly Lys His Ser Ala Ser Leu Asn Ala Gly Gln Val Gly
            260                 265                 270 gtg tcc cat ggc atg ctg tcc tac ttt ctg cag gac gaa gaa ggt cag    864
Val Ser His Gly Met Leu Ser Tyr Phe Leu Gln Asp Glu Glu Gly Gln
        275                 280                 285 atc aaa cca agc cac tcc atc gca cca ggt ctg gat tat cca ggt gtt    912
Ile Lys Pro Ser His Ser Ile Ala Pro Gly Leu Asp Tyr Pro Gly Val
    290                 295                 300 ggt cca gaa cac gct tac ctg aaa aaa att cag cgt gct gaa tac gtg    960
Gly Pro Glu His Ala Tyr Leu Lys Lys Ile Gln Arg Ala Glu Tyr Val
305                 310                 315                 320 gct gta acc gat gaa gaa gca ctg aaa gcg ttc cat gaa ctg agc cgt    1008
Ala Val Thr Asp Glu Glu Ala Leu Lys Ala Phe His Glu Leu Ser Arg
                325                 330                 335 acc gaa ggt atc atc cca gct ctg gaa tct gcg cat gct gtg gct tac    1056
Thr Glu Gly Ile Ile Pro Ala Leu Glu Ser Ala His Ala Val Ala Tyr
            340                 345                 350 gct atg aaa ctg gct aag gaa atg tct cgt gat gag atc atc atc gta    1104
Ala Met Lys Leu Ala Lys Glu Met Ser Arg Asp Glu Ile Ile Ile Val
        355                 360                 365 aac ctg tct ggt cgt ggt gac aaa gac ctg gat att gtc ctg aaa gcg    1152
Asn Leu Ser Gly Arg Gly Asp Lys Asp Leu Asp Ile Val Leu Lys Ala
    370                 375                 380 tct ggc aac gtg                                                    1164
Ser Gly Asn Val
385
```

<210> SEQ ID NO 18
<211> LENGTH: 388
<212> TYPE: PRT
<213> ORGANISM: Artificial Sequence
<220> FEATURE:
<223> OTHER INFORMATION: Synthetic Construct

<400> SEQUENCE: 18

```
Met Trp Phe Gly Glu Phe Gly Gly Gln Tyr Val Pro Glu Thr Leu Val
1               5                   10                  15

Gly Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
        35                  40                  45

Arg Pro Thr Pro Leu Tyr Tyr Ala Lys Arg Leu Thr Glu Lys Ile Gly
    50                  55                  60

Gly Ala Lys Val Tyr Leu Lys Arg Glu Asp Leu Val His Gly Ala
65                  70                  75                  80

His Lys Thr Asn Asn Ala Ile Gly Gln Ala Leu Leu Ala Lys Leu Met
                85                  90                  95

Gly Lys Thr Arg Leu Ile Ala Gly Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Leu Asn Val Phe Arg Met
    130                 135                 140

Lys Leu Leu Gly Ala Asn Val Ile Pro Val Asn Ser Gly Ser Arg Thr
145                 150                 155                 160

Leu Lys Asp Ala Ile Asp Glu Ala Leu Arg Asp Trp Val Ala Thr Phe
```

```
                    165                 170                 175
Glu Tyr Thr His Tyr Leu Phe Gly Ser Ala Val Gly Pro His Pro Tyr
                180                 185                 190

Pro Thr Ile Val Arg Asp Phe Gln Ser Val Ile Gly Arg Glu Ala Lys
            195                 200                 205

Ala Gln Ile Pro Glu Ala Glu Gly Gln Leu Pro Asp Val Ile Val Ala
        210                 215                 220

Cys Val Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
            260                 265                 270

Val Ser His Gly Met Leu Ser Tyr Phe Leu Gln Asp Glu Glu Gly Gln
        275                 280                 285

Ile Lys Pro Ser His Ser Ile Ala Pro Gly Leu Asp Tyr Pro Gly Val
    290                 295                 300

Gly Pro Glu His Ala Tyr Leu Lys Lys Ile Gln Arg Ala Glu Tyr Val
305                 310                 315                 320

Ala Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
        355                 360                 365

Asn Leu Ser Gly Arg Gly Asp Lys Asp Leu Asp Ile Val Leu Lys Ala
    370                 375                 380

Ser Gly Asn Val
385

<210> SEQ ID NO 19
<211> LENGTH: 1164
<212> TYPE: DNA
<213> ORGANISM: Artificial Sequence
<220> FEATURE:
<223> OTHER INFORMATION: Pf0A9
<220> FEATURE:
<221> NAME/KEY: CDS
<222> LOCATION: (1)..(1164)

<400> SEQUENCE: 19 atg tgg ttc ggt gaa ttt ggt ggt cag tac gtg cca gaa acg ctg gtt        48
Met Trp Phe Gly Glu Phe Gly Gly Gln Tyr Val Pro Glu Thr Leu Val
1               5                   10                  15 gga ccc ctg aaa gag ctg gaa aaa gct tac aaa cgt ttc aaa gat gac        96
Gly Pro Leu Lys Glu Leu Glu Lys Ala Tyr Lys Arg Phe Lys Asp Asp
            20                  25                  30 gaa gaa ttc aat cgt cag ctg aat tac tac ctg aaa acc tgg gca ggt       144
Glu Glu Phe Asn Arg Gln Leu Asn Tyr Tyr Leu Lys Thr Trp Ala Gly
        35                  40                  45 cgt cca acc cca ctg tac tac gca aaa cgc ctg act gaa aaa atc ggt       192
Arg Pro Thr Pro Leu Tyr Tyr Ala Lys Arg Leu Thr Glu Lys Ile Gly
    50                  55                  60 ggt gct aaa gtc tac ctg aaa cgt gaa gac ctg gtt cac ggt ggt gca       240
Gly Ala Lys Val Tyr Leu Lys Arg Glu Asp Leu Val His Gly Gly Ala
65                  70                  75                  80 cac aag acc aac aac gcc atc ggt cag gca ctg ctg gca aag ctc atg       288
His Lys Thr Asn Asn Ala Ile Gly Gln Ala Leu Leu Ala Lys Leu Met
```

-continued

|  |  |  |  | 85 |  |  |  | 90 |  |  |  | 95 |  |  |  |  |
|---|---|---|---|---|---|---|---|---|---|---|---|---|---|---|---|---|
| ggt | aaa | act | cgt | ctg | atc | gct | gag | acc | ggt | gct | ggt | cag | cac | ggc | gta | 336 |
| Gly | Lys | Thr | Arg | Leu | Ile | Ala | Glu | Thr | Gly | Ala | Gly | Gln | His | Gly | Val |  |
|  |  |  | 100 |  |  |  |  | 105 |  |  |  |  | 110 |  |  |  |

```
gcg act gca atg gct ggt gca ctg ctg ggc atg aaa gtg gac att tac    384
Ala Thr Ala Met Ala Gly Ala Leu Leu Gly Met Lys Val Asp Ile Tyr
            115                 120                 125 atg ggt gct gag gac gta gaa cgt cag aaa ctg aac gta ttc cgt atg    432
Met Gly Ala Glu Asp Val Glu Arg Gln Lys Leu Asn Val Phe Arg Met
130                 135                 140 aag ctg ctg ggt gca aac gta att cca gtt aac tcc ggt tct cgc acc    480
Lys Leu Leu Gly Ala Asn Val Ile Pro Val Asn Ser Gly Ser Arg Thr
145                 150                 155                 160 ctg aaa gac gca ttt gac gag gct ctg cgt gat tgg gtg gct act ttt    528
Leu Lys Asp Ala Phe Asp Glu Ala Leu Arg Asp Trp Val Ala Thr Phe
                165                 170                 175 gaa tac acc cac tac cta atc ggt tcc gtg gtc ggt cca cat ccg tat    576
Glu Tyr Thr His Tyr Leu Ile Gly Ser Val Val Gly Pro His Pro Tyr
            180                 185                 190 ccg acc atc gtt cgt gat ttt cag tct gtt atc ggt cgt gag gct aaa    624
Pro Thr Ile Val Arg Asp Phe Gln Ser Val Ile Gly Arg Glu Ala Lys
        195                 200                 205 gcg cag atc ctg gag gct gaa ggt cag ctg cca gat gta atc gtt gct    672
Ala Gln Ile Leu Glu Ala Glu Gly Gln Leu Pro Asp Val Ile Val Ala
    210                 215                 220 tgt gtt ggt ggt ggc tct aac gcg atg ggt atc ttt tac ccg ttc gtg    720
Cys Val Gly Gly Gly Ser Asn Ala Met Gly Ile Phe Tyr Pro Phe Val
225                 230                 235                 240 aac gac aaa aaa gtt aag ctg gtt ggc gtt gag gct ggt ggt aaa ggc    768
Asn Asp Lys Lys Val Lys Leu Val Gly Val Glu Ala Gly Gly Lys Gly
                245                 250                 255 ctg gaa tct ggt aag cat tcc gct agc ctg aac gca ggt cag gtt ggt    816
Leu Glu Ser Gly Lys His Ser Ala Ser Leu Asn Ala Gly Gln Val Gly
            260                 265                 270 gtg tcc cat ggc atg ctg tcc tac ttt ctg cag gac gaa gaa ggt cag    864
Val Ser His Gly Met Leu Ser Tyr Phe Leu Gln Asp Glu Glu Gly Gln
        275                 280                 285 atc aaa cca agc cac tcc atc gca cca ggt ctg gat cat cca ggt gtt    912
Ile Lys Pro Ser His Ser Ile Ala Pro Gly Leu Asp His Pro Gly Val
    290                 295                 300 ggt cca gaa cac gct tac ctg aaa aaa att cag cgt gct gaa tac gtg    960
Gly Pro Glu His Ala Tyr Leu Lys Lys Ile Gln Arg Ala Glu Tyr Val
305                 310                 315                 320 gct gta acc gat gaa gaa gca ctg aaa gcg ttc cat gaa ctg agc cgt   1008
Ala Val Thr Asp Glu Glu Ala Leu Lys Ala Phe His Glu Leu Ser Arg
                325                 330                 335 acc gaa ggt atc atc cca gct ctg gaa tct gcg cat gct gtg gct tac   1056
Thr Glu Gly Ile Ile Pro Ala Leu Glu Ser Ala His Ala Val Ala Tyr
            340                 345                 350 gct atg aaa ctg gct aag gaa atg tct cgt gat gag atc atc atc gta   1104
Ala Met Lys Leu Ala Lys Glu Met Ser Arg Asp Glu Ile Ile Ile Val
        355                 360                 365 aac ctg tct ggt cgt ggt gac aaa gac ctg gat att gtc ctg aaa gcg   1152
Asn Leu Ser Gly Arg Gly Asp Lys Asp Leu Asp Ile Val Leu Lys Ala
    370                 375                 380 tct ggc aac gtg                                                    1164
Ser Gly Asn Val
385
```

```
<210> SEQ ID NO 20
<211> LENGTH: 388
<212> TYPE: PRT
<213> ORGANISM: Artificial Sequence
<220> FEATURE:
<223> OTHER INFORMATION: Synthetic Construct

<400> SEQUENCE: 20
```

Met Trp Phe Gly Glu Phe Gly Gly Gln Tyr Val Pro Glu Thr Leu Val
1               5                   10                  15

Gly Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
        35                  40                  45

Arg Pro Thr Pro Leu Tyr Tyr Ala Lys Arg Leu Thr Glu Lys Ile Gly
    50                  55                  60

Gly Ala Lys Val Tyr Leu Lys Arg Glu Asp Leu Val His Gly Gly Ala
65                  70                  75                  80

His Lys Thr Asn Asn Ala Ile Gly Gln Ala Leu Leu Ala Lys Leu Met
                85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Leu Asn Val Phe Arg Met
    130                 135                 140

Lys Leu Leu Gly Ala Asn Val Ile Pro Val Asn Ser Gly Ser Arg Thr
145                 150                 155                 160

Leu Lys Asp Ala Phe Asp Glu Ala Leu Arg Asp Trp Val Ala Thr Phe
                165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
        195                 200                 205

Ala Gln Ile Leu Glu Ala Glu Gly Gln Leu Pro Asp Val Ile Val Ala
    210                 215                 220

Cys Val Gly Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
            260                 265                 270

Val Ser His Gly Met Leu Ser Tyr Phe Leu Gln Asp Glu Glu Gly Gln
        275                 280                 285

Ile Lys Pro Ser His Ser Ile Ala Pro Gly Leu Asp His Pro Gly Val
    290                 295                 300

Gly Pro Glu His Ala Tyr Leu Lys Lys Ile Gln Arg Ala Glu Tyr Val
305                 310                 315                 320

Ala Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
        355                 360                 365

Asn Leu Ser Gly Arg Gly Asp Lys Asp Leu Asp Ile Val Leu Lys Ala

```
                    370                 375                 380
Ser Gly Asn Val
385

<210> SEQ ID NO 21
<211> LENGTH: 1164
<212> TYPE: DNA
<213> ORGANISM: Artificial Sequence
<220> FEATURE:
<223> OTHER INFORMATION: Pf0A9 E104G
<220> FEATURE:
<221> NAME/KEY: CDS
<222> LOCATION: (1)..(1164)

<400> SEQUENCE: 21 atg tgg ttc ggt gaa ttt ggt ggt cag tac gtg cca gaa acg ctg gtt      48
Met Trp Phe Gly Glu Phe Gly Gly Gln Tyr Val Pro Glu Thr Leu Val
1               5                   10                  15 gga ccc ctg aaa gag ctg gaa aaa gct tac aaa cgt ttc aaa gat gac      96
Gly Pro Leu Lys Glu Leu Glu Lys Ala Tyr Lys Arg Phe Lys Asp Asp
            20                  25                  30 gaa gaa ttc aat cgt cag ctg aat tac tac ctg aaa acc tgg gca ggt     144
Glu Glu Phe Asn Arg Gln Leu Asn Tyr Tyr Leu Lys Thr Trp Ala Gly
        35                  40                  45 cgt cca acc cca ctg tac tac gca aaa cgc ctg act gaa aaa atc ggt     192
Arg Pro Thr Pro Leu Tyr Tyr Ala Lys Arg Leu Thr Glu Lys Ile Gly
    50                  55                  60 ggt gct aaa gtc tac ctg aaa cgt gaa gac ctg gtt cac ggt ggt gca     240
Gly Ala Lys Val Tyr Leu Lys Arg Glu Asp Leu Val His Gly Gly Ala
65                  70                  75                  80 cac aag acc aac aac gcc atc ggt cag gca ctg ctg gca aag ctc atg     288
His Lys Thr Asn Asn Ala Ile Gly Gln Ala Leu Leu Ala Lys Leu Met
                85                  90                  95 ggt aaa act cgt ctg atc gct ggg acc ggt gct ggt cag cac ggc gta     336
Gly Lys Thr Arg Leu Ile Ala Gly Thr Gly Ala Gly Gln His Gly Val
            100                 105                 110 gcg act gca atg gct ggt gca ctg ctg ggc atg aaa gtg gac att tac     384
Ala Thr Ala Met Ala Gly Ala Leu Leu Gly Met Lys Val Asp Ile Tyr
        115                 120                 125 atg ggt gct gag gac gta gaa cgt cag aaa ctg aac gta ttc cgt atg     432
Met Gly Ala Glu Asp Val Glu Arg Gln Lys Leu Asn Val Phe Arg Met
    130                 135                 140 aag ctg ctg ggt gca aac gta att cca gtt aac tcc ggt tct cgc acc     480
Lys Leu Leu Gly Ala Asn Val Ile Pro Val Asn Ser Gly Ser Arg Thr
145                 150                 155                 160 ctg aaa gac gca ttt gac gag gct ctg cgt gat tgg gtg gct act ttt     528
Leu Lys Asp Ala Phe Asp Glu Ala Leu Arg Asp Trp Val Ala Thr Phe
                165                 170                 175 gaa tac acc cac tac cta atc ggt tcc gtg gtc ggt cca cat ccg tat     576
Glu Tyr Thr His Tyr Leu Ile Gly Ser Val Val Gly Pro His Pro Tyr
            180                 185                 190 ccg acc atc gtt cgt gat ttt cag tct gtt atc ggt cgt gag gct aaa     624
Pro Thr Ile Val Arg Asp Phe Gln Ser Val Ile Gly Arg Glu Ala Lys
        195                 200                 205 gcg cag atc ctg gag gct gaa ggt cag ctg cca gat gta atc gtt gct     672
Ala Gln Ile Leu Glu Ala Glu Gly Gln Leu Pro Asp Val Ile Val Ala
    210                 215                 220 tgt gtt ggt ggt ggc tct aac gcg atg ggt atc ttt tac ccg ttc gtg     720
Cys Val Gly Gly Gly Ser Asn Ala Met Gly Ile Phe Tyr Pro Phe Val
225                 230                 235                 240 aac gac aaa aaa gtt aag ctg gtt ggc gtt gag gct ggt ggt aaa ggc     768
```

```
                    Asn Asp Lys Lys Val Lys Leu Val Gly Val Glu Ala Gly Gly Lys Gly
                                    245                 250                 255 ctg gaa tct ggt aag cat tcc gct agc ctg aac gca ggt cag gtt ggt           816
Leu Glu Ser Gly Lys His Ser Ala Ser Leu Asn Ala Gly Gln Val Gly
            260                 265                 270 gtg tcc cat ggc atg ctg tcc tac ttt ctg cag gac gaa gaa ggt cag           864
Val Ser His Gly Met Leu Ser Tyr Phe Leu Gln Asp Glu Glu Gly Gln
275                 280                 285 atc aaa cca agc cac tcc atc gca cca ggt ctg gat cat cca ggt gtt           912
Ile Lys Pro Ser His Ser Ile Ala Pro Gly Leu Asp His Pro Gly Val
        290                 295                 300 ggt cca gaa cac gct tac ctg aaa aaa att cag cgt gct gaa tac gtg           960
Gly Pro Glu His Ala Tyr Leu Lys Lys Ile Gln Arg Ala Glu Tyr Val
305                 310                 315                 320 gct gta acc gat gaa gaa gca ctg aaa gcg ttc cat gaa ctg agc cgt          1008
Ala Val Thr Asp Glu Glu Ala Leu Lys Ala Phe His Glu Leu Ser Arg
                325                 330                 335 acc gaa ggt atc atc cca gct ctg gaa tct gcg cat gct gtg gct tac          1056
Thr Glu Gly Ile Ile Pro Ala Leu Glu Ser Ala His Ala Val Ala Tyr
            340                 345                 350 gct atg aaa ctg gct aag gaa atg tct cgt gat gag atc atc atc gta          1104
Ala Met Lys Leu Ala Lys Glu Met Ser Arg Asp Glu Ile Ile Ile Val
355                 360                 365 aac ctg tct ggt cgt ggt gac aaa gac ctg gat att gtc ctg aaa gcg          1152
Asn Leu Ser Gly Arg Gly Asp Lys Asp Leu Asp Ile Val Leu Lys Ala
        370                 375                 380 tct ggc aac gtg                                                          1164
Ser Gly Asn Val
385

<210> SEQ ID NO 22
<211> LENGTH: 388
<212> TYPE: PRT
<213> ORGANISM: Artificial Sequence
<220> FEATURE:
<223> OTHER INFORMATION: Synthetic Construct

<400> SEQUENCE: 22

Met Trp Phe Gly Glu Phe Gly Gly Gln Tyr Val Pro Glu Thr Leu Val
1               5                   10                  15

Gly Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
        35                  40                  45

Arg Pro Thr Pro Leu Tyr Tyr Ala Lys Arg Leu Thr Glu Lys Ile Gly
    50                  55                  60

Gly Ala Lys Val Tyr Leu Lys Arg Glu Asp Leu Val His Gly Gly Ala
65                  70                  75                  80

His Lys Thr Asn Asn Ala Ile Gly Gln Ala Leu Leu Ala Lys Leu Met
                85                  90                  95

Gly Lys Thr Arg Leu Ile Ala Gly Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Leu Asn Val Phe Arg Met
    130                 135                 140

Lys Leu Leu Gly Ala Asn Val Ile Pro Val Asn Ser Gly Ser Arg Thr
145                 150                 155                 160
```

```
Leu Lys Asp Ala Phe Asp Glu Ala Leu Arg Asp Trp Val Ala Thr Phe
            165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
            195                 200                 205

Ala Gln Ile Leu Glu Ala Glu Gly Gln Leu Pro Asp Val Ile Val Ala
            210                 215                 220

Cys Val Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
            245                 250                 255

Leu Glu Ser Gly Lys His Ser Ala Ser Leu Asn Ala Gly Gln Val Gly
            260                 265                 270

Val Ser His Gly Met Leu Ser Tyr Phe Leu Gln Asp Glu Gly Gln
            275                 280                 285

Ile Lys Pro Ser His Ser Ile Ala Pro Gly Leu Asp His Pro Gly Val
            290                 295                 300

Gly Pro Glu His Ala Tyr Leu Lys Lys Ile Gln Arg Ala Glu Tyr Val
305                 310                 315                 320

Ala Val Thr Asp Glu Glu Ala Leu Lys Ala Phe His Glu Leu Ser Arg
            325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
            355                 360                 365

Asn Leu Ser Gly Arg Gly Asp Lys Asp Leu Asp Ile Val Leu Lys Ala
            370                 375                 380

Ser Gly Asn Val
385
```

<210> SEQ ID NO 23
<211> LENGTH: 1167
<212> TYPE: DNA
<213> ORGANISM: Artificial Sequence
<220> FEATURE:
<223> OTHER INFORMATION: Tm2F3
<220> FEATURE:
<221> NAME/KEY: CDS
<222> LOCATION: (1)..(1167)

<400> SEQUENCE: 23

```
atg aaa ggc tac ttc ggt ccg tac ggt ggc cag tac gtg ccg gaa atc      48
Met Lys Gly Tyr Phe Gly Pro Tyr Gly Gly Gln Tyr Val Pro Glu Ile
1               5                   10                  15 ctg atg gga gct ctg gaa gaa ctg gaa gct gcg tac gaa gaa atc atg      96
Leu Met Gly Ala Leu Glu Glu Leu Glu Ala Ala Tyr Glu Glu Ile Met
                20                  25                  30 aaa gat gag tct ttc tgg aaa gaa ttc aat gac ctg ctg cgc gat tat    144
Lys Asp Glu Ser Phe Trp Lys Glu Phe Asn Asp Leu Leu Arg Asp Tyr
            35                  40                  45 gcg ggt cgt ccg act ccg ctg tac ttc gca cgt cgt ctg tcc gaa aaa    192
Ala Gly Arg Pro Thr Pro Leu Tyr Phe Ala Arg Arg Leu Ser Glu Lys
        50                  55                  60 tac ggt gct cgc gta tat ctg aaa cgt gaa gac ctg ctg cat act ggt    240
Tyr Gly Ala Arg Val Tyr Leu Lys Arg Glu Asp Leu Leu His Thr Gly
65                  70                  75                  80 gcg cat aaa atc aat aac gct atc ggc cag gtt ctg ctg gca aaa cta    288
```

|  |  |  |  |  |  |  |  |  |  |  |  |  |  |  |
|---|---|---|---|---|---|---|---|---|---|---|---|---|---|---|
| Ala | His | Lys | Ile | Asn | Asn | Ala | Ile | Gly | Gln | Val | Leu | Leu | Ala | Lys | Leu |
|  |  |  |  | 85 |  |  |  | 90 |  |  |  | 95 |  |  |  |

| atg | ggc | aaa | acc | cgt | atc | att | gct | gaa | acg | ggt | gct | ggt | cag | cac | ggc | 336 |
|---|---|---|---|---|---|---|---|---|---|---|---|---|---|---|---|---|
| Met | Gly | Lys | Thr | Arg | Ile | Ile | Ala | Glu | Thr | Gly | Ala | Gly | Gln | His | Gly |  |
|  |  |  | 100 |  |  |  |  | 105 |  |  |  |  | 110 |  |  |  |

| gta | gca | act | gct | acc | gca | gca | gcg | ctg | ttc | ggt | atg | gaa | tgt | gta | atc | 384 |
|---|---|---|---|---|---|---|---|---|---|---|---|---|---|---|---|---|
| Val | Ala | Thr | Ala | Thr | Ala | Ala | Ala | Leu | Phe | Gly | Met | Glu | Cys | Val | Ile |  |
|  |  | 115 |  |  |  |  | 120 |  |  |  |  | 125 |  |  |  |  |

| tat | atg | ggc | gaa | gaa | gac | acg | atc | cgc | cag | aaa | cta | aac | gtt | gaa | cgt | 432 |
|---|---|---|---|---|---|---|---|---|---|---|---|---|---|---|---|---|
| Tyr | Met | Gly | Glu | Glu | Asp | Thr | Ile | Arg | Gln | Lys | Leu | Asn | Val | Glu | Arg |  |
|  | 130 |  |  |  |  | 135 |  |  |  |  | 140 |  |  |  |  |  |

| atg | aaa | ctg | ctg | ggt | gct | aaa | gtt | gta | ccg | gta | aaa | tcc | ggt | agc | cgt | 480 |
|---|---|---|---|---|---|---|---|---|---|---|---|---|---|---|---|---|
| Met | Lys | Leu | Leu | Gly | Ala | Lys | Val | Val | Pro | Val | Lys | Ser | Gly | Ser | Arg |  |
| 145 |  |  |  |  | 150 |  |  |  |  | 155 |  |  |  |  | 160 |  |

| acc | ctg | aaa | gac | gca | att | gac | gaa | gct | ctg | cgt | gac | tgg | att | acc | aac | 528 |
|---|---|---|---|---|---|---|---|---|---|---|---|---|---|---|---|---|
| Thr | Leu | Lys | Asp | Ala | Ile | Asp | Glu | Ala | Leu | Arg | Asp | Trp | Ile | Thr | Asn |  |
|  |  |  |  | 165 |  |  |  |  | 170 |  |  |  |  | 175 |  |  |

| ctg | cag | acc | acc | tat | tac | gtg | atc | ggc | tct | gtg | gtt | ggt | ccg | cat | cca | 576 |
|---|---|---|---|---|---|---|---|---|---|---|---|---|---|---|---|---|
| Leu | Gln | Thr | Thr | Tyr | Tyr | Val | Ile | Gly | Ser | Val | Val | Gly | Pro | His | Pro |  |
|  |  |  | 180 |  |  |  |  | 185 |  |  |  |  | 190 |  |  |  |

| tat | ccg | att | atc | gta | cgt | aac | ttc | caa | aag | gtt | atc | ggc | gaa | gag | acc | 624 |
|---|---|---|---|---|---|---|---|---|---|---|---|---|---|---|---|---|
| Tyr | Pro | Ile | Ile | Val | Arg | Asn | Phe | Gln | Lys | Val | Ile | Gly | Glu | Glu | Thr |  |
|  |  |  | 195 |  |  |  |  | 200 |  |  |  |  | 205 |  |  |  |

| aaa | aaa | cag | att | cca | gaa | aaa | gaa | ggc | cgt | ctg | ccg | gac | tac | atc | gtt | 672 |
|---|---|---|---|---|---|---|---|---|---|---|---|---|---|---|---|---|
| Lys | Lys | Gln | Ile | Pro | Glu | Lys | Glu | Gly | Arg | Leu | Pro | Asp | Tyr | Ile | Val |  |
| 210 |  |  |  |  | 215 |  |  |  |  | 220 |  |  |  |  |  |  |

| gcg | tgc | gtg | ggt | ggt | ggt | tct | aac | gct | gcc | ggt | atc | ttc | tat | ccg | ttt | 720 |
|---|---|---|---|---|---|---|---|---|---|---|---|---|---|---|---|---|
| Ala | Cys | Val | Gly | Gly | Gly | Ser | Asn | Ala | Ala | Gly | Ile | Phe | Tyr | Pro | Phe |  |
| 225 |  |  |  |  | 230 |  |  |  |  | 235 |  |  |  |  | 240 |  |

| atc | gat | tct | ggt | gtg | aag | ctg | atc | ggc | gta | gaa | gcc | ggt | ggc | gaa | ggt | 768 |
|---|---|---|---|---|---|---|---|---|---|---|---|---|---|---|---|---|
| Ile | Asp | Ser | Gly | Val | Lys | Leu | Ile | Gly | Val | Glu | Ala | Gly | Gly | Glu | Gly |  |
|  |  |  | 245 |  |  |  |  | 250 |  |  |  |  | 255 |  |  |  |

| ctg | gaa | acc | ggt | aaa | cat | gcg | gct | tct | ctg | ctg | aaa | ggt | aaa | atc | ggc | 816 |
|---|---|---|---|---|---|---|---|---|---|---|---|---|---|---|---|---|
| Leu | Glu | Thr | Gly | Lys | His | Ala | Ala | Ser | Leu | Leu | Lys | Gly | Lys | Ile | Gly |  |
|  |  | 260 |  |  |  |  | 265 |  |  |  |  | 270 |  |  |  |  |

| tac | ctg | cac | ggt | tct | aag | acg | ttc | gtt | ctg | cag | gat | gac | tgg | ggt | caa | 864 |
|---|---|---|---|---|---|---|---|---|---|---|---|---|---|---|---|---|
| Tyr | Leu | His | Gly | Ser | Lys | Thr | Phe | Val | Leu | Gln | Asp | Asp | Trp | Gly | Gln |  |
|  | 275 |  |  |  |  | 280 |  |  |  |  | 285 |  |  |  |  |  |

| gtt | cag | gtg | agc | cac | tcc | gtc | tcc | gct | ggc | ctg | gac | tac | tcc | ggt | gtc | 912 |
|---|---|---|---|---|---|---|---|---|---|---|---|---|---|---|---|---|
| Val | Gln | Val | Ser | His | Ser | Val | Ser | Ala | Gly | Leu | Asp | Tyr | Ser | Gly | Val |  |
|  | 290 |  |  |  |  | 295 |  |  |  |  | 300 |  |  |  |  |  |

| ggt | ccg | gaa | cac | gcc | tat | tgg | cgt | gag | acc | ggt | aaa | gtg | ctg | tac | gat | 960 |
|---|---|---|---|---|---|---|---|---|---|---|---|---|---|---|---|---|
| Gly | Pro | Glu | His | Ala | Tyr | Trp | Arg | Glu | Thr | Gly | Lys | Val | Leu | Tyr | Asp |  |
| 305 |  |  |  |  | 310 |  |  |  |  | 315 |  |  |  |  | 320 |  |

| gct | gtg | acc | gat | gaa | gaa | gct | ctg | gac | gca | ttc | atc | gaa | ctg | tct | cgc | 1008 |
|---|---|---|---|---|---|---|---|---|---|---|---|---|---|---|---|---|
| Ala | Val | Thr | Asp | Glu | Glu | Ala | Leu | Asp | Ala | Phe | Ile | Glu | Leu | Ser | Arg |  |
|  |  |  | 325 |  |  |  |  | 330 |  |  |  |  | 335 |  |  |  |

| ctg | gaa | ggc | atc | atc | cca | gcc | ctg | gag | tct | tct | cac | gca | ctg | gct | tat | 1056 |
|---|---|---|---|---|---|---|---|---|---|---|---|---|---|---|---|---|
| Leu | Glu | Gly | Ile | Ile | Pro | Ala | Leu | Glu | Ser | Ser | His | Ala | Leu | Ala | Tyr |  |
|  |  |  | 340 |  |  |  |  | 345 |  |  |  |  | 350 |  |  |  |

| ctg | aag | aag | atc | aac | atc | aag | ggt | aaa | gtt | gtg | gtt | aat | ctg | tct | | 1104 |
|---|---|---|---|---|---|---|---|---|---|---|---|---|---|---|---|---|
| Leu | Lys | Lys | Ile | Asn | Ile | Lys | Gly | Lys | Val | Val | Val | Asn | Leu | Ser |  |  |
|  | 355 |  |  |  |  | 360 |  |  |  |  | 365 |  |  |  |  |  |

| ggt | cgt | ggt | gac | aag | gat | ctg | gaa | tct | gta | ctg | aac | cac | ccg | tat | gtt | 1152 |
|---|---|---|---|---|---|---|---|---|---|---|---|---|---|---|---|---|
| Gly | Arg | Gly | Asp | Lys | Asp | Leu | Glu | Ser | Val | Leu | Asn | His | Pro | Tyr | Val |  |
|  | 370 |  |  |  |  | 375 |  |  |  |  | 380 |  |  |  |  |  |

| cgc | gaa | cgc | atc | cgc | | | | | | | | | | | | 1167 |
|---|---|---|---|---|---|---|---|---|---|---|---|---|---|---|---|---|
| Arg | Glu | Arg | Ile | Arg |  |  |  |  |  |  |  |  |  |  |  |  |
| 385 |  |  |  |  |  |  |  |  |  |  |  |  |  |  |  |  |

<210> SEQ ID NO 24
<211> LENGTH: 389
<212> TYPE: PRT
<213> ORGANISM: Artificial Sequence
<220> FEATURE:
<223> OTHER INFORMATION: Synthetic Construct

<400> SEQUENCE: 24

```
Met Lys Gly Tyr Phe Gly Pro Tyr Gly Gly Gln Tyr Val Pro Glu Ile
1               5                   10                  15

Leu Met Gly Ala Leu Glu Glu Leu Glu Ala Ala Tyr Glu Glu Ile Met
            20                  25                  30

Lys Asp Glu Ser Phe Trp Lys Glu Phe Asn Asp Leu Leu Arg Asp Tyr
        35                  40                  45

Ala Gly Arg Pro Thr Pro Leu Tyr Phe Ala Arg Arg Leu Ser Glu Lys
    50                  55                  60

Tyr Gly Ala Arg Val Tyr Leu Lys Arg Glu Asp Leu Leu His Thr Gly
65                  70                  75                  80

Ala His Lys Ile Asn Asn Ala Ile Gly Gln Val Leu Leu Ala Lys Leu
                85                  90                  95

Met Gly Lys Thr Arg Ile Ile Ala Glu Thr Gly Ala Gly Gln His Gly
            100                 105                 110

Val Ala Thr Ala Thr Ala Ala Ala Leu Phe Gly Met Glu Cys Val Ile
        115                 120                 125

Tyr Met Gly Glu Glu Asp Thr Ile Arg Gln Lys Leu Asn Val Glu Arg
    130                 135                 140

Met Lys Leu Leu Gly Ala Lys Val Val Pro Val Lys Ser Gly Ser Arg
145                 150                 155                 160

Thr Leu Lys Asp Ala Ile Asp Glu Ala Leu Arg Asp Trp Ile Thr Asn
                165                 170                 175

Leu Gln Thr Thr Tyr Tyr Val Ile Gly Ser Val Val Gly Pro His Pro
            180                 185                 190

Tyr Pro Ile Ile Val Arg Asn Phe Gln Lys Val Ile Gly Glu Glu Thr
        195                 200                 205

Lys Lys Gln Ile Pro Glu Lys Glu Gly Arg Leu Pro Asp Tyr Ile Val
    210                 215                 220

Ala Cys Val Gly Gly Gly Ser Asn Ala Ala Gly Ile Phe Tyr Pro Phe
225                 230                 235                 240

Ile Asp Ser Gly Val Lys Leu Ile Gly Val Glu Ala Gly Gly Glu Gly
                245                 250                 255

Leu Glu Thr Gly Lys His Ala Ala Ser Leu Leu Lys Gly Lys Ile Gly
            260                 265                 270

Tyr Leu His Gly Ser Lys Thr Phe Val Leu Gln Asp Asp Trp Gly Gln
        275                 280                 285

Val Gln Val Ser His Ser Val Ser Ala Gly Leu Asp Tyr Ser Gly Val
    290                 295                 300

Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg
                325                 330                 335

Leu Glu Gly Ile Ile Pro Ala Leu Glu Ser Ser His Ala Leu Ala Tyr
            340                 345                 350

Leu Lys Lys Ile Asn Ile Lys Gly Lys Val Val Val Asn Leu Ser
        355                 360                 365
```

```
Gly Arg Gly Asp Lys Asp Leu Glu Ser Val Leu Asn His Pro Tyr Val
370                 375                 380

Arg Glu Arg Ile Arg
385

<210> SEQ ID NO 25
<211> LENGTH: 1167
<212> TYPE: DNA
<213> ORGANISM: Artificial Sequence
<220> FEATURE:
<223> OTHER INFORMATION: Tm2F3 I184F
<220> FEATURE:
<221> NAME/KEY: CDS
<222> LOCATION: (1)..(1167)

<400> SEQUENCE: 25 atg aaa ggc tac ttc ggt ccg tac ggt ggc cag tac gtg ccg gaa atc      48
Met Lys Gly Tyr Phe Gly Pro Tyr Gly Gly Gln Tyr Val Pro Glu Ile
1               5                   10                  15 ctg atg gga gct ctg gaa gaa ctg gaa gct gcg tac gaa gaa atc atg     96
Leu Met Gly Ala Leu Glu Glu Leu Glu Ala Ala Tyr Glu Glu Ile Met
            20                  25                  30 aaa gat gag tct ttc tgg aaa gaa ttc aat gac ctg ctg cgc gat tat    144
Lys Asp Glu Ser Phe Trp Lys Glu Phe Asn Asp Leu Leu Arg Asp Tyr
        35                  40                  45 gcg ggt cgt ccg act ccg ctg tac ttc gca cgt cgt ctg tcc gaa aaa    192
Ala Gly Arg Pro Thr Pro Leu Tyr Phe Ala Arg Arg Leu Ser Glu Lys
    50                  55                  60 tac ggt gct cgc gta tat ctg aaa cgt gaa gac ctg ctg cat act ggt    240
Tyr Gly Ala Arg Val Tyr Leu Lys Arg Glu Asp Leu Leu His Thr Gly
65                  70                  75                  80 gcg cat aaa atc aat aac gct atc ggc cag gtt ctg ctg gca aaa cta    288
Ala His Lys Ile Asn Asn Ala Ile Gly Gln Val Leu Leu Ala Lys Leu
                85                  90                  95 atg ggc aaa acc cgt atc att gct gaa acg ggt gct ggt cag cac ggc    336
Met Gly Lys Thr Arg Ile Ile Ala Glu Thr Gly Ala Gly Gln His Gly
            100                 105                 110 gta gca act gct acc gca gca gcg ctg ttc ggt atg gaa tgt gta atc    384
Val Ala Thr Ala Thr Ala Ala Ala Leu Phe Gly Met Glu Cys Val Ile
        115                 120                 125 tat atg ggc gaa gaa gac acg atc cgc cag aaa cta aac gtt gaa cgt    432
Tyr Met Gly Glu Glu Asp Thr Ile Arg Gln Lys Leu Asn Val Glu Arg
    130                 135                 140 atg aaa ctg ctg ggt gct aaa gtt gta ccg gta aaa tcc ggt agc cgt    480
Met Lys Leu Leu Gly Ala Lys Val Val Pro Val Lys Ser Gly Ser Arg
145                 150                 155                 160 acc ctg aaa gac gca att gac gaa gct ctg cgt gac tgg att acc aac    528
Thr Leu Lys Asp Ala Ile Asp Glu Ala Leu Arg Asp Trp Ile Thr Asn
                165                 170                 175 ctg cag acc acc tat tac gtg ttc ggc tct gtg gtt ggt ccg cat cca    576
Leu Gln Thr Thr Tyr Tyr Val Phe Gly Ser Val Val Gly Pro His Pro
            180                 185                 190 tat ccg att atc gta cgt aac ttc caa aag gtt atc ggc gaa gag acc    624
Tyr Pro Ile Ile Val Arg Asn Phe Gln Lys Val Ile Gly Glu Glu Thr
        195                 200                 205 aaa aaa cag att cca gaa aaa gaa ggc cgt ctg ccg gac tac atc gtt    672
Lys Lys Gln Ile Pro Glu Lys Glu Gly Arg Leu Pro Asp Tyr Ile Val
    210                 215                 220 gcg tgc gtg ggt ggt ggt tct aac gct gcc ggt atc ttc tat ccg ttt    720
Ala Cys Val Gly Gly Gly Ser Asn Ala Ala Gly Ile Phe Tyr Pro Phe
225                 230                 235                 240
```

```
atc gat tct ggt gtg aag ctg atc ggc gta gaa gcc ggt ggc gaa ggt    768
Ile Asp Ser Gly Val Lys Leu Ile Gly Val Glu Ala Gly Gly Glu Gly
            245                 250                 255 ctg gaa acc ggt aaa cat gcg gct tct ctg ctg aaa ggt aaa atc ggc    816
Leu Glu Thr Gly Lys His Ala Ala Ser Leu Leu Lys Gly Lys Ile Gly
    260                 265                 270 tac ctg cac ggt tct aag acg ttc gtt ctg cag gat gac tgg ggt caa    864
Tyr Leu His Gly Ser Lys Thr Phe Val Leu Gln Asp Asp Trp Gly Gln
275                 280                 285 gtt cag gtg agc cac tcc gtc tcc gct ggc ctg gac tac tcc ggt gtc    912
Val Gln Val Ser His Ser Val Ser Ala Gly Leu Asp Tyr Ser Gly Val
        290                 295                 300 ggt ccg gaa cac gcc tat tgg cgt gag acc ggt aaa gtg ctg tac gat    960
Gly Pro Glu His Ala Tyr Trp Arg Glu Thr Gly Lys Val Leu Tyr Asp
305                 310                 315                 320 gct gtg acc gat gaa gaa gct ctg gac gca ttc atc gaa ctg tct cgc   1008
Ala Val Thr Asp Glu Glu Ala Leu Asp Ala Phe Ile Glu Leu Ser Arg
                325                 330                 335 ctg gaa ggc atc atc cca gcc ctg gag tct tct cac gca ctg gct tat   1056
Leu Glu Gly Ile Ile Pro Ala Leu Glu Ser Ser His Ala Leu Ala Tyr
            340                 345                 350 ctg aag aag atc aac atc aag ggt aaa gtt gtg gtg gtt aat ctg tct   1104
Leu Lys Lys Ile Asn Ile Lys Gly Lys Val Val Val Val Asn Leu Ser
        355                 360                 365 ggt cgt ggt gac aag gat ctg gaa tct gta ctg aac cac ccg tat gtt   1152
Gly Arg Gly Asp Lys Asp Leu Glu Ser Val Leu Asn His Pro Tyr Val
370                 375                 380 cgc gaa cgc atc cgc                                               1167
Arg Glu Arg Ile Arg
385
```

<210> SEQ ID NO 26
<211> LENGTH: 389
<212> TYPE: PRT
<213> ORGANISM: Artificial Sequence
<220> FEATURE:
<223> OTHER INFORMATION: Synthetic Construct

<400> SEQUENCE: 26

```
Met Lys Gly Tyr Phe Gly Pro Tyr Gly Gly Gln Tyr Val Pro Glu Ile
1               5                   10                  15

Leu Met Gly Ala Leu Glu Glu Leu Glu Ala Ala Tyr Glu Glu Ile Met
            20                  25                  30

Lys Asp Glu Ser Phe Trp Lys Glu Phe Asn Asp Leu Leu Arg Asp Tyr
        35                  40                  45

Ala Gly Arg Pro Thr Pro Leu Tyr Phe Ala Arg Leu Ser Glu Lys
    50                  55                  60

Tyr Gly Ala Arg Val Tyr Leu Lys Arg Glu Asp Leu Leu His Thr Gly
65                  70                  75                  80

Ala His Lys Ile Asn Asn Ala Ile Gly Gln Val Leu Leu Ala Lys Leu
                85                  90                  95

Met Gly Lys Thr Arg Ile Ile Ala Glu Thr Gly Ala Gly Gln His Gly
            100                 105                 110

Val Ala Thr Ala Thr Ala Ala Leu Phe Gly Met Glu Cys Val Ile
        115                 120                 125

Tyr Met Gly Glu Glu Asp Thr Ile Arg Gln Lys Leu Asn Val Glu Arg
    130                 135                 140

Met Lys Leu Leu Gly Ala Lys Val Val Pro Val Lys Ser Gly Ser Arg
145                 150                 155                 160
```

```
Thr Leu Lys Asp Ala Ile Asp Glu Ala Leu Arg Asp Trp Ile Thr Asn
            165                 170                 175

Leu Gln Thr Thr Tyr Tyr Val Phe Gly Ser Val Val Gly Pro His Pro
            180                 185                 190

Tyr Pro Ile Ile Val Arg Asn Phe Gln Lys Val Ile Gly Glu Glu Thr
            195                 200                 205

Lys Lys Gln Ile Pro Glu Lys Glu Gly Arg Leu Pro Asp Tyr Ile Val
        210                 215                 220

Ala Cys Val Gly Gly Gly Ser Asn Ala Ala Gly Ile Phe Tyr Pro Phe
225                 230                 235                 240

Ile Asp Ser Gly Val Lys Leu Ile Gly Val Glu Ala Gly Gly Glu Gly
                245                 250                 255

Leu Glu Thr Gly Lys His Ala Ala Ser Leu Leu Lys Gly Lys Ile Gly
                260                 265                 270

Tyr Leu His Gly Ser Lys Thr Phe Val Leu Gln Asp Asp Trp Gly Gln
            275                 280                 285

Val Gln Val Ser His Ser Val Ser Ala Gly Leu Asp Tyr Ser Gly Val
        290                 295                 300

Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg
                325                 330                 335

Leu Glu Gly Ile Ile Pro Ala Leu Glu Ser Ser His Ala Leu Ala Tyr
                340                 345                 350

Leu Lys Lys Ile Asn Ile Lys Gly Lys Val Val Val Asn Leu Ser
            355                 360                 365

Gly Arg Gly Asp Lys Asp Leu Glu Ser Val Leu Asn His Pro Tyr Val
    370                 375                 380

Arg Glu Arg Ile Arg
385
```